(12) United States Patent  
Slamon et al.

(10) Patent No.: US 6,770,477 B1  
(45) Date of Patent: Aug. 3, 2004

(54) DIFFERENTIALLY EXPRESSED GENES ASSOCIATED WITH HER-2/NEU OVEREXPRESSION

(75) Inventors: Dennis J. Slamon, Woodland Hills, CA (US); Juliana J. Oh, Rowland Heights, CA (US)

(73) Assignee: The Regents of the University of California, Oailand, CA (US)

( * ) Notice: Subject to any disclaimer, the term of this patent is extended or adjusted under 35 U.S.C. 154(b) by 0 days.

(21) Appl. No.: 09/684,405

(22) Filed: Oct. 5, 2000

Related U.S. Application Data

(60) Provisional application No. 60/157,923, filed on Oct. 6, 1999.

(51) Int. Cl.[7] .................... C12N 15/63; C12N 15/79; C12N 15/12; C07H 21/02; C07H 21/04
(52) U.S. Cl. .................. 435/325; 435/69.1; 435/320.1; 536/23.1; 536/23.5; 536/24.3; 536/24.1; 536/24.32; 536/24.33
(58) Field of Search ............................. 536/23.1, 23.5, 536/24.3, 24.31, 24.32, 24.33; 435/320.1, 325, 69.1

(56) References Cited

FOREIGN PATENT DOCUMENTS

| EP | 1 074 617 A | 2/2001 |
|---|---|---|
| WO | WO 01/12659 A | 2/2001 |

OTHER PUBLICATIONS

Schmid, K.J., et al, Proc. Natl. Acad. Sci., USA, 94(18): 9746–9750, 1997.*
Shantz and Pegg, Int J of Biochem and Cell Biol., 1999, vol. 31, pp. 107–122.*
Fu et al, EMBO Journal, 1996, vol. 15, pp. 4392–4401.*
McClean and Hill, Eur J of Cancer, 1993, vol. 29A, pp. 2243–2248.*
Accession #L22067, Aug. 4, 1993.*
Dragoni et al., The Journal of Biological Chemistry, vol. 47, pp. 31119–31124, Nov. 20, 1998.*
Bork, Genome Research, 2000,vol. 10, pp. 398–400.*
Lazar et al., Molecular and Cellular Biology, 1988, vol. 8, pp. 1247–1252.*
Burgess et al., J of Cell Bio. vol. 111, pp. 2129–2138, 1990.*
Bowie et al., Science, 1990, vol. 247, pp. 1306–1310.*
Jeff E. Deyo et al., "drp, a Novel Protein Expressed at . . . Arrest," 1998, DNA and Cell Biology, 17(5):437–447.
D.J. Granville et al., "Overexpression of Bcl–$X_L$ prevents . . . BPD–MA," 1998, FEBS Letters, 422(2):151–154.
N. Inohara et al., "CIDE, a novel family of cell . . . factor," 1998, The EMBO Journal, 17(9):2526–2533.
E.F. Kirkness et al., "The TIGR Human cDNA Databas," Methods in Molecular Biology, 69:261–269.
S. Mitamura et al., "Cytosolic Nuclease Activated . . . DFF–45[1]," 1998, Biochemical and Biophysical Research Communications, 243:480–484.
S. Liu et al., "DFF, a Heterodimeric Protein . . . Apoptosis," 1997, Cell, 89:175–184.
J. Oh et al., "Identification of differentially expressed genes associated with HER–2/neu overexpression in human breast cancer cells," 1999, Nucleic Acids Research, 27(20):4008–4017.
Ota, T. et al., Abstract—XP002236767, Database Accession No. AAB94820, EMBL "Online" Jun. 26, 2001.
Wiemann, S., Abstract—XP002236768, Database Accession No. AX086418, EMBL "Online" Mar. 6, 2001.

* cited by examiner

Primary Examiner—Anthony C. Caputa
Assistant Examiner—Anne L. Holleran
(74) Attorney, Agent, or Firm—Gates & Cooper LLP

(57) ABSTRACT

The present invention provides human Her-2/neu overexpression modulated proteins (HOMPS) and polynucleotides encoding HOMPS polypeptides. The invention also provides HOMPS containing expression vectors and host cells, HOMPS antibodies and methods of producing HOMPS. In addition, the invention provides methods for generating, identifying and manipulating HOMPS.

13 Claims, 21 Drawing Sheets

```
   1  GGCACGAGCT GCGATAATAG CGAGGCAGCA GTGCAGCTTT CAGAGGGTCC
  51  GGGCTCAGAG GGGCTATGAT TCGGAGGGTT CTGCCGCACG GCATGGGCCG
 101  GGGCCTCTTG ACCCGGAGGC CAGGCACGCG CAGAGGAGGC TTTTCTCTGG
 151  ACTGGGATGG AAAGGTGTCT GAGATTAAGA AGAAGATCAA GTCGATCCTG
 201  CCTGGAAGGT CCTGTGATCT ACTGCAAGAC ACCAGCCACC TGCCTCCCGA
 251  GCACTCGGAT GTGGTGATCG TGGGAGGTGG GGTGCTTGGC TTGTCTGTGG
 301  CCTATTGGCT GAAGAAGCTG GAGAGCAGAC GAGGTGCTAT TCGAGTGCTA
 351  GTGGTGGAAC GGGACCACAC GTATTCACAG GCCTCCACCG GCTCTCAGT
 401  AGGTGGGATT TGTCAGCAGT TCTCATTGCC TGAGAACATC CAGCTCTCCC
 451  TCTTTTCAGC CAGCTTTCTA CGGAACATCA ATGAGTACCT GGCCGTAGTC
 501  GATGCTCCTC CCCTGGACCT CCGGTTCAAC CCCTCGGGCT ACCTCTTGCT
 551  GGCTTCAGAA AAGGATGCTG CAGCCATGGA GAGCAACGTG AAAGTGCAGA
 601  GGCAGGAGGG AGCCAAAGTT TCTCTGATGT CTCCTGATCA GCTTCGGAAC
 651  AAGTTTCCCT GGATAAACAC AGAGGGAGTG GCTTTGGCGT CTTATGGGAT
 701  GGAGGACGAA GGTTGGTTTG ACCCCTGGTG TCTGCTCCAG GGGCTTCGGC
 751  GAAAGGTCCA GTCCTTGGGA GTCCTTTTCT GCCAGGGAGA GGTGACACGT
 801  TTTGTCTCTT CATCTCAACG CATGTTGACC ACAGATGACA AAGCGGTGGT
 851  CTTGAAAAGG ATCCATGAAG TCCATGTGAA GATGGACCGC AGCCTGGAGT
 901  ACCAGCCTGT GGAATGCGCC ATTGTGATCA ACGCAGCCGG AGCCTGGTCT
 951  GCGCAAATCG CAGCACTGGC TGGTGTTGGA GAGGGGCCGC CTGGCACCCT
1001  GCAGGGCACC AAGCTACCTG TGGAGCCGAG GAAAAGGTAT GTGTATGTGT
1051  GGCACTGCCC CCAGGGACCA GGCCTAGAGA CTCCGCTTGT TGCAGACACC
1101  AGTGGAGCCT ATTTTCGCCG GGAAGGATTA GGTAGCAACT ACCTAGGTGG
1151  TCGTAGCCCC ACTGAGCAGG AAGAACCGGA CCCGGCGAAC CTGGAAGTGG
1201  ACCATGATTT CTTCCAGGAC AAGGTGTGGC CCCATTTGGC CCTGAGGGTC
1251  CCAGCTTTTG AGACTCTGAA GGTTCAGAGC GCCTGGGCCG GCTATTACGA
1301  CTACAACACC TTTGACCAGA ATGGCGTGGT GGGCCCCCAC CCGCTAGTTG
1351  TCAACATGTA CTTTGCTACT GGCTTCAGTG GTCACGGGCT CCAGCAGGCC
1401  CCTGGCATTG GGCGAGCTGT AGCAGAGATG GTACTGAAGG GCAGGTTCCA
1451  GACCATCGAC CTGAGCCCCT TCCTCTTTAC CCGCTTTTAC TTGGGAGAGA
```

FIG. 1A

1501 AGATCCAGGA GAACAACATC ATCTGAGCAT GTGTGCTCTG CACTGGCTCC
1551 ACTGGCTTGC ATCCTGGCTG TGTTCACAGC CTTGTTTGCT GCTTCCATCT
1601 TCCCCAGTAC TGTGCCAGGC CTTCTCCCCC TCCCCAGTGT CCTCTCCTCT
1651 CAGGCAGGCC ATTGCACCCA TATGGCTGGG CAGGCACAGG CAGTGAGGCC
1701 GAGGCCAATA GCGAGTGATG AGCGGGATCC TAGGACTGAT CTGTAGCCCA
1751 TGCTGATGTC ACCCACCAGG GCAATCCATC TGGAGGCCTG AGCACCCTGG
1801 CCCAGGACTG GCTTCATCCT GGCACTGACC AGGAAAGACT GCCTCTGACC
1851 CTCTTAGCAG ACAGAGCCCA GGCATGGGAG CACTCTGGGG CAGCCTGGCT
1901 CAGGTTTATT GATTTTCGTC TGTTTACCCT ATCCATTAAT CAATACATGT
1951 AATTAACTCC TAAAAAAAAA AAAAAAAAA A

FIG. 1B

```
  1  MIRRVLPHGM  GRGLLTRRPG  TRRGGFSLDW  DGKVSEIKKK  IKSILPGRSC
 51  DLLQDTSHLP  PEHSDVVIVG  GGVLGLSVAY  WLKKLESRRG  AIRVLVVERD
101  HTYSQASTGL  SVGGICQQFS  LPENIQLSLF  SASFLRNINE  YLAVVDAPPL
151  DLRFNPSGYL  LLASEKDAAA  MESNVKVQRQ  EGAKVSLMSP  DQLRNKFPWI
201  NTEGVALASY  GMEDEGWFDP  WCLLQGLRRK  VQSLGVLFCQ  GEVTRFVSSS
251  QRMLTTDDKA  VVLKRIHEVH  VKMDRSLEYQ  PVECAIVINA  AGAWSAQIAA
301  LAGVGEGPPG  TLQGTKLPVE  PRKRYVYVWH  CPQGPGLETP  LVADTSGAYF
351  RREGLGSNYL  GGRSPTEQEE  PDPANLEVDH  DFFQDKVWPH  LALRVPAFET
401  LKVQSAWAGY  YDYNTFDQNG  VVGPHPLVVN  MYFATGFSGH  GLQQAPGIGR
451  AVAEMVLKGR  FQTIDLSPFL  FTRFYLGEKI  QENNII
```

FIG. 2

```
   1 GGCACGAGCG GGGACGGAGC GAGCCGGCGC CAGGGCCCCT CGGGCCGGGA
  51 AGAGGGGAAG GGGAGCGAGG TTGATGCCCG GCGGAGGGGC GAGCGCGGCG
 101 TCTGGCCGGC TTCTCACCGC CGCGGAGCAA AGAGGGTCCC GGGAAGCGGC
 151 AGGGTCGGCG TCCAGGAGCG GCTTCGGGGG CTCCGGCGGC GGCAGAGGCG
 201 GAGCAAGCGG CCCCGGGTCC GGGAGCGGAG GCCCTGGGGG CCCCGCGGGC
 251 AGGATGAGCT TGACCCCGAA GGAGCTCTCG AGCCTGCTGA GCATCATATC
 301 GGAGGAGGCG GGCGGCGGCA GCACCTTCGA GGGCCTGTCC ACCGCCTTCC
 351 ACCACTACTT CAGCAAGGCC GACCACTTCC GCCTGGGCTC GGTGCTCGTC
 401 ATGCTGCTCC AGCAGCCCGA CCTGCTGCCT AGCGCGGCGC AGCGCCTCAC
 451 GGCGCTCTAC CTGCTCTGGG AGATGTACCG CACCGAGCCG CTGGCCGCCA
 501 ACCCCTTCGC CGCCAGCTTC GCGCACCTGC TCAACCCCGC GCCGCCCGCC
 551 CGCGGCGGCC AGGAACCCGA CCGCCCTCCG CTCTCAGGAT TTTTACCTCC
 601 TATAACTCCA CCAGAAAAGT TTTTTCTTTC CCAGCTGATG CTGGCACCCC
 651 CACGGGAACT CTTCAAAAAG ACGCCTCGCC AGATTGCACT GATGGACGTT
 701 GGAAACATGG GCCAGTCTGT GGACATTAGT GGGCTTCAGT TAGCCTTGGC
 751 CGAACGCCAA TCTGAATTGC CAACGCAAAG CAAAGCGAGC TTCCCCAGTA
 801 TTCTCAGTGA CCCAGACCCG GATTCTTCTA ATTCTGGATT TGACAGCTCA
 851 GTTGCCTCTC AGATCACAGA AGCTTTAGTC AGCGGACCAA AGCCACCTAT
 901 TGAAAGCCAT TTTCGACCAG AGTTTATTCG TCCACCGCCT CCACTCCACA
 951 TTTGTGAGGA TGAACTTGCT TGGCTAAACC CCACGGAGCC TGACCACGCG
1001 ATCCAGTGGG ATAAATCGAT GTGTGTTAAG AATAGCACTG GTGTGGAGAT
1051 CAAACGAATA ATGGCCAAAG CCTTCAAAAG CCCCTTATCC TCTCCCCAAC
1101 AAACACAGCT ACTTGGTGAG TTGGAAAAAG ACCCCAAACT TGTCTACCAT
1151 ATTGGCCTCA CCCCAGCCAA ACTTCCTGAC CTTGTGGAAA CAACCCCTTT
1201 AGTCGCTATA GAAATGTTGC TGAAATTAAT GCAGTCAAGC CAGATCACTG
1251 AGTATTTCTC TGTCCTGGTC AATATGGACA TGTCTTTACA TTCAATGGAA
1301 GTTGTAAATC GACTAACTAC AGCTGTTGAT CTACCTCCTG AATTTATTCA
1351 CCTTTATATA TCAAATTGCA TCTCTACTTG TGAACAGATT AAGGATAAAT
1401 ATATGCAGAA TCGGTTGGTG CGTCTTGTGT GTGTGTTTCT CCAATCCTTG
1451 ATCCGTAACA AAATTATTAA TGTACAGGAT TGTTTATAG AAGTGCAGGC
1501 ATTCTGTATT GAATTCAGTA GGATACGAGA AGCTGCTGGT CTTTTCCGGT
```

FIG. 3A

```
1551  TGTTGAAGAC ATTGGATACT GGGGAAACAC CTTCTGAGAC CAAAATGTCA
1601  AAATAATACC TCATCAGAAC CATCCCATCC ATTCACTGTT CAGCTGTACT
1651  GTGATTTAGT TTTTACACCG TTAAAACCCT GAGTGGATTG CTTGGTTTAA
1701  TGCATATAAA CAGTACTTTA TCTACTTAAA GCAAAAAAAA AAAAAAAAA
```

FIG. 3B

```
  1 MPGGGASAAS GRLLTAAEQR GSREAAGSAS RSGFGGSGGG RGGASGPGSG
 51 SGGPGGPAGR MSLTPKELSS LLSIISEEAG GGSTFEGLST AFHHYFSKAD
101 HFRLGSVLVM LLQQPDLLPS AAQRLTALYL LWEMYRTEPL AANPFAASFA
151 HLLNPAPPAR GGQEPDRPPL SGFLPPITPP EKFFLSQLML APPRELFKKT
201 PRQIALMDVG NMGQSVDISG LQLALAERQS ELPTQSKASF PSILSDPDPD
251 SSNSGFDSSV ASQITEALVS GPKPPIESHF RPEFIRPPPP LHICEDELAW
301 LNPTEPDHAI QWDKSMCVKN STGVEIKRIM AKAFKSPLSS PQQTQLLGEL
351 EKDPKLVYHI GLTPAKLPDL VENNPLVAIE MLLKLMQSSQ ITEYFSVLVN
401 MDMSLHSMEV VNRLTTAVDL PPEFIHLYIS NCISTCEQIK DKYMQNRLVR
451 LVCVFLQSLI RNKIINVQDL FIEVQAFCIE FSRIREAAGL FRLLKTLDTG
501 ETPSETKMSK
```

FIG. 4

```
   1  GGCACGAGCT GGCTCGCGCG TGCCTTTTCC CCTCAGGTTG TGGGGAGAGC
  51  GGAATCCTGC TCCGCCGTCG CAGCAGCAGC GGCAGCCCCG GCAGCCTCGG
 101  GCGACAGCGG CGGCGCGCGA GCCCCCGGGC GGACCGTACC ACCGCTCGCC
 151  AGCACGCAGG GGGAGCCGCC CGTCTCGCCG CGCACGCCTC GGCGACCCCG
 201  CGGGGCTGAG GCGTCGCCGC GCCCGGCAGC GTGAGCGCAG AGCCGGCCTC
 251  GACCCCGAGC TCGGAGCCCC GCGGGCCGCG CCCGCCGCCG GCCCCACCCA
 301  TCCGGGTCGA GGAGGCCGAG GCCATGGCTG AGACGGAGGA GCGGAGCCTG
 351  GACAACTTCT TTGCCAAGAG GGACAAGAAG AAGAAGAAGG AGCGGAGCAA
 401  CCGGGCGGCG AGTGCCGCGG GCGCAGCGGG CAGCGCCGGC GGAAGCAGTG
 451  GAGCCGCGGG TGCGGCGGGC GGCGGGGCGG GCGCGGGGAC CCGGCCGGGT
 501  GACGGCGGGA CCGCCAGCGC GGGGGCTGCG GGCCCAGGGG CCGCCACCAA
 551  GGCTGTGACG AAGGACGAAG ATGAATGGAA AGAATTGGAG CAAAAAGAGG
 601  TTGATTACAG CGGCCTCAGG GTTCAGGCAA TGCAAATAAG CAGTGAAAAG
 651  GAAGAAGACG ATAATGAAAA GAGACAAGAT CCAGGTGATA ACTGGGAAGA
 701  AGGTGGAGGT GGTGGTGGAG GTATGGAAAA ATCTTCAGGT CCCTGGAATA
 751  AAACAGCTCC AGTACAAGCA CCTCCTGCTC CAGTAATTGT TACAGAAACC
 801  CCAGAACCAG CGATGACTAG TGGTGTGTAT AGGCCTCCTG GGGCCAGGTT
 851  AACCACAACA AGGAAAACAC CACAAGGACC ACCAGAAATC TACAGTGATA
 901  CACAGTTCCC ATCCCTGCAG TCAACTGCCA AGCATGTAGA AAGCCGGAAG
 951  GATAAAGAAA TGGAGAAGAG CTTTGAAGTA GTAAGACACA AAAATAGAGG
1001  TAGGGATGAG GTTTCAAAAA ACCAGGCCCT TAAACTTCAG CTAGACAACC
1051  AATATGCTGT GCTTGAAAAT CAGAAAAGCA GCCACTCACA ATACAATTAA
1101  GGAATGGGCT TTGCTAACCC TTCTGAGGTA ACTAGACTGC AGCTAACCAC
1151  CACCAACAGC CATTCATCAT CTGATCTCTG CTGGATCTAC AGACACCGAT
1201  GCAGACCACT CGATTTCATG ACCGGCCCTA TTGCACTATG GAAGTTAAAG
1251  TGTCACGACT GCTCTATGCA TATTGGATTT AGGGGAATTT TCATTGTTAC
1301  ATAAATGTGT GAACTAGTTT CAACAGTGTT CTTTCATATT TACTCTGCAA
1351  ATACAAAAAA CCAAAACCTG CAGCCAGTGG TCATTTCAAA ATCTTTTTAT
1401  GTTCAGATAC TGAGCCTTCA TAAGGGTTGA CTACCTCAGA TTTGCTGCAC
1451  TCATTGTGGA CTTCATGTGG ATCACAACTT CTGGATAAGA AGATTACAAC
1501  TATTAAGTGT CGATGTGAAC CTTGCAACCA GCTCTACTGG ATTCTTATCA
```

FIG. 5A

```
1551  GAAATCCTGC ATAAAAAGTC AGCCATCTGG GTTCTGATCT GCTGTAAAAG
1601  ATGAAGATTT AAGTGACCTT AATTAACCTG TCCTGTGCCC TACCCTTAAG
1651  GAATACTCTC TGTAGTAGGC TGTTGTTATA TTAGACTTCC TGGAACACAC
1701  CGCTGAAAAG AACTGATGTG TTCAGATCAT CTGTGTAGGG CTGTGATTTG
1751  TAATTTAAAC TAATTGTATT CTGAGGTAAC CACAAAATAA ATTCAACCAA
1801  ACTGGGGTCC ACCAAGTGGG GGAAGGGGAA GGGAGAGAAT AATCTTGGGG
1851  GTTTTTTTTT TTGGTAATTT TTTTATTTGG ATAGTGCTTT TTTGTTTTGT
1901  TTTTGTTCTG CATTAAGGCC TTTTTTGCTT TGACTTGAAA TAAGTTCTTT
1951  GACAGAGCAT ATTGCTTGGT TAATTAAGTA ACCTAAAGTA TGCATTAGGA
2001  TTGTGAAATG TCTCGTGAGT ATGCCAATCC TGAGGGTGGA ACCAAATAGC
2051  CTTTGATGAA AAGGGCAGTG GATTCTGGAG GCTCTACTTC AGGTGCTGCT
2101  ATAATGCCTC ATCTAATCAG GACTAAATTG TGTAGGAAAC TGCAGTGGGA
2151  AGAATATGCT TTCTGCTCAG GCTAAGAGGG TCACTGATCT GTCCTTAGAA
2201  ATTCAGAGTA ACATGAGCAA AACCTCAGCT AAAACCCATT TAAGTGGCAT
2251  GGATTGTGCA TGATCTTTGA TAAGAATTCC TCATGTACTT GTGCCTAGTT
2301  TTTCAAGGTA TTGGCTGTTC TATAGATGCA GTGATTGTCC CAGCTAGCTC
2351  TGTTACCAGC CTTTTGGTGT GTCTTTATGT TCATTTGGAG AGTCAGGGCG
2401  AAAGACAGGT GATGTAGCAC TTCTGTTTTT AATAATTATT GCTTAAAATA
2451  CCTATTAATA GTTTTGGGTC ATTTAAAGGG ACTTGAGGAA GCTACCCAGG
2501  ATTACAGAAG AGTGTCCACC TAACAAGATG GTCTGGCAGT TTCCTAGTTT
2551  TGTATCTGGT TCAATAGAAA TATGTGAAAG TGGTAATGTC ATCATTTGAT
2601  GCAGAGTCCG GGTTTCTCTA TAATAAATCC CTTTGCCAAA TGCATGAGTT
2651  GCAGACTTGC TACTGGCAAG AGTGAAGCAA GTGGGTGAGT AAAACTATTT
2701  TGACGTGGGA GCGTTTTCAG ATAGGAGTTT AGTCTTGACG AAAGTGTCCG
2751  TGCAGGAATT GGACTCCGAG GAGGGTTACA GTATCTCCTG ACGGGACCTG
2801  CCACTCGCAT CTGGGCAATG TTGACATTTG AGGTGGCAGG CAGGATGCCT
2851  GCCTTCTAAT ATATTTGGGT GAGTAACTGA GCCAGCCAAG GGAAGGTTGA
2901  ATGATTAAAT CAGAAATGGG ATTCTTGGTA AACTGAAGAC TTTTATTTGG
2951  GAATGAAAAA CCTTAAAAAA ATCTCTTCAT CGTTGAACTG TGCATTTTCC
3001  CTGCATTTTT TCCCAACAAA ATTTTGTTGG GGGTTATGTT ACTGAAGAAT
3051  GAACAGATGA GTAAGTGGAG GTGTTATGTA AAGGCATATT GTACTCGAAA
3101  TCTGAAGACC TGCAGCAGAT TTAAATTACA ACTCTTGTTA TAACTTTTTA
3151  AAAGATTGTG AAAATATCAA AATATAAATG AATCAAGTTT TAATATACTG
3201  TATGATGGGT GGATGAGGCT GTCCATTGTA CCATTTGTTT GAATTCTCAG
3251  GCATGGTTTG GCAGTGCAAG AATTCTGTAA CATTAACAAA TTCAATAAAA
3301  AGTAAATATA TGGAAAAAAA AAAAAAAAAA AAAAAAAAAA AAAAA
```

FIG. 5B

```
  1  MAETEERSLD NFFAKRDKKK KKERSNRAAS AAGAAGSAGG SSGAAGAAGG
 51  GAGAGTRPGD GGTASAGAAG PGAATKAVTK DEDEWKELEQ KEVDYSGLRV
101  QAMQISSEKE EDDNEKRQDP GDNWEEGGGG GGGMEKSSGP WNKTAPVQAP
151  PAPVIVTETP EPAMTSGVYR PPGARLTTTR KTPQGPPEIY SDTQFPSLQS
201  TAKHVESRKD KEMEKSFEVV RHKNRGRDEV SKNQALKLQL DNQYAVLENQ
251  KSSHSQYN
```

FIG. 6

```
GGCAC GAGGTGGCAT AGCATAACCA CAGTAAGAAC
      AGAACAGATA TTCAGCAGAA AACTTTTTAT ACTCTAATTC TTTTTTTTTT
      TTTTTTTGAG ACAGAGTTTT AGTCTTGTTT CCCAGGCTGG AGTGCAATGG
      CACAATCTTG GCTCACTGCA ACCTCCGCCT CCTGGGTTCA GGCAATTTTC
      CTGCCTCAGC CTCCCAAGTA GCTGGGATTA CAGGCACCCA CCACCATGCC
      CAGCTAATTT TTGTATTTTT AATAGAGAGC TAATAATTGT ATATTTAATA
      AAGACGGGTT TCACCATGTT GGCCAGGCTG GTCTTGAACT CCTGACCTCA
      GGTGATCCTC CTGCATTGGC CTCCCAAAGT GCTGGAATTC CAGGCATGAG
      CCACTGCGCC CAGTCTACAC ACTAATTCTT GTTAGCCCAA CAGCTGTTCT
      GTTCTATCTA CCCCTCATTT CACGCTCAAG GAGTCATACC TAGAATAGTT
      ACACACAAGA GGGAAACTGG AAGCCAAACA CTGTACAGTA TTGTGTAGAA
      AGTCACCTCC CTACTCCTTT TATTTTACAT GAGTGCTGAT GTGTTTTGGC
      AGATGAGCTT TCAGCTGAGG CCTGATGGAA ATTGAGATAA CCTGCAAAGA
      CATAACAGTA TTTATGAGTT ATATCTTAGT TCTTGAAATT GTGGAATGCA
      TGATTGACAA TATATTTTTA ATTTTTATTT TTTCAAGTAA TACCAGTACT
GTTTAACTAT AGCCAGAACT GGCTAAAATT TTTATATTTT CAGAGTTGAA
GTTGGTGAAG ACATTCATGA TTTAAACACC AGATCCTGAA AGGGGTTAAA
TCTACTTTGA AATGAATCTG CAATCAGTAT TTCAAAGCTT TTCTGGTAAT
TTTAGTGATC TTATTTGATT AGACTTTTTC AGAAGTACTA AATAAGGAAT
TTTAACAGGT TTTTATTAAT GCACAGATAA ATAGAAGTAC AGTGAGGTCT
ATAGCCATTT TATTAAAATA GCTTAAAAGT TTGTAAAAAA ATGAATCTTT
GTAATTACTT AATATGTTAG TTAAGAACCC GTCAAGCTTA TATTTGCTAG
ACTTACAAAT TATTTTAAAT GCATTTATCT TTTTTGACAC TATTCAGTGG
AATGTGTAAG CTAGCTAATT CTTGTTTTCT GATTTAAAGC ACTTTTAAAT
CTTATCCTGC CCCCTAAAAA CAAAAGGTTT TGATCACAAG GGGAAATTTA
AGATTGTTAA CCCTGTTTTT CAGAAGGGCT ACTGTTAATT GCACATAAAC
ATGAAATGTG TTTTCCCCTG TGTACTAACA CATTCTAGGC AAAATTCAAA
CTTATAGTGG TAAAGAAACA GGTTGTTCAC TTGCTGAGGT GCAAAAATTC
TTAAGACTTC TGTTTGAAAT TGCTCAATGA CTAGGAAAAG ATGTAGTAGT
TTACTAAAAT TGTTTTTCTA CCATATCAAA TTAAACAATT CATGCCTTTT
TAGGGTCAGG CCTACAATGA ATAGGTATGG TGGTTTCACA GAATTTTAAA
ATAGAGTTAA AGGGAAGTGA TGTACATTTC GGGGGCATTA GGGTAGGGAG
ATGAATCAAA AAATACCCCT AGTAATGCTT TATATTTTAA TACTGCAAAA
GCTTTACAAA TGGAAACCAT GCAATTACCT GCCTTAGTTC TTTTGTCATA
AAAACAATCA CTTGGTTGGT TGTATTGTAG CTATTACTTA TACAGCAACA
TTTCTTCAAT TAGCAGTCTA GACATTTTAT AAACAGAAAT CTTGGACCAA
TTGATAATAT TTCTGACTGT ATTAATATTT TAGTGCTATA AAATACTATG
TGAATCTCTT AAAAATCTGA CATTTTACAG TCTGTATTAG ACATACTGTT
TTTATAATGT TTTACTTCTG CCTTAAGATT TAGGTTTTTT AAATGTATTT
TTGCCCTGAA TTAAGTGTTA ATTTGATGGA AACTCTGCTT TTAAAATCAT
CATTTACTGG GTTCTAATAA ATTAAAAATT AAACTTGTAA AAAAAAAAA
AAAAAAAAAA AAAAAAAAAA AAAAAAAAAA AAA
```

FIG. 7

```
  1 GGCACGAGGT CCCACCTTGT GGAGGATGGA GGTGACCGGG GACGCCGGGG
 51 TACCAGAATC TGGCGAGATC CGGACTCTAA AGCCGTGTCT GCTGCGCCGC
101 AACTACAGCC GCGAACAGCA CGGCGTGGCC GCCTCCTGCC TCGAAGACCT
151 GAGGAGCAAG GCCTGTGACA TTCTGGCCAT TGATAAGTCC CTGACACCAG
201 TCACCCTGGT CCTGGCAGAG GATGGCACCA TAGTGGATGA TGACGATTAC
251 TTTCTGTGTC TACCTTCCAA TACTAAGTTT GTGGCATTGG CTAGTAATGA
301 GAAATGGGCA TACAACAATT CAGATGGAGG TACAGCTTGG ATTTCCCAAG
351 AGTCCTTTGA TGTAGATGAA ACAGACAGCG GGCAGGGTT GAAGTGGAAG
401 AATGTGGCCA GGCAGCTGAA AGAAGATCTG TCCAGCATCA TCCTCCTATC
451 AGAGGAGGAC CTCCAGATGC TTGTTGACGC TCCCTGCTCA GACCTGGCTC
501 AGGAACTACG TCAGAGTTGT GCCACCGTCC AGCGGCTGCA GCACACACTC
551 CAACAGGTGC TTGACCAAAG AGAGGAAGTG CGTCAGTCCA AGCAGCTCCT
601 GCAGCTGTAC CTCCAGGCTT TGGAGAAAGA GGGCAGCCTC TTGTCAAAGC
651 AGGAAGAGTC CAAAGCTGCC TTTGGTGAGG AGGTGGATGC AGTAGACACG
701 GGTATCAGCA GAGAGACCTC CTCGGACGTT GCGCTGGCGA GCCACATCCT
751 TACTGCACTG AGGGAGAAGC AGGCTCCAGA GCTGAGCTTA TCTAGTCAGG
801 ATTTGGAGGT GGGCGGAAAC CAGGGTCACT GAGCTACAGA GGAGGACATG
851 CCCTGGGATG TAGTAGTATC ATGCAGAGGT GTGTGGGCCC TTTTGTTCAC
901 CTCTGCAGAC TGTGAATCCT AGCTGCCAGT TTGCCTATTA TATGCCAAGG
951 CATTTGCAAA AATCTCATTA ATCTAAATCA AATAGCTTT AAAGAAAAAT
1001 GCAAAAAAAA AAAAAAAAA AAAAAA
```

FIG. 8

1    MEVTGDAGVP ESGEIRTLKP CLLRRNYSRE QHGVAASCLE DLRSKACDIL
  51   AIDKSLTPVT LVLAEDGTIV DDDDYFLCLP SNTKFVALAS NEKWAYNNSD
 101   GGTAWISQES FDVDETDSGA GLKWKNVARQ LKEDLSSIIL LSEEDLQMLV
 151   DAPCSDLAQE LRQSCATVQR LQHTLQQVLD QREEVRQSKQ LLQLYLQALE
 201   KEGSLLSKQE ESKAAFGEEV DAVDTGISRE TSSDVALASH ILTALREKQA
 251   PELSLSSQDL EVGGNQGH

FIG. 9

```
   1 GGCACGAGGC TAAATGTAGA CAATGGTTAG AGAAGAATTT TCCAAATGAA
  51 TTTGCAAAAC TTACTGTAGA AAATTCACCC AAACAAGAAG CTGGAATTAG
 101 TGAGGGTCAA GGAACAGCAG GGGAAGAAGA GGAGAAGAAA AAACAGAAGA
 151 GAGGTGGAAG GGGTCAAATA AAACAAAAAA AGAAGACCGT ACCACAAAAG
 201 GTTACTATAG CCAAAATTCC CAGAGCAAAG AAGAAATATG TGACAAGAGT
 251 ATGTGGCCTT GCAACTTTTG AAATTGATCT TAAAGAAGCA CAAAGATTTT
 301 TTGCTCAAAA ATTCTCCTGT GGTGCCTCAG TAACAGGGGA GGATGAAATT
 351 ATCATTCAGG GAGATTTTAC AGATGACATA ATTGATGTCA TTCAGGAAAA
 401 ATGGCCAGAG GTAGATGATG ACAGCATCGA AGATCTTGGA GAAGTAAAGA
 451 AGTGAATTTG AAAATTTGTC TGTATTTAAT GGCCTGAACT GAGAGTTGAT
 501 ATGGCCAAAG GGAGAGAGGC CTTTTAAAAT ATATATATAT ATACACATAT
 551 ATATGTATAT ATACACATAT ATGTATGTAT ACACATATAC ACATGTATAT
 601 ATACATGTGT GTATGTATGC ATGTATATAC ATATATACAT ACACATATAT
 651 GTATACATAT ATACACATAT ATGTATACAT ATATACACAT ATATGTATAC
 701 ATATATATAT ATTCTACAGT AAAACTGTAG ACTGTCCTCG TCCTTGGCAT
 751 TTTCACTGTT CTGTACAAGG CTGCTTGTTT TTTTATTGCC AAAGTCAAAT
 801 AAACGGGAGA CTGTCATGCT CATGCATGAA TAGAATTTAG TCAAATAAAA
 851 AATTTTGGTC ATTTGGTACT GACTTTCTCT CTCTCTCTCT CTCTCTTTTT
 901 TTTTTTTGAC AGAGTCTCGC ACTGTTGCCT GGGCTGGAAT GCAGTGGTGC
 951 GATCTCGGCT CACTGCAACC TCCGCCTCCC GGGTTCAAGT GATTCTCCTG
1001 CCTCAGCCTC CCAAGTAGGT GGGATTACAG GCGCCCGCCA CCACGCCCAG
1051 CTAATTTTTG TATTTTTAGT AGAGATGGGG TTTCACTATG TTGGCCAGGC
1101 TGGTCTCGAA CTCCTGACCT CGTGATTGGC CCACCTCAGC CTCCCAAAGT
1151 GCTGGTATTA CAGATGTGAG CCACCGCACC CAGCCTGAGT TTCTCTTTCT
1201 CTCTTTTTAA CTTTATTTTT TGAAAACCCC GGTAGACTTT GTGGGGAGCA
1251 TTTTTGTTGA TAATTTTACT GATCTAAAGC TGAGTGATTT TTTAAAAGAA
1301 TTTGAATTTG GCTTCCTCAC CAGTAATATG TCTCCTTGCT TCTTTGATGT
1351 GATAGTTTTG AGATGGGTGA GAATCTAATA GATCTGTGGT TGAATTTGCT
1401 GTGTTGTTAT GAAGTCCACC CTGTGGGCAC AATAACATAA CTGTTGGTAG
1451 GAGTTGTTTG AGCTATTCTG GAGATTATTT GGTAAAGTAT ACTAAAAGCC
1501 TTAAAACCAT GTATGTGCGC TGTTTGAACC AGTAAGCCAC TTCTTTGACA
1551 TTAGAAGACA TTAGAAGAAA TAATCAGCCT TGCATAAAAC TTATGGATGA
```

FIG. 10A

```
1601  AAGTATTCAT CACAATATTA TTTATAATAA AAAATTGCAA ATGTTATAAA
1651  TGAACAATTG GGAAATGGTT AAAGAAGTGA TGGTGCATTG TGTGGTAGAA
1701  TATTATGCAT ATGTTTAAAG AATCATATTT TCTAAGATTA TTTGGAAGCA
1751  TGTTTGGTAA TGTCAAGTGG AGTACCCCAG ATACATTTTA GACATTTATC
1801  GTCATCATCT GCTCTGAGTG GAAGGCCGTT CAGAGAGGCT AGAGGTTCTT
1851  ATTCTGGCTA TAAATTATGT GAGTAAAATT GTGCTAACCA GTTAAAAGTA
1901  CTGTACACCC ATGCTCAATA TATAGTCCTG GAAATAGCAA TTGAAACATG
1951  TCTTCTCACA AGAGAAAATG ACAGTTTTAA TGATGTATTT GATGAATTTA
2001  AACTTTAAGT CAGGTGCTGC AAATTGGAAA GAAGACTTGT GGTGTTTTAA
2051  GTTGCTGTGG ACACTTTTAA GAAACTTAGA ACCCATGGAA CCCTTGTTTA
2101  TCGCCATGCA AATTACAATC TTGAATGAGT GTTTTTTTAA AAATAAAGTA
2151  TTAGAAAAAT GTGTAGTAAA GATGTAAAAT TAAAAAAAAA AAAAAAAAA
2201  AAAAAAAAAA AAAA
```

FIG. 10B

```
  1  HEAKCRQWLE KNFPNEFAKL TVENSPKQEA GISEGQGTAG EEEEKKKQKR
 51  GGRGQIKQKK KTVPQKVTIA KIPRAKKKYV TRVCGLATFE IDLKEAQRFF
101  AQKFSCGASV TGEDEIIIQG DFTDDIIDVI QEKWPEVDDD SIEDLGEVKK
```

```
                    104 LGSVLVMLLOOPDLLPSAAORL 125
                          L2
         74                              1604
                         C40                   (A)N 1750
```

```
H17        PEHSDVVIVG GGVLGLSVAY WLKKLESRRG AIRVLVVERD HTYSQASTGL SVGGICQQFS LPENIQLSLF SASFLRNINE 140
Z77667     PYRAEIVIIG GGLSGSSTAF WLKE-RFRDE DFKVVVVENN DVFTKSSTML STGGITQQFS IPEFVDMSLF TTEFLRHAGE 169
AE001086   ...MKVAVIG GGVAGLSAAY FLAKAG---A DVKVF-EQKY LLY--GASGR NSGGLTAQFT NEAMIKLA-- ----KRTLEL  65

H17        YLAVVDAPPL DLRFNPSGYL LLASEKDAAA MESNV-KVQR QEGAKVSLMS PDQLRNKFPW INTEGVALAS YGMEDEGWFD 219
Z77667     HLRILDSEQP DINFFPTGYL RLAKTDEEVE MMRSAWKVQI ERGAKVQLLS KDELTKRYPY MNVDDVLLAS LGVENEGTID 249
AE001086   YDELQSEVGF NFLLRRDGYV KIAGKGEEAK LREEV-EFQR KAGVKVKMVE PEFVKELFPD INTSAFTAAS YFADGGVVF-  143

H17        PWCLLQGLRR KVQSLGVLFC QGEVTRFVSS SQRM------ ----LTTDDK AVVLKRIHEV HVKMDRS-LE YQPVECAIVI 288
Z77667     TWQLLSAIRE KNITLGVQYV KGEVEGFQFE RHRASSEVHA FGDDATADEN KLRAQRISGV LVRPQMNDAS ARPIRAHLIV 329
AE001086   PWPVVWGLAK GCRELGVEIY DYTPASVEVK GNDLTVKASG ESYKVDYIIN AAGAWSNEIS QQAGVELNNK VFREEICVTE

H17        NAAGAWSAQI AALAGVGEGP PGTLQGTKLP VEPRKRYVYV WHCPQGPGLE TPLVADTSGA YFRREGLGSN YLGGRSPTEQ 368
Z77667     NAAGPWAGQV AKMAGIGKG- -TGLLAVPVP IQPRKRDVFV PFIIDPSTGV FCRQTDSGQT FLVGRTPSKE 407

H17        EEP--DPANL EVDHDFFQDK VWPHLALRVP AFETLKVQSA WAGYYDYNTF DQNGVGPHP LVVNMYFATG FSGHGLQQAP 446
Z77667     EDAKRDHSNL DVDYDDFYQK IWPVLVDRVP GFQTAKVKSA WSGYQDINTF DDAPVIGEHP LYTNLHMMCG FGERGVMHSM 487

H17        GIGRAVAEMV LKGRFQTIDL SPFLFTRFYL GEKIQE 482
Z77667     AAARAYAERI FDGAYINVNL RKFDMRRIVK MDPITE 523
```

DIFFERENTIALLY EXPRESSED GENES ASSOCIATED WITH HER-2/NEU OVEREXPRESSION

This application claims the benefit of United States provisional patent application serial No. 60/157,923, filed Oct. 6, 1999. The entire content of this provisional patent application is incorporated herein by reference.

The invention disclosed herein was made in part with Government support under Grant DAMD 17-94-J-4234 awarded by the Department of Defense and PO1 CA32737 awarded by the National Institutes of Health. The Government may have certain rights to the invention.

FIELD OF THE INVENTION

This invention relates to nucleic acid and amino acid sequences of new genes that are differentially expressed in cells that overexpress the Her-2/neu oncogene.

BACKGROUND OF THE INVENTION

Cancers of the breast and ovary are among the leading causes of death among women. The cumulative lifetime risk of a woman developing breast cancer estimated to be 1 in 9. Consequently, understanding the origins of these malignancies as well as models for the identification of new diagnostic and therapeutic modalities is of significant interest to health care professionals. In this context, cancer cells have been shown to exhibit unique gene expression, and dozens of cancer-specific genetic markers, tumor antigens, have been identified.

The human HER-2/neu (c-erbB-2) proto-oncogene encodes a transmembrane receptor tyrosine kinase with extensive sequence homology to the epidermal growth factor receptor (EGFR) (Bargmann, C. I., Hung, M. C. and Weinberg, R. A. (1986) Cell, 45(5), 649–57). Amplification and/or overexpression of HER-2/neu has been found in one-third of human breast and one-fifth of ovarian cancers (Slamon, D. J., Clark, G. M., Wong, S. G., Levin, W. J., Ullrich, A. and McGuire, W. L. (1987) Science, 235(4785), 177–82Slamon, D. J., Godolphin, W., Jones, L. A., Holt, J. A., Wong, S. G., Keith, D. E., Levin, W. J., Stuart, S. G., Udove, J., Ullrich, A. and et al. (1989) Science, 244(4905), 707–12). In addition, the HER-2/neu alteration is associated with a poor clinical outcome in that women whose tumors contain it experience earlier disease relapse and shorter overall survival (Slamon, D. J., Godolphin, W., Jones, L. A., Holt, J. A., Wong, S. G., Keith, D. E., Levin, W. J., Stuart, S. G., Udove, J., Ullrich, A. and et al. (1989) Science, 244(4905), 707–12; O'Reilly, S. M., Barnes, D. M., Camplejohn, R. S., Bartkova, J., Gregory, W. M. and Richards, M. A. (1991) Br J Cancer, 63(3), 444–6; Press, M. F., Pike, M. C., Chazin, V. R., Hung, G., Udove, J. A., Markowicz, M., Danyluk, J., Godolphin, W., Sliwkowski, M., Akita, R. and et al. (1993) Cancer Res, 53(20), 4960–70; Seshadri, R., Horsfall, D. J., Firgaira, F., McCaul, K., Sedur, V., Chalmers, A. H., Yeo, R., Ingram, D., Dawkins, H. and Hahnel, R. (1994) Int J Cancer, 56(1), 61–5). Two hypotheses potentially account for this prognostic association. First, HER-2/neu overexpression may be an epiphenomenon serving merely as a marker of aggressive breast cancers. Conversely, the alteration may be causal for the aggressive phenotype. Considerable circumstantial evidence now supports the latter possibility, with data suggesting that overexpression plays a direct causal role in the pathogenesis of the malignancies in which it occurs (Shih, C., Padhy, L. C., Murray, M. and Weinberg, R. A. (1981) Nature, 290(5803), 261–4; Di Fiore, P. P., Pierce, J. H., Kraus, M. H., Segatto, O., King, C. R. and Aaronson, S. A. (1987) Science, 237 (4811), 178–82; Hudziak, R. M., Schlessinger, J. and Ullrich, A. (1987) Proc Natl Acad Sci USA, 84(20), 7159–63).

The subtraction cloning technique termed differential hybridization, also known as plus/minus screening (St John, T. P. and Davis, R. W. (1979) Cell, 16(2), 443–52), can be used to isolate genes which are differentially expressed in cells which overexpress HER-2 as compared to control cells. This approach has the advantage of comparing two human breast cancer cell lines which are identical except for HER-2/neu overexpression allowing for a direct comparison of cDNAs derived from the two cell populations. As disclosed herein, using this approach, we identified a series of genes, either previously characterized or entirely novel, whose expression levels are altered in association with HER-2/neu overexpression. The evidence suggests that these genes might be mediators of the HER-2 overexpressing phenotype since we have confirmed their differential expression not only in human ovarian cancer cell lines which overexpress HER-2 but also primary breast cancer specimens containing this alteration.

The discovery of Her-2/neu overexpression modulated proteins, and the polynucleotides which encode them satisfies a need in the art by providing new compositions which have potential in understanding and modulating disorders associated with cell proliferation.

SUMMARY OF THE INVENTION

The present invention provides new Her-2/neu overexpression modulated proteins (including proteins having both new and known amino acid sequences such as novel splice variants of known proteins) hereinafter designated HOMPS. A first HOMPS protein is designated H17. The expression of H17 increases in cells which overexpress Her-2/neu. A second HOMPS protein is designated C40. The expression of C40 decreases in cells which overexpress Her-2/neu. A third HOMPS protein is designated H41. The expression of H41 increases in cells which overexpress Her-2/neu. A fourth HOMPS protein is designated H13. The expression of H13 increases in cells which overexpress Her-2/neu. A fifth HOMPS protein is designated H14. The expression of H14 increases in cells which overexpress Her-2/neu. In addition, the present invention discloses a HOMPS related polynucleotide sequence designated H63. The expression of H63 increases in cells which overexpress Her-2/neu.

The invention provides polynucleotides corresponding or complementary to all or part of the HOMPS genes, mRNAs, and/or coding sequences, preferably in isolated form, including polynucleotides encoding HOMPS proteins and fragments thereof, DNA, RNA, DNA/RNA hybrid, and related molecules, polynucleotides or oligonucleotides complementary to the HOMPS genes or mRNA sequences or parts thereof, and polynucleotides or oligonucleotides that hybridize to the HOMPS genes, mRNAs, or to HOMPS-encoding polynucleotides. Also provided are means for isolating cDNAs and the genes encoding HOMPS. Recombinant DNA molecules containing HOMPS polynucleotides, cells transformed or transduced with such molecules, and host-vector systems for the expression of HOMPS gene products are also provided. The invention further provides HOMPS proteins and polypeptide fragments thereof. The invention further provides antibodies that bind to HOMPS proteins and polypeptide fragments thereof, including polyclonal and monoclonal antibodies, murine and other mammalian antibodies, chimeric antibodies, humanized and fully human antibodies, and antibodies labeled with a detectable marker.

Accordingly, the invention provides a substantially purified HOMPS having the amino acid sequence shown in FIG. 2, FIG. 4, FIG. 6, FIG. 9 or FIG. 11. A typical embodiment of the invention provides an isolated and substantially purified polynucleotide that encodes HOMPS. In a particular aspect, the polynucleotide is the nucleotide sequence shown in FIG. 1, FIG. 3, FIG. 5, FIG. 8 or FIG. 10. The invention also provides a polynucleotide sequence comprising the complement of the nucleotide sequences shown in FIG. 1, FIG. 3, FIG. 5, FIG. 8 or FIG. 10 or variants thereof. In addition, the invention provides polynucleotide sequences which hybridize under stringent conditions to the nucleotide sequences shown in FIG. 1, FIG. 3, FIG. 5, FIG. 8 or FIG. 10. The invention further provides nucleic acid sequences encoding fragments or the complement of the polynucleotide sequences, as well as expression vectors and host cells comprising polynucleotides that encode HOMPS.

The invention further provides methods for detecting the presence and status of HOMPS polynucleotides and proteins in various biological samples, as well as methods for identifying cells that express HOMPS. A typical embodiment of this invention provides methods for monitoring HOMPS gene products in a tissue sample having or suspected of having some form of growth disregulation such as cancer.

BRIEF DESCRIPTION OF THE FIGURES

FIG. 1 shows a nucleic acid sequence of H17 (SEQ ID NO: 1).

FIG. 2 shows an amino acid sequence of H17 (SEQ ID NO: 2).

FIG. 3 shows a nucleic acid sequence of C40 (SEQ ID NO: 3).

FIG. 4 shows an amino acid sequence of C40 (SEQ ID NO: 4).

FIG. 5 shows a nucleic acid sequence of H41 (SEQ ID NO: 5).

FIG. 6 shows an amino acid sequence of H41 (SEQ ID NO: 6).

FIG. 7 shows a nucleic acid sequence of H63 (SEQ ID NO: 7).

FIG. 8 shows an nucleic acid sequence of H13 (SEQ ID NO: 8).

FIG. 9 shows an amino acid sequence of H13 (SEQ ID NO: 9).

FIG. 10 shows a nucleic acid sequence of H14 (SEQ ID NO: 10).

FIG. 11 shows an amino acid sequence of H14 (SEQ ID NO: 11).

DESCRIPTION OF THE INVENTION

Figure 12:
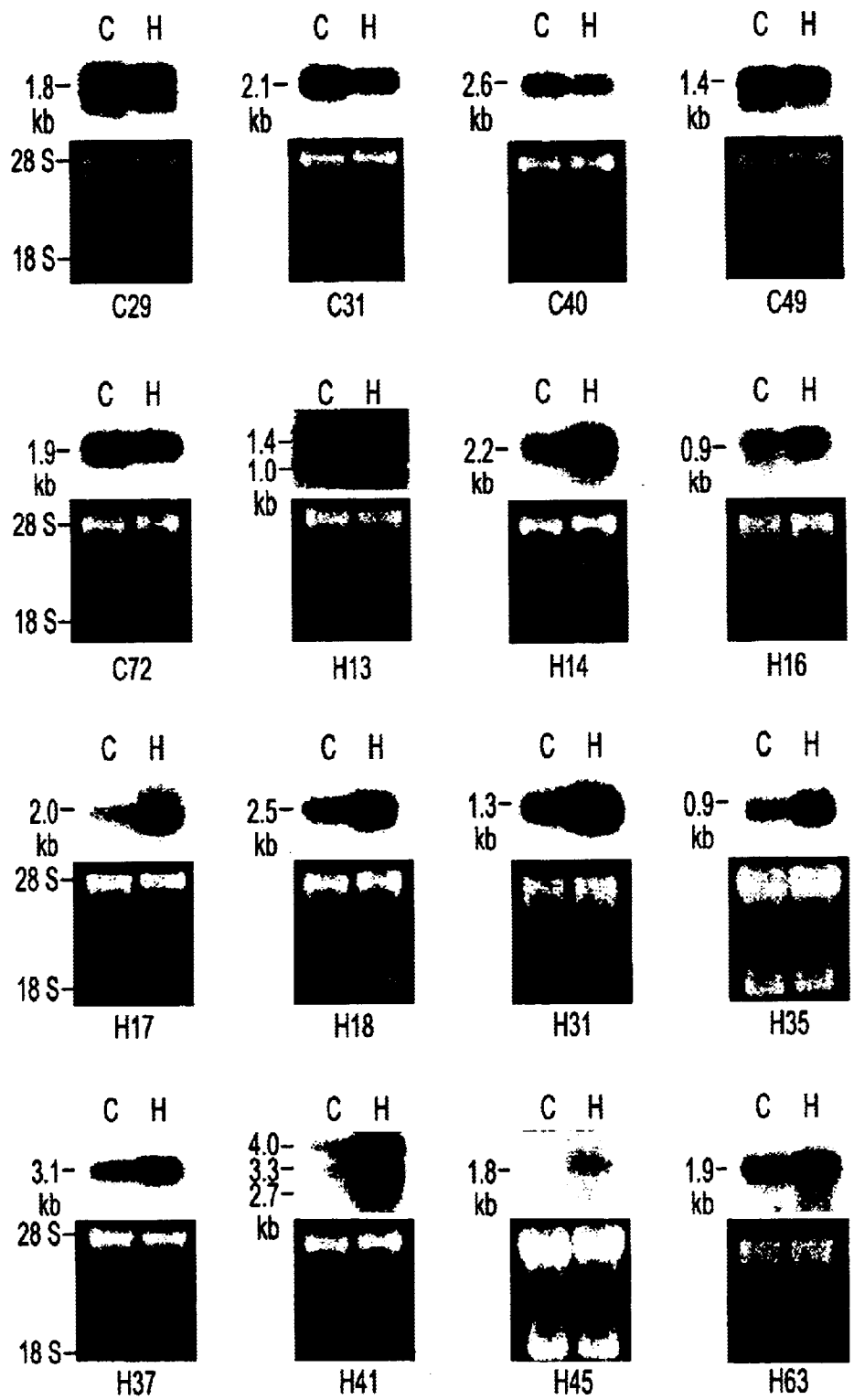
FIG. 12 shows a Northern blot analysis of candidate gene expression. Differential expression patterns were confirmed by Northern blot analyses for 5 C clones and 11 H clones. For clones H35 and H45, 20 µg of total RNA was loaded in each lane. For the remaining clones, 2 µg of poly (A) RNA was loaded (C=MCF-7/control mRNA; H=MCF-7/HER-2 mRNA.) Ethidium bromide staining of RNA gel is shown below autoradiograms to illustrate equal loading and quality of RNA. The size of the differentially expressed transcript is indicated on the left.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., 1989, Molecular Cloning: A Laboratory Manual, 2d ed., Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

In addition, a variety of art accepted definitions and methods for manipulating, evaluating and utilizing polypeptide and polynucleotide sequences are well known in the art and are widely used as a standard practice in the field of biotechnology. Such common terms and practices are provided, for example in U.S. Pat. No. 5,922,566, which is incorporated herein by reference and which recites a variety of the common terms and methodologies illustrated below.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA. As used herein, the term "polypeptide" means a polymer of at least about 6 amino acids. Throughout the specification, standard three letter or single letter designations for amino acids are used.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence", as used, herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63). HOMPS, as used herein, refers to the amino acid sequences of substantially purified HOMPS obtained from any species, particularly mammalian, including bovine, ovine, porcine, murine, equine, and preferably human, from any source whether natural, synthetic, semi-synthetic, or recombinant. "Consensus", as used herein, refers to a nucleic acid sequence which has been resequenced to resolve uncalled, bases, or which has been extended using the XL-PCR kit. (Perkin Elmer, Norwalk, Conn.) in the 5' and/or the 3' direction and resequenced, or which has been assembled from the overlapping sequences of more than one clone using the GELVIEW Fragment Assembly system (GCG, Madison, Wis.), or which has been both extended and assembled.

A "variant" of HOMPS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, LASERGENE software.

A "deletion", as used herein, refers to a change in either amino acid or nucleotide sequence in which one or more amino acid or nucleotide residues, respectively, are absent. An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HOMPS, or any oligopeptide thereof, to induce a specific immune response in appropriate animals or cells and to bind with specific antibodies.

The term "agonist", as used herein, refers to a molecule which, when bound to HOMPS, causes a change in HOMPS which modulates the activity of HOMPS. Agonists may include proteins, nucleic acids, carbohydrates, or any other molecules which bind to HOMPS.

The terms "antagonist" or "inhibitor", as used herein, refer to a molecule which, when bound to HOMPS, blocks or modulates the biological or immunological activity of HOMPS. Antagonists and inhibitors may include proteins, nucleic acids, carbohydrates, or any other molecules which bind to HOMPS.

The term "modulate", as used herein, refers to a change or an alteration in the biological activity of HOMPS. Modulation may be an increase or a decrease in protein activity, a change in binding characteristics, or any other change in the biological, functional or immunological properties of HOMPS.

The term "mimetic", as used herein, refers to a molecule, the structure of which is developed from knowledge of the structure of HOMPS or portions thereof and, as such, is able to effect some or all of the actions related to the human Her-2/neu overexpression modulated proteins.

The term "derivative", as used herein, refers to the chemical modification of a nucleic acid encoding HOMPS or the encoded HOMPS. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primner, a Laboratory Manual, Cold Spring Harbor Press, Plainview, N.Y.).

The term "hybridization", as used herein, refers to any process by which a strand of nucleic acid binds with a complementary strand through base pairing The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g. $C_{0t}$ or $R_{0t}$ analysis) or between one nucleic acid sequence present in solution and another nucleic acid sequence immobilized on a solid support (e.g. membranes filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i. e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium, citrate) and 50% formamide at 55° C., followed by a high-stringency wash consisting of 0.1×SSC containing EDTA at 55° C.

"Moderately stringent conditions" may be identified as described by Sambrook et al., 1989, Molecular Cloning: A Laboratory Manual, New York: Cold Spring Harbor Press, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., 1996, Methods in Enzymology 266:460–480; http:// blast.wustl /edu/blast/README.html). Further details regarding amino acid substitutions, which are considered conservative under such criteria, are provided below.

As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of FIG. 2, FIG. 4, FIG. 6, FIG. 9 or FIG. 11" encompasses the fill-length human HOMPS and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e. an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HOMPS or fragments thereof may comprise a cell, chromosomes isolated from a cell (e.g., a spread of metaphase chromosomes), genorric DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to FIG. 1, FIG. 3, FIG. 5, FIG. 8 or FIG. 10 by northern analysis is indicative of the presence of mRNA encoding HOMPS in a sample and thereby correlates with expression of the transcript from the polynucleotide encoding the protein. "Alterations" in the polynucleotide of FIG. 1, FIG. 3, FIG. 5, FIG. 8 or FIG. 10, as used herein, comprise any alteration in the sequence of polynucleotides encoding HOMPS including deletions, insertions, and point mutations that may be detected using hybridization assays. Included within this definition is the detection of alterations to the genomic DNA sequence which encodes HOMPS (e.g., by alterations in the pattern of restriction fragment length polymorphisms capable of hybridizing to FIG. 1, FIG. 3, FIG. 5, FIG. 8 or FIG. 10), the inability of a selected fragment of FIG. 1, FIG. 3, FIG. 5, FIG. 8 or FIG. 10 to hybridize to a sample of genomic DNA (e.g., using allele-specific oligonucleotide probes), and improper or unexpected hybridization, such as hybridization to a locus other than the normal chromosomal locus for the polynucleotide sequence encoding HOMPS (e.g., using fluorescent in situ hybridization [FISH] to metaphase chromosomes spreads).

As used herein, the term "antibody" refers to intact molecules as well as fragments thereof, such as Fab, F(ab')$_2$ and Fv, which are capable of binding the epitopic determinant. Antibodies that bind HOMPS polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

Additional definitions are provided throughout the subsections that follow.

THE INVENTION

The invention is based on the discovery of new human Her-2/neu overexpression modulated proteins (HOMPS), the polynucleotides encoding HOMPS, and the use of these compositions for the evaluation and characterization of disorders associated with abnormal cellular proliferation.

Amplification and resulting overexpression of the HER-2/neu proto-oncogene is found in approximately 30% of human breast and 20% of human ovarian cancers. To better understand the molecular events associated with overexpression of this gene in human breast cancer cells, differential hybridization was used to identify genes whose expression levels are altered in cells overexpressing this receptor. As illustrated below, of 16,000 clones screened from an overexpression cell cDNA library, a total of 19 non-redundant clones were isolated including 7 whose expression decreases (C clones) and 12 which increase (H clones) in association with HER-2/neu overexpression. Of these, 5 C clones and 11 H clones have been confirmed to be differentially expressed by Northern blot analysis. This group includes nine genes of known function, three previously sequenced genes of relatively uncharacterized function and four novel genes without match in GenBank. Examination of the previously characterized genes indicates that they represent sequences known to be frequently associated with the malignant phenotype, suggesting that the subtraction cloning strategy used identified appropriate target genes. In addition, differential expression of 12 of 16 (75%) cDNAs identified in the breast cancer cell lines are also seen in HER-2/neu overexpressing ovarian cancer cells, indicating that they represent generic associations with HER-2/neu overexpression. Finally, upregulation of two of the identified cDNAs, one novel and one identified but as yet uncharacterized gene, was confirmed in human breast cancer specimens in association with HER-2/neu overexpression. Further characterization of these genes may yield insight into the fundamental biology and pathogenetic effects of HER-2/neu overexpression in human breast and ovarian cancer cells.

To more directly evaluate the potential biologic role of HER-2/neu overexpression in the pathogenesis of breast cancer, disclosed herein is an experimental model in which the effects of overexpression in human breast cancer cells can be studied (Pietras, R. J., Fendly, B. M., Chazin, V. R., Pegram, M. D., Howell, S. B. and Slamon, D. J. (1994) Oncogene, 9(7), 1829–38; Pietras, R. J., Arboleda, J., Reese, D. M., Wongvipat, N., Pegram, M. D., Ramos, L., Gorman, C. M., Parker, M. G., Sliwkowski, M. X. and Slamon, D. J. (1995) Oncogene, 10(12), 2435–46; Pegram, M. D., Finn, R. S., Arzoo, K., Beryt, M., Pietras, R. J. and Slamon, D. J. (1997) Oncogne, 15(5), 537–47; Chazin, V. R. (1991). The biologic effects of HER-2/neu proto-oncogene overexpression, Chapter 2. Department of Microbiology and Immunology, University of California, Los Angeles). In these experiments, human MCF-7 breast cancer cells which express normal levels of the receptor were transfected with a retroviral expression vector containing a full length cDNA encoding the human HER-2 gene (Chazin, V. R., Kaleko, M., Miller, A. D. and Slamon, D. J. (1992) Oncogene, 7(9), 1859–66). Multiple rounds of infection and sorting of the top 5% of HER-2 overexpressing, pooled transfectants generated a stably transfected cell line, MCF-7/HER-2, in which HER-2 expression levels were comparable to those observed in human HER-2 overexpressing breast cancer specimens (Pegram, M. D., Finn, R. S., Arzoo, K., Beryt, M., Pietras, R. J. and Slamon, D. J. (1997) Oncogene, 15(5), 537–47). MCF-7 cells were similarly transfected using an empty neomycin resistance vector including multiple infections, producing the MCF-7/control cell line. The amount of HER-2/neu protein expressed, as determined by quantitative Western blot analysis, was approximately 1.62 pg/cell for MCF-7/HER-2 cells as compared to 0.36 pg/cell for MCF-7/control cells (Press, M. F., Pike, M. C., Chazin, V. R., Hung, G., Udove, J. A., Markowicz, M., Danyluk, J., Godolphin, W., Sliwkowski, M., Akita, R. and et al. (1993) Cancer Res, 53(20), 4960–70). In vitro and in vivo studies of these engineered cells demonstrated that the growth characteristics of the MCF-7/HER-2 human breast cancer cell line are significantly altered by the overexpression of HER-2/neu (Pietras, R. J., Fendly, B. M., Chazin, V. R., Pegram, M. D., Howell, S. B. and Slamon, D. J. (1994) Oncogene, 9(7), 1829–38; Pietras, R. J., Arboleda, J., Reese, D. M., Wongvipat, N., Pegram, M. D., Ramos, L., Gorman, C. M., Parker, M. G., Sliwkowski, M. X. and Slamon, D. J. (1995) Oncogene, 10(12), 2435–46; Pegram, M. D., Finn, R. S., Arzoo, K., Beryt, M., Pietras, R. J. and Slamon, D. J. (1997) Oncogene, 15(5), 537–47; Chazin, V. R. (1991). The biologic effects of HER-2/neu proto-oncogene overexpression, Chapter 2. Department of Microbiology and Immnunology, University of California, Los Angeles; Chazin, V. R., Kaleko, M., Miller, A. D. and Slamon, D. J. (1992) Oncogene, 7(9), 1859–66). Increased cell proliferation was seen in the HER-2 overexpressing cell line as assessed by $^3$H-thymidine incorporation and in vitro cell proliferation assays. In addition, HER-2 overexpression markedly improved soft agar cloning efficiency, and the cells exhibited increased tumorigenicity in nude mice (Chazin, V. R. (1991). The biologic effects of HER-2/neu proto-oncogene overexpression, Chapter 2. Department of Microbiology and Immunology, University of California, Los Angeles; Chazin, V. R., Kaleko, M., Miller, A. D. and Slamon, D. J. (1992) Oncogene, 7(9), 1859–66). Together, the data confirmed that overexpression of the HER-2 receptor tyrosine kinase plays a role in altering the biologic behavior of human breast cancer cells. The exact molecular mechanism(s) by which this overexpression promotes a more aggressive phenotype of these cells, however, remains unknown. There are multiple potential mechanisms by which the observed phenotypic changes may occur. Increased amounts and/or activation of this cell surface receptor may affect either the expression or function of other molecules involved in regulation of cell proliferation. Direct effects of HER-2 overexpression on other cellular proteins can be accomplished by changes in 1) expression at the mRNA transcript level, 2) protein production at the translational level, or 3) protein activation/modification at the post-translational level. The cellular changes associated with HER-2/neu overexpression are likely to be induced by most or all of these mechanisms. To identify those changes associated with differential expression of genes at the transcript level, we undertook a differential screening analysis.

The subtraction cloning technique termed differential hybridization, also known as plus/minus screening (St John, T. P. and Davis, R. W. (1979) *Cell*, 16(2), 443–52), was used to isolate genes which are differentially expressed in MCF-7/HER-2 cells as compared to MCF-7/control cells. This approach has the advantage of comparing two human breast cancer cell lines which are identical except for HER-2/neu overexpression allowing for a direct comparison of cDNAs derived from the two cell populations. In the current study, we identified a series of genes, either previously characterized or entirely novel, whose expression levels are altered in association with HER-2/neu overexpression. It is possible that some of these genes might be mediators of the HER-2 overexpressing phenotype since we have confirmed their differential expression not only in human ovarian cancer cell lines which overexpress HER-2 but also primary breast cancer specimens containing this alteration.

The differential screening approach compared MCF-7 breast cancer cell lines transfected with a human HER-2/neu cDNA (MCF-7/HER-2) or with an identical empty vector (MCF-7/control). The alternative approach of comparing two different non-engineered cell lines which are not isogenic i.e. MCF-7 and/or MDA-MB-231 compared against SKBR3 and/or BT-474, respectively, is problematic in that the presence of non-HER-2 associated genetic differences unique to cells derived from different individuals would almost certainly complicate interpretation of results. Such heterogenetic effects would confound identification of those genes which are differentially expressed in direct association with HER-2/neu overexpression. A relatively conventional subtraction cloning method termed differential hybridization has been successfully used by other investigators in the cloning of genes associated with various biologic phenomenon including the galactose-inducible genes of yeast (St John, T. P. and Davis, R. W. (1979) *Cell*, 16(2), 443–52), human fibroblast interferon (Taniguchi, T., Fujii-Kuriyama, Y. and Muramatsu, M. (1980) *Proc Natl Acad Sci USA*, 77(7), 4003–6), a variety of heat-shock proteins (Mason, I. J., Taylor, A., Williams, J. G., Sage, H. and Hogan, B. L. (1986) *Embo J*, 5(7), 1465–72), and the metastasis suppressor gene nm-23 (Steeg, P. S., Bevilacqua, G., Kopper, L., Thorgeirsson, U. P., Talmadge, J. E., Liotta, L. A. and Sobel, M. E. (1988) *J Natl Cancer Inst*, 80(3), 200–4). This screening strategy has the advantage of obtaining a high yield of full-length clones in contrast to more recent techniques such as differential display or representational difference analysis (RDA) which require an additional procedure of screening a cDNA library using the DNA fragments obtained.

From our initial screen of 16,000 MCF-7/HER-2 cDNA library clones, we identified five genes with decreased and eleven genes with increased expression levels in association with HER-2/neu overexpression. These clones include nine genes with previously identified cellular functions, three existing sequences of relatively uncharacterized function, and four novel genes without matching sequences in GenBank. A number of the known genes identified in our screening have been previously reported to be associated with several aspects of human breast cancer and/or tumorigenicity in general. Although the differential screening approach does not provide direct evidence that a given gene plays a critical role in the phenotypic changes associated with HER-2 overexpression, a review of the literature regarding some of the genes in our study indicates that they may be candidates. Recent data, for example, indicates that downregulation of cytokeratin (C29, C49) gene expression may result in disorganization of the cytoskeleton leading to enhanced invasive properties (Mukhopadhyay, T. and Roth, J. A. (1996) *Anticancer Res*, 16(1), 105–12). Similarly, the gamma actin (C72) transcript level is markedly decreased in salivary gland adenocarcinoma cells on acquisition of metastatic ability (Suzuki, H., Nagata, H., Shimada, Y. and Konno, A. (1998) *Int J Oncol*, 12(5), 1079–84). These observations are consistent with our findings and are of interest given the fact that HER-2 overexpression is associated with increased metastatic potential (Kennedy, M. J. (1996) *Curr Opin Oncol*, 8(6), 485–90; Pantel, K., Schlimok, G., Braun, S., Kutter, D., Lindemann, F., Schaller, G., Funke, I., Izbicki, J. R. and Riethmuller, G. (1993) *J Natl Cancer Inst*, 85(17), 1419–24; Kallioniemi, O. P., Holli, K., Visakorpi, T., Koivula, T., Helin, H. H. and Isola, J. J. (1991) *Int J Cancer*, 49(5), 650–5). The observation that Cathepsin D (C31) transcript level is decreased in HER-2 overexpressing breast cancer cells is consistent with the most recent clinical data Johnson, M. D., Torri, J. A., Lippman, M. E. and Dickson, R. B. (1993) *Cancer Res*, 53(4), 873–7; Ravdin, P. M., Tandon, A. K., Allred, D. C., Clark, G. M., Fuqua, S. A., Hilsenbeck, S. H., Chamness, G. C. and Osborne, C. K. (1994) *J Clin Oncol*, 12(3), 467–74) which contradict the original reports of high Cathepsin D concentrations as indicative of a poorer prognosis (Thorpe, S. M., Rochefort, H., Garcia, M., Freiss, G., Christensen, I. J., Khalaf, S., Paolucci, F., Pau, B., Rasmussen, B. B. and Rose, C. (1989) *Cancer Res*, 49(21), 6008–14). The 90 kDa heat shock protein (H18) forms highly stable complexes with the estrogen receptor and thus may play a role in mediating estrogen-dependent growth (Ramachandran, C., Catelli, M. G., Schneider, W. and Shyamala, G. (1988) *Endocrinology*, 123(2), 956–61; Shyamala, G., Gauthier, Y., Moore, S. K., Catelli, M. G. and Ullrich, S. J. (1989) *Mol Cell Biol*, 9(8), 3567–70). Its potential role in regulating estrogen receptor activity in human breast cancer is interesting in light of the interactions recently described between HER-2 and the estrogen receptor (Carlomagno, C., Perrone, F., Gallo, C., De Laurentiis, M., Lauria, R., Morabito, A., Pettinato, G., Panico, L., D'Antoruo, A., Bianco, A. R. and De Placido, S. (1996) *J Clin Oncol*, 14(10), 2702–8; Ignar-Trowbridge, D. M., Nelson, K. G., Bidwell, M. C., Curtis, S. W., Washburn, T. F., McLachlan, J. A. and Korach, K. S. (1992) *Proc Natl Acad Sci USA*, 89(10), 4658–62). Other known genes found in our screening to be overexpressed in association with HER-2 overexpression, ribosomal proteins L8 (H16) and LLrep3(H35), GAPDH (H31), and succinyl coA transferase (H45), may be merely reflective of higher proliferation in HER-2 overexpressing tumors. Alternatively, differential expression of these genes may be more specifically linked to HER-2 overexpression. An example of this could be the LLrep3 which was also identified in differential hybridization screening of a ras-transfected teratocarcinoma cell line compared to isogenic cell control as increased 25-fold (Chiao, P. J., Shin, D. M., Sacks, P. G., Hong, W. K. and Tainsky, M. A. (1992) *Mol Carcinog*, 5(3), 219–31), however, this gene is not differentially expressed when comparing nontumorigenic and tumorigenic NIH 3T3 cells transformed by Ha-ras, N-ras, v-myc, v-mos, v-src and v-abl (Chiao, P. J., Shin, D. M., Sacks, P. G., Hong, W. K. and Tainsky, M. A. (1992) *Mol Carcinog*, 5(3), 219–31).

DNA fragmentation factor (DFF) (H13) is also overexpressed in the HER-2 overexpressing cells and has recently been identified as a protein which functions downstream of caspase-3 during apoptosis (Liu, X., Zou, H., Slaughter, C. and Wang, X. (1997) *Cell*, 89(2), 175–84). Its exact cellular role in this process, i.e. inhibition or promotion of apoptosis, however, is as yet undefined (Mitamura, S., Ikawa, H., Mizuno, N., Kaziro, Y. and Itoh, H. (1998) *Biochem Biophys Res Commun*, 243(2), 480–4; Inohara, N., Koseki, T., Chen, S., Wu, X. and Nunez, G. (1998) *Embo J*, 17(9), 2526–33; Granville, D. J., Jiang, H., An, M. T., Levy, J. G., McManus, B. M. and Hunt, D. W. (1998) *FEBS Lett*, 422(2), 151–4). Lastly, DRP-1 (Density regulated protein-1) (H14), which is also increased in association with HER-2 overexpression has been found to be preferentially expressed in cells grown at high density compared to cells at low density. Growth arrest by serum starvation or transforming growth factor B treatment does not however induce this gene's expression (Deyo, J. E., Chiao, P. J. and Tainsky, M. A. (1998) *DNA Cell Biol*, 17(5), 437–47). Its role, if any, in the HER-2 phenotype remains to be determined.

The possibility that the pattern of differential gene expression observed in this study is unique to a given experimental cell line rather than a generic phenomenon associated with HER-2 overexpression was also addressed. To verify differential expression in another cell line, we utilized CaOv-3 ovarian cancer cells engineered to overexpress HER-2/neu. For 75% of the differentially expressed clones, the patterns identified in the breast cancer cells were also found in the human ovarian cancer cell counterparts. This consistent expression pattern, demonstrated across cell lines from two different epithelia (i.e. breast and ovary), suggest that the expression differences observed in our study are related to HER-2/neu overexpression. In addition, we found a correlation between overexpression of HER-2/neu and upregulation of the H37 and H41 genes in actual human breast cancer specimens. Those genes which did not yield a signal on Northern analysis likely due to rare message level are currently being evaluated by a quantitative RT-PCR approach to circumvent this difficulty. Given the problem in assessing Northern blot analyses from whole tissue specimens resulting from dilutional artifacts introduced by surrounding normal cells, these correlations are encouraging. It is intriguing that the H37 cDNA, found to be overexpressed in HER-2 overexpressing cells in the current study and demonstrating convincing differential expression in actual tumor samples, is localized to a region of chromosome 3p21.3 alleged to contain a putative lung cancer tumor suppressor gene(s) (Wei, M. H., Latif, F., Bader, S., Kashuba, V., Chen, J. Y., Duh, F. M., Sekido, Y., Lee, C. C., Geil, L., Kuzmin, I., Zabarovsky, E., Klein, G., Zbar, B., Nlinna, J. D. and Lerman, M. I. (1996) *Cancer Res*, 56(7), 1487–92). Further characterization of this gene at the functional and genomic levels should give further insight into this phenomenon.

The current studies indicate that HER-2/neu overexpression induces a pattern of consistent genetic alterations in target human cells. We recognize that there are more sensitive techniques such as microarray chip technology now available for evaluating differential gene expression and plan to reanalyze these cell line pairs using these newer approaches. It is possible that some of the genes identified may in part be biologic mediators of the aggressive biologic behavior associated with HER-2/neu overexpression. Future elucidation of role of these genes, in particular those with as yet unknown function, in mediating malignant phenotype should provide further insights into the fundamental biology and pathogenetic effects of HER-2/neu overexpression in human breast and ovarian cancer cells and suggests novel treatment strategies for patients whose tumors contain these alterations.

USES FOR HOMPS GENES AND GENE PRODUCTS DESCRIBED HEREIN

Skilled artisans understand both the great diagnostic value that known oncogenesis associated markers such as Her-2 and PSA provide in the monitoring of cancers in patients as well as the need for the identification of additional oncogenesis associated markers (see e.g. Bostwick et al., J Cell Biochem Suppl 1996;25:156–64 and Morote et al., Int J Cancer 1999 August 20;84(4):421–5). In particular, artisans understand that oncogenesis is a multistep process and the identification of a variety of different oncogenesis associated markers can be used to identify and characterize precancerous and cancerous syndromes earlier and more efficiently (see e.g. Rhim et al., Cancer Res 1990 September 1;50(17 Suppl):5653S-5657). In this context, the specific properties of the HOMPS proteins described herein (e.g. their modulation by a Her-2, an oncogene which plays a role significant role in a number of human cancers including breast cancer) includes them in the class of oncogenesis associated markers that can be used to evaluate and/or evaluate oncogenetic processes in cancers. Understandably, a number of the HOMPS proteins disclosed herein have been independently identified by other artisans as oncogenesis associated markers which can be used to examine growth disregulation in conditions such as cancer (see e.g. Yano et al., Jpn J Cancer Res 1996 September;87(9):908–15 [hsp90]; Chou et al., Proc Natl Acad USA 1987 May;84(9):2575–9 [gamma actin] and Tonkin et al., Cancer Prev Control 1999 April; 3(2):131–6 [cathepsin-D]).

As disclosed herein, HOMPS gene products exhibit specific properties that are analogous to those found in a family of genes whose polynucleotides, polypeptides and anti-polypeptide antibodies are used in well known diagnostic assays directed to examining conditions associated with disregulated cell growth such as cancer. Well known members of this class include Her-2 as well as PSA, the archetypal markers that have been used by medical practitioners for years to identify and monitor the presence of cancers such as prostate cancer (see e.g. Merrill et al., J. Urol. 163(2): 503–5120 (2000); Polascik et al., J. Urol. August;162(2):293–306 (1999) and Fortier et al., J. Nat. Cancer Inst. 91(19): 1635–1640(1999)). A variety of other diagnostic markers are also used in this context including $p5^3$ and K-ras (see e.g. Tulchinsky et al., Int J Mol Med 1999 July;4(1):99–102 and Minimoto et al., Cancer Detect Prev 2000;24(1):1–12). Consequently, this disclosure of the HOMPS polynucleotides and polypeptides (as well as the HOMPS polynucleotide probes and anti-HOMPS antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the HOMPS polynucleotides, polypeptides and antibodies described herein are analogous to those methods from well established diagnostic assays which employ Her-2 and PSA polynucleotides, polypeptides and antibodies. For example, just as PSA polynucleotides are used as probes (for example in Northern analysis, see e.g. Sharief et al., Biochem. Mol. Biol. Int. 33(3):567–74(1994)) and primers (for example in PCR analysis, see e.g. Okegawa et al., J. Urol. 163(4): 1189–1190 (2000)) to observe the presence and/or the level of PSA Mrs. in methods of monitoring PSA overexpression or the metastasis of prostate cancers, the HOMPS polynucleotides described herein can be utilized in the same way to evaluate or monitor the cellular growth disregulation that is associated with cancer. Alternatively, just as PSA polypeptides are used to generate antibodies specific for PSA which can then be used to observe the presence and/or the level of PSA proteins in methods of monitoring PSA protein overexpression (see e.g. Stephan et al., Urology 55(4):560–3 (2000)) or the metastasis of prostate cells (see e.g. Alanen et al., Pathol. Res. Pract. 192(3):233–7 (1996)), the HOMPS polypeptides described herein can be utilized to generate antibodies for use in detecting HOMPS overexpression as seen in cells expected of exhibiting some form of growth disregulation.

Just as Her-2 and PSA polynucleotide fragments and polynucleotide variants are employed by skilled artisans for use in methods of monitoring this molecule, HOMPS polynucleotide fragments and polynucleotide variants can also be used in an analogous manner. In particular, typical PSA polynucleotides used in methods of monitoring this molecule are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see e.g. Caetano-Anolles, G. Biotechniques 25(3): 472–476, 478–480 (1998); Robertson et al., Methods Mol. Biol. 98:121–154 (1998)). In addition, in order to facilitate their use by medical practitioners, variant polynucleotide sequences are typically used as primers and probes for the corresponding mRNAs. in PCR and Northern analyses (see e.g. Sawai et al., Fetal Diagn. Ther. 1996 November-December;11(6):407–13 and Current Protocols In Molecular Biology, Volume 2, Unit 2, Frederick M. Ausubul et al. eds., 1995)). Polynucleotide fragments and variants are typically useful in this context as long as they have the common attribute or characteristic of being capable of binding to a target polynucleotide sequence (e.g. the HOMPS polynucleotide shown in FIG. 2) under conditions of high stringency.

Just as Her-2 and PSA polypeptide fragments and polypeptide variants are employed by skilled artisans for use in methods of monitoring this molecule, HOMPS polypeptide fragments and polypeptide variants can also be used in an analogous manner. In particular, typical PSA polypeptides used in methods of monitoring this molecule are fragments of the PSA protein which contain an epitope that can be recognized by an antibody which will specifically bind to the PSA protein. This practice of using polypeptide fragments or polypeptide variants used to generate antibodies (such as anti-PSA antibodies) is typical in the art with a wide variety of systems such as fusion proteins being used by practitioners (see e.g. Current Protocols In Molecular Biology, Volume 2, Unit 16, Frederick M. Ausubul et al. eds., 1995). In this context, each of the variety of epitopes in a protein of interest functions to provide the architecture upon which the antibody is generated. Typically, skilled artisans generally create a variety of different polypeptide fragments that can be used in order to generate antibodies specific for different portions of a polypeptide of interest (see e.g. U.S. Pat. No. 5,840,501 and U.S. Pat. No. 5,939,533). For example it may be preferable to utilize a polypeptide comprising one of the HOMPS biological motifs discussed below. Polypeptide fragments and variants are typically useful in this context as long as they have the common attribute or characteristic of having an epitope capable of generating an antibody specific for a target polypeptide sequence (e.g. the HOMPS polypeptide shown in FIG. 2).

As shown herein, the HOMPS polynucleotides and polypeptides (as well as the HOMPS polynucleotide probes and anti-HOMPS antibodies used to identify the presence of these molecules) exhibit specific properties that can make them useful in examining cancerous cells or tissues. The described diagnostic assays that measures the presence of HOMPS gene products, in order to provide evidence of growth disregulation are particularly useful in identifying potential candidates for preventive measures or further monitoring, as has been done so successfully with Her-2 and PSA (see e.g. Scheurle et al., Anticancer Res. 2000 May-June;20(3B):2091–6; Fontana et al., Anticancer Res 1994 September-October;14(5B):2099–104 and Sahin, Adv Anat Pathol 2000 May;7(3):158–66).

HOMPS EMBODIMENTS

As disclosed herein, the invention is directed to Her-2/neu overexpression modulated proteins (HOMPS) genes and HOMPS gene products as well as HOMPS antibodies and assays for detecting these molecules. Typically, the invention encompasses HOMPS proteins as well as the polynucleotides which encode HOMPS proteins. Accordingly, any nucleic acid sequence which encodes the amino acid sequence of HOMPS can be used to generate recombinant molecules which express HOMPS. In a particular embodiment, the invention encompasses the polynucleotide comprising the nucleic acid sequence of FIG. 1, FIG. 3, FIG. 5, FIG. 8 or FIG. 10, the invention encompasses HOMPS variants which retain biological or other functional activity of HOMPS. A preferred HOMPS variant is one having at least 80%, and more preferably 90%, amino acid sequence identity to the HOMPS amino acid sequence of FIG. 2, FIG. 4, FIG. 6, FIG. 9 or FIG. 11. A most preferred HOMPS variant is one having at least 95% amino acid sequence identity to the amino acid sequence of FIG. 2, FIG. 4, FIG. 6, FIG. 9 or FIG. 11.

It will be appreciated by those skilled in the art that as a result of the degeneracy of the genetic code, a multitude of nucleotide sequences encoding HOMPS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HOMPS, and all such variations are to be considered as being specifically disclosed.

Although nucleotide sequences which encode HOMPS and its variants are preferably capable of hybridizing to the nucleotide sequence of the naturally occurring HOMPS under appropriately selected conditions of stringency, it may be advantageous to produce nucleotide sequences encoding HOMPS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HOMPS and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HOMPS and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HOMPS or any portion thereof.

Also encompassed by the invention are polynucleotide sequences that are capable of hybridizing to the claimed nucleotide sequences, and in particular, those shown in FIG. 1, FIG. 3, FIG. 5, FIG. 8 or FIG. 10, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding HOMPS which are encompassed by the invention include deletions, insertions, or substitutions of different nucleotides resulting in a polynucleotide that encodes the same or a functionally equivalent HOMPS. The encoded protein may also contain deletions, insertions, or substitutions of amino acid residues which produce a silent change and result in a functionally equivalent HOMPS. Deliberate amino acid substitutions may be made on the basis of similarity in polarity, charge, solubility, hydrophobicity, hydrophilicity, and/or the amphipathic nature of the residues as long as the biological activity of HOMPS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

As discussed above, the invention is directed to Her-2/neu overexpression modulated proteins (HOMPS). The typical embodiments of the invention discussed herein (e.g. polynucleotides, polypeptides, antibodies and assays for HOMPS gene products etc.) are directed to all of the HOMPS genes and gene products (i.e. H13, H14, H17, H41, H63 and C40). In descriptions of the invention provided herein, embodiments of a single HOMPS gene are used (for example the H41 gene) to illustrate typical embodiments of the invention that apply to all of the HOMPS molecules provided herein. In this context, artisans understand that the use of a single HOMPS molecule in illustrative typical embodiments common to all of the HOMPS molecules eliminates unnecessary redundancy in the description of the invention.

One aspect of the invention provides polynucleotides corresponding or complementary to all or part of a HOMPS gene, mRNA, and/or coding sequence, preferably in isolated form, including polynucleotides encoding a HOMPS protein and fragments thereof, DNA, RNA, DNA/RNA hybrid, and related molecules, polynucleotides or oligonucleotides complementary to a HOMPS gene or mRNA sequence or a part thereof, and polynucleotides or oligonucleotides that hybridize to a HOMPS gene, mRNA, or to a HOMPS encoding polynucleotide (collectively, "HOMPS polynucleotides"). As used herein, the HOMPS gene and protein is meant to include the HOMPS genes and proteins specifically described herein.

One illustrative embodiment of a typical HOMPS polynucleotide is a polynucleotide having the H41 sequence shown in FIG. 5 (SEQ ID NO: 5). A H41 polynucleotide may comprise a polynucleotide having the nucleotide sequence of human H41 as shown in FIG. 5 (SEQ ID NO: 5), wherein T can also be U; a polynucleotide that encodes all or part of the H41 protein; a sequence complementary to the foregoing; or a polynucleotide fragment of any of the foregoing. Another embodiment comprises a polynucleotide that is capable of hybridizing under stringent hybridization conditions to the human H41 cDNA shown in FIG. 5 (SEQ ID NO: 5) or to a polynucleotide fragment thereof.

Typical embodiments of the invention disclosed herein include H41 polynucleotides containing specific portions of the H41 mRNA sequence (and those which are complementary to such sequences) such as those that encode the protein and fragments thereof. For example, representative embodiments of the invention disclosed herein include: polynucleotides encoding about amino acid 1 to about amino acid 10 of the H41 protein shown in FIG. 5 (SEQ ID NO: 5), polynucleotides encoding about amino acid 20 to about amino acid 30 of the H41 protein shown in FIG. 5 (SEQ ID NO: 5), polynucleotides encoding about amino acid 30 to about amino acid 40 of the H41 protein shown in FIG. 5 (SEQ ID NO: 5), polynucleotides encoding about amino acid 40 to about amino acid 50 of the H41 protein shown in FIG. 5 (SEQ ID NO: 5), polynucleotides encoding about amino acid 50 to about amino acid 60 of the H41 protein shown in FIG. 5 (SEQ ID NO: 5), polynucleotides encoding about amino acid 60 to about amino acid 70 of the H41 protein shown in FIG. 5 (SEQ ID NO: 5), polynucleotides encoding about amino acid 70 to about amino acid 80 of the H41 protein shown in FIG. 5 (SEQ ID NO: 5), polynucleotides encoding about amino acid 80 to about amino acid 90 of the H41 protein shown in FIG. 5 (SEQ ID NO: 5) and polynucleotides encoding about amino acid 90 to about amino acid 100 of the H41 protein shown in FIG. 5 (SEQ ID NO: 5), etc. Following this scheme, polynucleotides encoding portions of the amino acid sequence of amino acids 100–258 of the H41 protein are typical embodiments of the invention. Polynucleotides encoding larger portions of the H41 protein are also contemplated. For example polynucleotides encoding from about amino acid 1 (or 20 or 30 or 40 etc. to about amino acid 20, (or 30, or 40 or 50 etc.) of the H41 protein shown in FIG. 5 (SEQ ID NO: 5) may be generated by a variety of techniques well known in the art.

Additional illustrative embodiments of H41 polynucleotides include embodiments consisting of a polynucleotide having the sequence as shown in FIG. 5 (SEQ ID NO: 5) from about nucleotide residue number 1 through about nucleotide residue number 500, from about nucleotide residue number 500 through about nucleotide residue number 1000 and from about nucleotide residue number 500 through about nucleotide residue number 1000 and from about nucleotide residue number 1000 through about nucleotide residue number 1500 and from about nucleotide residue number 1500 through about nucleotide residue number 2000 and from about nucleotide residue number 2000 through about nucleotide residue number 2500 and from about nucleotide residue number 2500 through about nucleotide residue number 3000 and from about nucleotide residue number 3000 through about nucleotide residue number 3346. These polynucleotide fragments can be of any size an include any portion of the H41 sequence as shown in FIG. 5 (SEQ ID NO: 5), for example a polynucleotide having the sequence as shown in FIG. 5 (SEQ ID NO: 5) from about nucleotide residue number 324 through about nucleotide residue number 2248.

Another aspect of the present invention provides H41 proteins and polypeptide fragments thereof. The H41 proteins of the invention include those specifically identified herein, as well as allelic variants, conservative substitution variants and homologs that can be isolated/generated and characterized without undue experimentation following the methods outlined below. Fusion proteins that combine parts of different H41 proteins or fragments thereof, as well as fusion proteins of a H41 protein and a heterologous polypeptide are also included. Such H41 proteins will be collectively referred to as the H41 proteins, the proteins of the invention, or H41. As used herein, the term "H41 polypeptide" refers to a polypeptide fragment or a H41 protein of at least 6 amino acids, preferably at least 15 amino acids.

Specific embodiments of H41 proteins comprise a polypeptide having the amino acid sequence of human H41 as shown in FIG. 6 (SEQ ID NO: 6). Alternatively, embodiments of H41 proteins comprise variant polypeptides having alterations in the amino acid sequence of human H41 as shown in FIG. 6 (SEQ ID NO: 6).

In general, naturally occurring allelic variants of human HOMPS such as H41 will share a high degree of structural identity and homology (e.g., 90% or more identity). Typically, allelic variants of the HOMPS proteins will contain conservative amino acid substitutions within the HOMPS sequences described herein or will contain a substitution of an amino acid from a corresponding position in a HOMPS homologue. One class of HOMPS allelic variants will be proteins that share a high degree of homology with at least a small region of a particular HOMPS amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of HOMPS proteins such as polypeptides having amino acid insertions, deletions and substitutions. HOMPS variants can be made using methods known in the art such as site-directed mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (wells et al., 1985, Gene 34:315), restriction selection mutagenesis (Wells et al., 1986, Philos. Trans. R. Soc. London Ser. A, 317:415) or other known techniques can be performed on the cloned DNA to produce the HOMPS variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W. H. Freeman & Co., New York.); Chothia, 1976, J. Mol. Biol., 150:1). If alanine substitution does not yield adequate amounts of variant, an isostetic amino acid can be used.

As defined herein, HOMPS variants have the distinguishing attribute of having at least one epitope in common with a HOMPS protein (such as the H41 protein having the amino acid sequence of FIG. 6 (SEQ ID NO: 6)), such that an antibody that specifically binds to a HOMPS variant will also specifically bind to the HOMPS protein (such as the HOMPS protein having the amino acid sequence of FIG. 6 (SEQ ID NO: 6)). Using H41 as an illustrative example, a polypeptide ceases to be a variant of the H41 protein shown in FIG. 6 (SEQ ID NO: 6) when it no longer contains an epitope capable of being recognized by an antibody that specifically binds to a H41 HOMPS protein. Those skilled in the art understand that antibodies that recognize proteins bind to epitopes of varying size, and a grouping of the order of about six amino acids, contiguous or not, is regarded as a typical number of amino acids in a mammal epitope. See e.g. Hebbes et al., Mol Immunol (1989) 26(9):865–73; Schwartz et al., J Immunol (1985) 135(4):2598–608. As there are approximately 20 amino acids that can be included at a given position within the minimal 6 amino acid epitope, the odds of such an epitope occurring by chance are about $20^6$ or about 1 in 64 million. Another specific class of HOMPS protein variants shares 90% or more identity with the amino acid sequence of FIG. 6 (SEQ ID NO: 6).

As discussed above, embodiments of the claimed invention include polypeptides containing less than the 258 amino acid sequence of the H41 protein shown in FIG. 6 (SEQ ID NO: 6) (and the polynucleotides encoding such polypeptides). For example, representative embodiments of the invention disclosed herein include polypeptides consisting of about amino acid 1 to about amino acid 10 of the H41 protein shown in FIG. 6 (SEQ ID NO: 6), polypeptides consisting of about amino acid 20 to about amino acid 30 of the H41 protein shown in FIG. 6 (SEQ ID NO: 6), polypeptides consisting of about amino acid 30 to about amino acid 40 of the H41 protein shown in FIG. 6 (SEQ ID NO: 6), polypeptides consisting of about amino acid 40 to about amino acid 50 of the H41 protein shown in FIG. 6 (SEQ ID NO: 6), polypeptides consisting of about amino acid 50 to about amino acid 60 of the H41 protein shown in FIG. 6 (SEQ ID NO: 6), polypeptides consisting of about amino acid 60 to about amino acid 70 of the H41 protein shown in FIG. 6 (SEQ ID NO: 6), polypeptides consisting of about amino acid 70 to about amino acid 80 of the H41 protein shown in FIG. 6 (SEQ ID NO: 6), polypeptides consisting of about amino acid 80 to about amino acid 90 of the H41 protein. shown in FIG. 6 (SEQ ID NO: 6) and polypeptides consisting of about amino acid 90 to about amino acid 100 of the H41 protein shown in FIG. 6 (SEQ ID NO: 6), etc. Following this scheme, polypeptides consisting of portions of the amino acid sequence of amino acids 100–258 of the H41 protein are typical embodiments of the invention. Polypeptides consisting of larger portions of the H41 protein are also contemplated. For example polypeptides consisting of about amino acid 1 (or 20 or 30 or 46 etc.) to about amino acid 20, (or 30, or 40 or 50 etc.) of the H41 protein shown in FIG. (SEQ ID NO: 6) may be generated by a variety of techniques well known in the art.

Also included within the scope of the present invention are alleles of the genes encoding HOMPS. As used herein, an "allele" or "allelic sequence" is an alternative form of the gene which may result from at least one mutation in the nucleic acid sequence. Alleles may result in altered mRNAs. or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence. Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase Amersham Pharmacia Biotech (Pisctaway N.J.), or combinations of recombinant polymerases and proofreading exonucleases such as the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding HOMPS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of $50\%$ or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled.

Capillary electrophoresis is especially preferable for the sequencing of small pieces of DNA which might be present in limited amounts in a particular sample.

In another embodiment of the invention, polynucleotide sequences or fragments thereof which encode HOMPS, or fusion proteins or functional equivalents thereof, may be used in recombinant DNA molecules to direct expression of HOMPS in appropriate host cells. Due to the inherent degeneracy of the genetic code, other DNA sequences which encode substantially the same or a functionally equivalent amino acid sequence may be produced and these sequences may be used to clone and express HOMPS.

As will be understood by those of skill in the art, it may be advantageous to produce HOMPS-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HOMPS encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HOMPS may be ligated to a heterologous sequence to encode a fusion protein. For example, to screen peptide libraries for inhibitors of HOMPS activity, it may be useful to encode a chimeric HOMPS protein that can be recoginzed by a commercially available antibody. A fusion protein may also be engineered to contain a cleavage site located between the HOMPS encoding sequence and the heterologous protein sequence, so that HOMPS may be cleaved and purified away from the heterologous moiety.

In another embodiment, sequences encoding HOMPS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HOMPS, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HOMPS, or any part thereof, may be altered during direct synthesis and/or combined using chemical methods with sequences from other proteins, or any part thereof, to produce a variant polypeptide.

In order to express a biologically active HOMPS, the nucleotide sequences encoding HOMPS or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HOMPS and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y. A variety of expression vector/host systems may be utilized to contain and express sequences encoding HOMPS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculdvirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector-enhancers, promoters, 5' and 3' untranslated regions—which interact with host cellular proteins to carry out transcription and translation. Such elements may vary in their strength and specificity.

Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HOMPS, vectors based on SV40 or EBV may be used with an appropriate selectable marker.

In bacterial systems, a number of expression vectors may be selected depending upon the use intended for HOMPS. For example, when large quantities of HOMPS are needed for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding HOMPS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HOMPS may be driven by any of a number of promoters. For example, viral promoters such as the 35S and 19S promoters of CaMV may be used alone or in combination with the omega leader sequence from TMV (Takamatsu, N. (1987) EMBO J. 6:307–311. Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express HOMPS. For example, in one such system, Autographa californica nuclear polyhedrosis virus (AcNPV) is used as a vector to express foreign genes in *Spodoptera frugiperda* cells or in *Trichoplusia larvae*. The sequences encoding HOMPS may be cloned into a non-essential region of the virus, such as the polyhedrin gene, and placed under control of the polyhedrin promoter. Successful insertion of HOMPS will render the polyhedrin gene inactive and produce recombinant virus lacking coat protein. The recombinant viruses may then be used to infect, for example, *S. frugiperda* cells or *Trichoplusia larvae* in which HOMPS may be expressed (Engelhard, E. K. et al. (1994) Proc. Nat. Acad: Sci. 91:3224–3227).

In mammalian host cells, a number of viral-based expression systems may be utilized. In cases where an adenovirus is used as an expression vector, sequences encoding HOMPS may be ligated into an adenovirus transcription/translation complex consisting of the late promoter and tripartite leader sequence. Insertion in a non-essential E1 or E3 region of the viral genome may be used to obtain a viable virus which is capable of expressing HOMPS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HOMPS. Such signals include the ATG initiation codon and adjacent sequences. In cases where sequences encoding HOMPS, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HOMPS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simnplex virus thymidine kinase (Wigler, M. et al. (1977) Cell 11:223–32) and adenine phosphoribosyltransferase (Lowy, I. et al. (1990) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Nail. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HOMPS is inserted within a marker gene sequence, recombinant cells containing sequences encoding HOMPS can be identified by the absence of marker gene function. Alternatively, a marker gene can be placed in tandem with a sequence encoding HOMPS under the control of a single promoter. Expression of the marker gene in response to induction or selection usually indicates expression of the tandem gene as well.

Alternatively, host cells which contain the nucleic acid sequence encoding HOMPS and express HOMPS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HOMPS can be detected by DNA-DNA or DNA-RNA hybridization or amplification using probes or portions or fragments of polynucleotides encoding HOMPS. Nucleic acid amplification based assays involve the use of oligonucleotides or oligomers based on the sequences encoding HOMPS to detect transformants containing DNA or RNA encoding HOMPS. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HOMPS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HOMPS is preferred, but a competitive binding assay may be employed. These and other assays are described, among other places, in Hampton, R. et al. (1990; Serological Methods, a Laboratory Manual, APS Press, St Paul. Minn.) and Maddox, D. E. et al. (1983; Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HOMPS include oligolabeling, nick translation, end-labeling or PCR amplification using a labeled nucleotide.

Alternatively, the sequences encoding HOMPS, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical Corp. Suitable reporter molecules or labels, which may be used, include radionuclides, enzymes, a fluorescent, chemiluminescent, or chromogenic agents as well as substrates, cofactors, inhibitors, magnetic particles, and the like.

Host cells transformed with nucleotide sequences encoding HOMPS may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HOMPS may be designed to contain signal sequences which direct secretion of HOMPS through a prokaryotic or eukaryotic cell membrane. Other recombinant constructions may be used to join sequences encoding HOMPS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and HOMPS may be used to facilitate purification.

One such expression vector provides for expression of a fusion protein containing HOMPS and a nucleic acid encoding 6 histidine residues preceding a thioredbxin or an enterokinase cleavage site. The histidine residues facilitate purification on IMIAC (immobilized metal ion affinity chromatography) as described in Porath, J. et al. (1992, Prot. Exp. Purif 3: 263–281) while the enterokinase cleavage site provides a means for purifying HOMPS from the fusion protein. A discussion of vectors which contain fusion proteins is provided in Kroll, D. J. et al. (1993; DNA Cell Biol. 12:441–453).

In addition to recombinant production fragments of HOMPS may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HOMPS may be chemically synthesized separately and combined using chemical methods to produce the full length molecule.

Other specifically contemplated embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the HOMPS polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., HOMPS. See for example, Jack Cohen, 1988, OLIGODEOXYNUCLEOTIDES, Antisense Inhibitors of Gene Expression, CRC Press; and Synthesis 1:1–5 (1988). The HOMPS antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693–4698; and Iyer, R. P. et al., 1990, J. Am. Chem. Soc. 112:1253–1254, the disclosures of which are fully incorporated by reference herein. Additional HOMPS antisense oligonucleotides of the present invention include morpholino antisense oligonucleotides known in the art (see e.g. Partridge et al., 1996, Antisense & Nucleic Acid Drug Development 6: 169–175).

The HOMPS antisense oligonucleotides of the present invention typically may be RNA or DNA that is complementary to and stably hybridizes with the first 100 N-terminal codons or last 100 C-terminal codons of the HOMPS genomic sequence or the corresponding mRNA. While absolute complementarity is not required, high degrees of complementarity are preferred. Use of an oligonucleotide complementary to this region allows for the selective hybridization to HOMPS mRNA and not to mRNA specifying other regulatory subunits of protein kinase. Preferably, the HOMPS antisense oligonucleotides of the present invention are a 15 to 30-mer fragment of the antisense DNA molecule having a sequence that hybridizes to HOMPS mRNA. Optionally, HOMPS antisense oligonucleotide is a 30-mer oligonucleotide that is complementary to a region in the first 10 N-terminal codons and last 10 C-terminal codons of HOMPS. Alternatively, the antisense molecules are modified to employ ribozymes in the inhibition of HOMPS expression (L. A. Couture & D. T. Stinchcomb, 1996, Trends Genet. 12: 510–515).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a HOMPS polynucleotide in a sample and as a means for detecting a cell expressing a HOMPS protein.

Illustrative examples of such probes include polypeptides comprising all or part of the human HOMPS H41 cDNA sequences shown in FIG. 5. Examples of primer pairs capable of specifically amplifying HOMPS mRNAs. are also described in the Examples that follow. As will be understood by the skilled artisan, a great many different primers and probes may be prepared based on the sequences provided herein and used effectively to amplify and/or detect a HOMPS mRNA.

As used herein, a polynucleotide is said to be "isolated" when it is substantially separated from contaminant polynucleotides that correspond or are complementary to genes other than the HOMPS gene or that encode polypeptides other than HOMPS gene product or fragments thereof. A skilled artisan can readily employ nucleic acid isolation procedures to obtain an isolated HOMPS polynucleotide.

The HOMPS polynucleotides of the invention are useful for a variety of purposes, including but not limited to their use as probes and primers for the amplification and/or detection of the HOMPS gene(s), mRNA(s), or fragments thereof; as reagents for the evaluation and/or diagnosis and/or prognosis of cancers; as coding sequences capable of directing the expression of HOMPS polypeptides; as tools for modulating or inhibiting the expression of the HOMPS gene(s) and/or translation of the HOMPS transcript(s); and as therapeutic agents.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HOMPS. These techniques are described both in Sambrook et al. (supra) and in Ausubel et al. (supra).

Genes encoding HOMPS can be turned off by transforming a cell or tissue with expression vectors which express high levels of a polynucleotide or fragment thereof which encodes HOMPS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HOMPS, i.e. the promoters, enhancers, and introns. Oligonucleotides derived from the transcription initiation site, e.g. between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HOMPS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HOMPS.

Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life.

Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art. Where appropriate, the methods described above may be applied to any subject in need of such therapy, including, for example, mammals such as dogs, cats, cows, horses, rabbits, monkeys, and most preferably, humans.

As discussed in detail below, in another embodiment, antibodies which specifically bind HOMPS may be used for the evaluation and characterization of conditions or diseases characterized by expression of HOMPS, or in assays to monitor patients being treated with HOMPS, agonists, antagonists or inhibitors. The antibodies useful for diagnostic purposes may be prepared in the same manner as those described above for therapeutics. Diagnostic assays for HOMPS include methods which utilize the antibody and a label to detect HOMPS in human body fluids or extracts of cells or tissues. The antibodies may be used with or without modification, and may be labeled by joining them, either covalendy or non-covalently, with a reporter molecule. A wide variety of reporter molecules which are known in the art may be used, several of which are described above.

A variety of protocols including ELISA, RIA, and FACS for measuring HOMPS are known in the art and provide a basis for diagnosing altered or abnormal levels of HOMPS expression. Normal or standard values for HOMPS expression are established by combining body fluids or cell extracts taken from normal mammalian subjects, preferably human, with antibody to HOMPS under conditions suitable for complex formation. The amount of standard complex formation may be quantified by various methods, but preferably by photometric means. Quantities of HOMPS expressed in subject samples, control and diseases from biopsied tissues are compared with the standard values. Deviation between standard and subject values establishes the parameters for diagnosing disease.

In another embodiment of the invention, the polynucleotides encoding HOMPS may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HOMPS may be correlated with disease. The diagnostic assay may be used to distinguish between absence, presence, and excess expression of HOMPS, and to monitor regulation of HOMPS levels during therapeutic intervention.

In one aspect, hybridization with PCR probes which are capable of detecting polynucleotide sequences, including genomic sequences, encoding HOMPS or closely related molecules, may be used to identify nucleic acid sequences which encode HOMPS. The specificity of the probe, whether it is made from a highly specific region, e.g., 10 unique nucleotides in the 5' regulatory region, or a less specific region, e.g., especially in the 3' coding region, and the stringent of the hybridization or amplification (maximal, high, intermediate, or low) will determine whether the probe identifies only naturally occurring sequences encoding HOMPS, alleles, or related sequences.

Probes may also be used for the detection of related sequences, and should preferably contain at least 50% of the nucleotides from any of the HOMPS encoding sequences. The hybridization probes of the subject invention may be DNA or RNA and derived from the nucleotide sequence of FIG. 1, FIG. 3, FIG. 5, FIG. 8 or FIG. 10 or from genomic sequence including promoter, enhancer elements, and introns of the naturally occurring HOMPS.

Means for producing specific hybridization probes for DNAs encoding HOMPS include the cloning of nucleic acid sequences encoding HOMPS or HOMPS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding HOMPS may be used for the evaluation and characterization of disorders associated with the expression of HOMPS. Examples of such disorders include: various types of cancer such as breast cancer. The polynucleotide sequences encoding HOMPS may be used in Southern or northern analysis, dot blot, or other membrane-based technologies; in PCR technologies; or in dip stick, pin, ELISA or chip assays utilizing fluids or tissues from patient biopsies to detect altered HOMPS expression. Such qualitative or quantitative methods are well known in the art.

In a particular aspect, the nucleotide sequences encoding HOMPS may be useful in assays that detect activation or induction of various cancers such as breast cancer, particularly those mentioned above. The nucleotide sequences encoding HOMPS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HOMPS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the evaluation and characterization of disease associated with expression of HOMPS, a normal or standard profile for expression is established. This may be accomplished by combining body fluids or cell extracts taken from normal subjects, either animal or human, with a sequence, or a fragment thereof, which encodes HOMPS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive evaluation and characterization of this type may allow health professionals to employ preventative measures or aggressive treatment earlier thereby preventing the development or further progression of the cancer.

Additional diagnostic uses for oligonucleotides designed from the sequences encoding HOMPS may involve the use of PCR. Such oligomers may be chermically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Another aspect of the present invention relates to methods for detecting HOMPS polynucleotides and HOMPS proteins and variants thereof, as well as methods for identifying a cell that expresses HOMPS. The expression profile of HOMPS makes it a potential diagnostic marker for local and/or metastasized disease. In this context, the status of HOMPS gene products may provide information useful for predicting a variety of factors including susceptibility to advanced stage disease, rate of progression, and/or tumor aggressiveness. As discussed in detail below, the status of HOMPS gene products in patient samples may be analyzed by a variety protocols that are well known in the art including imunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of HOMPS polynucleotides in a biological sample, such as breast or uterine tissue, serum, bone, prostate, and other tissues, urine, semen, cell preparations, and the like. Detectable HOMPS polynucleotides include, for example, a HOMPS gene or fragments thereof, HOMPS mRNAs, alternative splice variant HOMPS mRNAs, and recombinant DNA or RNA molecules containing a HOMPS polynucleotide. A number of methods for amplifying and/or detecting the presence of HOMPS polynucleotides are well known in the art and may be employed in the practice of this aspect of the invention.

In one embodiment, a method for detecting a HOMPS mRNA in a biological sample comprises producing cDNA from the sample by reverse transcription using at least one primer; amplifying the cDNA so produced using a HOMPS polynucleotides as sense and antisense primers to amplify HOMPS cDNAs therein; and detecting the presence of the amplified HOMPS cDNA. Optionally, the sequence of the amplified HOMPS cDNA can be determined. In another embodiment, a method of detecting a HOMPS gene in a biological sample comprises first isolating genomic DNA from the sample; amplifying the isolated genomic DNA using HOMPS polynucleotides as sense and antisense primers to amplify the HOMPS gene therein; and detecting the presence of the amplified HOMPS gene. Any number of appropriate sense and antisense probe combinations may be designed from the nucleotide sequences provided for the HOMPS (e.g. H41 as shown in FIG. 6) and used for this purpose.

The invention also provides assays for detecting the presence of a HOMPS protein in a tissue of other biological sample such as breast or uterine tissue, serum, bone, prostate, and other tissues, urine, semen, cell preparations, and the like. Methods for detecting a HOMPS protein are also well known and include, for example, nimunoprecipitation, imnunohistochemical analysis, Western Blot analysis, molecular binding assays, ELISA, ELIFA and the like. For example, in one embodiment, a method of detecting the presence of a HOMPS protein in a biological sample comprises first contacting the sample with a HOMPS antibody, a HOMPS-reactive fragment thereof, or a recombinant protein containing an antigen binding region of a HOMPS antibody; and then detecting the binding of HOMPS protein in the sample thereto.

Methods for identifying a cell that expresses HOMPS are also provided. In one embodiment, an assay for identifying a cell that expresses a HOMPS gene comprises detecting the presence of HOMPS mRNA in the cell. Methods for the detection of particular mRNAs. in cells are well known and include, for example, hybridization assays using complementary DNA probes (such as in situ hybridization using labeled HOMPS riboprobes, Northern blot and related techniques) and various nucleic acid amplification assays (such as RT-PCR using complementary primers specific for HOMPS, and other amplification type detection methods, such as, for example, branched DNA, SISBA, TMA and the like). Alternatively, an assay for identifying a cell that expresses a HOMPS gene comprises detecting the presence of HOMPS protein in the cell or secreted by the cell. Various methods for the detection of proteins are well known in the art and may be employed for the detection of HOMPS proteins and HOMPS expressing cells.

HOMPS expression analysis may also be useful as a tool for identifying and evaluating agents that modulate HOMPS gene expression. Identification of a molecule or biological agent that could inhibit HOMPS expression or overexpression in cancer cells may be of therapeutic value. Such an agent may be identified by using a screen that quantifies HOMPS expression by RT-PCR, nucleic acid hybridization or antibody binding.

MONITORING THE STATUS OF HOMPS

Assays that evaluate the status of the HOMPS gene and HOMPS gene products in an individual may provide information on the growth or oncogenic potential of a biological sample from this individual. For example, because HOMPS are modulated by Her-2, an oncogene associated with a number of cancers, assays that evaluate the relative levels of HOMPS mRNA transcripts or proteins in a biological sample may be used to evaluate diseases associated with HOMPS disregulation such as cancer and may provide prognostic information useful in defining appropriate therapeutic options.

Because HOMPS expression is modulated, for example, in cells which overexpress the Her-2 oncogene, the expression status of HOMPS can provide information useful for determining information including the presence, stage and location of displasic, precancerous and cancerous cells, predicting susceptibility to various stages of disease, and/or for gauging tumor aggressiveness. Consequently, an important aspect of the invention is directed to the various molecular methods for examining the status of HOMPS in biological samples such as those from individuals suffering from, or suspected of suffering from a pathology characterized by disregulated cellular growth such as cancer.

Oncogenesis is known to be a multistep process where cellular growth becomes progressively disregulated and cells progress from a normal physiological state to precancerous and then cancerous states (see e.g. Alers et al., Lab Invest. 77(5): 437–438 (1997) and Isaacs et al., Cancer Surv. 23: 19–32 (1995)). In this context, examining a biological sample for evidence of disregulated cell growth can allow the early detection of such aberrant cellular physiology before a pathology such as cancer has progressed to a stage at which therapeutic options are more limited. In such examinations, the status of HOMPS in a biological sample of interest (such as one suspected of having disregulated cell growth) can be compared, for example, to the status of HOMPS in a corresponding normal sample (e.g. a sample from that individual (or alternatively another individual) that is not effected by a pathology, for example one not suspected of having disregulated cell growth) with alterations in the status of HOMPS in the biological sample of interest (as compared to the normal sample) providing evidence of disregulated cellular growth. In addition to using a biological sample that is not effected by a pathology as a normal sample, one can also use a predetermined normative value such as a predetermined normal level of mRNA expression (see e.g. Grever et al., J. Comp. Neurol. 1996 December 9;376(2):306–14 and U.S. Pat. No. 5,837,501) to compare HOMPS in normal versus suspect samples.

The term "status" in this context is used according to its art accepted meaning and refers to the condition or state of a gene and its products. As specifically described herein, the status of HOMPS can be evaluated by a number of parameters known in the art. Typically an alteration in the status of HOMPS comprises a change in the location of HOMPS expressing cells (as occurs in metastases) and/or an increase in HOMEPS mRNA and/or protein expression.

Typically, skilled artisans use a number of parameters to evaluate the condition or state of a gene and its products. These include, but are not limited to the location of expressed gene products (including the location of HOMPS expressing cells) as well as the, level, and biological activity of expressed gene products (such as HOMPS mRNA polynucleotides and polypeptides). Alterations in the status of HOMPS can be evaluated by a wide variety of methodologies well known in the art, typically those discussed below. Typically an alteration in the status of HOMPS comprises a change in the location of HOMPS and/or HOMPS expressing cells and/or an increase in HOMPS mRNA and/or protein expression.

As discussed in detail herein, in order to identify a condition or phenomenon associated with disregulated cell growth, the status of HOMPS in a biological sample may be evaluated by a number of methods utilized by skilled artisans including, but not limited to genomic Southern analysis (to examine, for example perturbations in the HOMPS gene), northerns and/or PCR analysis of HOMPS mRNAs, (to examine, for example alterations in the polynucleotide sequences or expression levels of HOMPS mRNAs.), and western and/or immunohistochemical analysis (to examine, for example alterations in polypeptide sequences, alterations in polypeptide localization within a sample, alterations in expression levels of HOMPS proteins and/or associations of HOMPS proteins with polypeptide binding partners). Detectable HOMPS polynucleotides include, for example, a HOMPS gene or fragments thereof, HOMPS mRNAs, alternative splice variants HOMPS mRNAs, and recombinant DNA or RNA molecules containing a HOMPS polynucleotide.

The expression profile of HOMPS makes them potential markers for disregulated cell growth. In particular, the status of HOMPS may provide information useful for predicting susceptibility to particular disease stages, progression, and/or tumor aggressiveness. The invention provides methods and assays for determining HOMPS status and diagnosing cancers that express HOMPS. HOMPS status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the HOMPS gene and gene products can be found, for example in Ausubul et al. eds., 1995, Current Protocols In Molecular Biology, Units 2 [Northern Blotting], 4 [Southern Blotting], 15 [Immunoblotting] and 18 [PCR Analysis].

As described above, the status of HOMPS in a biological sample can be examined by a number of well known procedures in the art. For example, the status of HOMPS in a biological sample taken from a specific location in the body can be examined by evaluating the sample for the presence or absence of HOMPS expressing cells (e.g. those that express HOMPS mRNA or proteins). This examination can provide evidence of disregulated cellular growth for example, when HOMPS expressing cells are found in a biological sample that does not normally contain such cells (such as a lymph node). Such alterations in the status of HOMPS in a biological sample are often associated with disregulated cellular growth. Specifically, one indicator of disregulated cellular growth is the metastases of cancer cells from an organ of origin (such as the breast) to a different area of the body (such as a lymph node). In this context, evidence of disregulated cellular growth is important for example because occult lymph node metastases can be detected in a substantial proportion of patients with cancers, and such metastases are associated with known predictors of disease progression (see e.g. Freeman et al., J Urol 1995 August;154(2 Pt 1):474–8).

HOMPS ANTIBODIES

The term "antibody" is used in the broadest sense and specifically covers single anti-HOMPS monoclonal antibodies (including agonist, antagonist and neutralizing antibodies) and anti-HOMPS antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that bind to HOMPS proteins and polypeptides. The most preferred antibodies will specifically bind to a HOMPS protein and will not bind (or will bind wealdy) to non-HOMPS proteins and polypeptides. Anti-HOMPS antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

HOMPS antibodies of the invention may be particularly useful in imaging methodologies. Intracellularly expressed antibodies (e.g., single chain antibodies) may be therapeutically useful in treating cancers in which the expression of HOMPS is involved, such as for example Her-2 overexpressing cancers. Such antibodies may be useful in the analysis, treatment, evaluation and characterization, and/or prognosis of other cancers, to the extent HOMPS is also expressed or overexpressed in other types of cancers.

The invention also provides various immunological assays useful for the detection and quantification of HOMPS and mutant HOMPS proteins and polypeptides. Such assays generally comprise one or more HOMPS antibodies capable of recognizing and binding a HOMPS or mutant HOMPS protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing HOMPS are also provided by the invention, including but limited to radioscintigraphic imaging methods using labeled HOMPS antibodies. Such assays may be clinically useful in the detection, monitoring, and prognosis of HOMPS expressing cancers.

HOMPS antibodies may also be used in methods for purifying HOMPS and mutant HOMPS proteins and polypeptides and for isolating HOMPS homologues and related molecules. For example, in one embodiment, the method of purifying a HOMPS protein comprises incubating a HOMPS antibody, which has been coupled to a solid matrix, with a lysate or other solution containing HOMPS under conditions that permit the HOMPS antibody to bind to HOMPS; washing the solid matrix to eliminate impurities; and eluting the HOMPS from the coupled antibody. Other uses of the HOMPS antibodies of the invention include generating anti-idiotypic antibodies that mimic the HOMPS protein.

Various methods for the preparation of antibodies are well known in the art. For example, antibodies may be prepared by immunizing a suitable mammalian host using a HOMPS protein, peptide, or fragment, in isolated or immunoconjugated form (Harlow, and Lane, eds., 1988, Antibodies: A Laboratory Manual, CSH Press; Harlow, 1989, Antibodies, Cold Spring Harbor Press, New York). In addition, fusion proteins of HOMPS may also be used, such as a HOMPS GST-fusion protein. In a particular illustrative embodiment, a GST fusion protein comprising all or most of the open reading frame amino acid sequence of H41 as shown in FIG. 6 may be produced and used as an immunogen to generate appropriate antibodies. In another embodiment, a HOMPS peptide may be synthesized and used as an immunogen.

In addition, naked DNA immunization techniques known in the art may be used (with or without purified HOMPS protein or HOMPS expressing cells) to generate an immune response to the encoded immunogen (for review, see Donnelly et al., 1997, Ann. Rev. Immnunol. 15:617–648):

In an illustrative embodiment, the amino acid sequence of the H41 HOMPS protein as shown in FIG. 6 may be used to select specific regions of the HOMPS protein for generating antibodies. For example, hydrophobicity and hydrophilicity analyses of the HOMPS amino acid sequence may be used to identify hydrophilic regions in the HOMPS structure. Regions of the HOMPS protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances lining reagents such as those supplied by Pierce Chemical Co., Rockford, Ill., may be effective. Administration of a HOMPS immunogen is conducted generally by injection over a suitable time period and with use of a suitable adjuvant, as is generally understood in the art. During the immunization schedule, titers of antibodies can be taken to determine adequacy of antibody formation.

HOMPS monoclonal antibodies are preferred and may be produced by various means well known in the art. For example, immortalized cell lines that secrete a desired monoclonal antibody may be prepared using the standard hybridoma technology of Kohler and Milstein or modifications that immortalize producing B cells, as is generally known. The immortalized cell lines secreting the desired antibodies are screened by immunoassay in which the antigen is the HOMPS protein or a HOMPS fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the HOMPS protein can also be produced in the context of chimeric or CDR grafted antibodies of multiple species origin. Humanized or human HOMPS antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321:522–525; Riechmann et al., 1988, Nature 332:323–327; Verhoeyen et al., 1988, Science 239:1534–1536). See also, Carter et al., 1993, Proc. Nat. Acad. Sci. USA 89:4285 and Sims et al., 1993, J. Immunol. 151:2296. Methods for producing fully human monoclonal antibodies include phage display and transgenic methods (for review, see Vaughan et al., 1998, Nature Biotechnology 16:535–539).

Fully human HOMPS monoclonal antibodies may be generated using cloning technologies employing large human Ig gene combinatorial libraries (i.e., phage display) (Griffiths and Hoogenboom, Building an in vitro immune system: human antibodies from phage display libraries. In: Clark, M., ed., 1993, Protein Engineering of Antibody Molecules for Prophylactic and Therapeutic Applications in Man, Nottingham Academic, pp 45–64; Burton and Barbas, Human Antibodies from combinatorial libraries. Id., pp 65–82). Fully human HOMPS monoclonal antibodies may also be produced using transgenic mice engineered to contain human immunoglobulin gene loci as described in PCT patent application Ser. No. WO98/24893, Kucherlapati and Jakobovits et al., published Dec. 3, 1997 (see also, Jakobovits, 1998, Exp. Opin. Invest. Drugs 7(4):607–614). This method avoids the in vitro manipulation required with phage display technology and efficiently produces high affinity authentic human antibodies.

Reactivity of HOMPS antibodies with a HOMPS protein may be established by a number of well known means, including western blot, immunoprecipitation, ELISA, and FACS analyses using, as appropriate, HOMPS proteins, peptides, HOMPS-expressing cells or extracts thereof.

A HOMPS antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the HOMPS antibody can be selected in accordance with the intended use. For example, for therapeutic use, the second molecule can be a toxin or therapeutic agent. Further, bi-specific antibodies specific for two or more HOMPS epitopes may be generated using methods generally known in the art. Homodimeric antibodies may also be generated by cross-linking techniques known in the art (e.g., Wolff et al., 1993, Cancer Res. 53: 2560–2565).

HOMPS TRANSGENIC ANIMALS

Nucleic acids that encode HOMPS or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding HOMPS can be used to clone genomic DNA encoding HOMPS in accordance with established techniques and the genomic sequences used to generate transgenic animals that contain cells that express DNA encoding HOMPS. Methods for generating transgenic animals, particularly animals such as mice or rats, have become conventional in the art and are described, for example, in U.S. Pat. Nos. 4,736,866 and 4,870,009. Typically, particular cells would be targeted for HOMPS transgene incorporation with tissue-specific enhancers. Transgenic animals that include a copy of a transgene encoding HOMPS introduced into the germ line of the animal at an embryonic stage can be used to examine the effect of increased expression of DNA encoding HOMPS. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of HOMPS can be used to construct a HOMPS "knock out" animal that has a defective or altered gene encoding HOMPS as a result of homologous recombination between the endogenous gene encoding HOMPS and altered genomic DNA encoding HOMPS introduced into an embryonic cell of the animal. For example, cDNA encoding HOMPS can be used to clone genomic DNA encoding HOMPS in accordance with established techniques. A portion of the genomic DNA encoding HOMPS can be deleted or replaced with another gene, such as a gene encoding a selectable marker that can be used to monitor integration. Typically, several kilobases of unaltered flanking DNA (both at the 5' and 3' ends) are included in the vector (see e.g., Thomas and Capecchi, 1987, Cell 51:503) for a description of homologous recombination vectors]. The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Robertson, ed., 1987, Teratocarcinomas and Embryonic Stem Cells: A Practical Approach, (IRL, Oxford), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the HOMPS polypeptide.

IDENTIFYING MOLECULES THAT INTERACT WITH HOMPS

The HOMPS protein sequences disclosed herein allow the skilled artisan to identify molecules that interact with them via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with HOMPS protein sequences by screening peptide libraries. In such methods, peptides that bind to selected receptor molecules such as HOMPS are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with HOMPS protein sequences are disclosed for example in U.S. Pat. Nos. 5,723,286 and 5,733,731.

Alternatively, cell lines expressing HOMPS can be used to identify protein-protein interactions mediated by HOMPS. This possibility can be examined using immunoprecipitation techniques as shown by others (Hamilton, B. J., et al., 1999, Biochem. Biophys. Res. Commun. 261:646–51). Typically HOMPS protein can be immunoprecipitated from HOMPS expressing cancer cell lines using anti-HOMPS antibodies. Alternatively, antibodies against His-tag can be used in cell line engineered to express HOMPS (vectors mentioned above). The immunoprecipitated complex can be examined for protein association by procedures such as western blotting, $^{35}$S-methionine labeling of proteins, protein microsequencing, silver staining and two dimensional gel electrophoresis.

Related embodiments of such screening assays include methods for identifying small molecules that interact with HOMPS. Typical methods are discussed for example in U.S. Pat. No. 5,928,868 and include methods for forming hybrid ligands in which at least one ligand is a small molecule. In an illustrative embodiments, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

Methods which may also be used to quantitate the expression of HOMPS include radiolabeling or biotinylating nucleotides, coamplification of a control nucleic acid, and standard curves onto which the experimental results are interpolated (Melby, P. C. et al. (1993) J. Immnunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HOMPS may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154. FISH (as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in the 1994 Genome Issue of Science (265:1981f).

Correlation between the location of the gene encoding HOMPS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HOMPS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HOMPS and the agent being tested, may be measured.

Another technique for drug screening which may be used provides for high throughput screening of compounds having suitable binding affinity to the protein of interest as described in published PCT application W084/03564. In this method, as applied to HOMPS large numbers of different small test compounds are synthesized on a solid substrate, such as plastic pins or some other surface. The test compounds are reacted with HOMPS, or fragments thereof, and washed. Bound HOMPS is then detected by methods well known in the art. Purified HOMPS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HOMPS specifically compete with a test compound for binding HOMPS. In this manner, the antibodies can be used to detect the presence of any peptide which shares one or more antigenic determinants with HOMPS.

In additional embodiments, the nucleotide sequences which encode HOMPS may be used in any molecular biology techniques that have yet to be developed, provided the new techniques rely on properties of nucleotide sequences that are currently known, including, but not limited to, such properties as the triplet genetic code and specific base pair interactions.

KITS

For use in the applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a HOMPS protein or a HOMPS gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

EXAMPLES

Various aspects of the invention are further described and illustrated by way of the several examples that follow, none of which are intended to limit the scope of the invention.

1. Cell Culture

Cells were grown in RPMI medium 1640, supplemented with 10% fetal bovine serum, 2 mM glutamine, and 1% penicillin G-streptomycin-fungizone solution. Cells were harvested at 80% confluency for total RNA extraction.

2. RNA Preparation

Total cellular RNA was purified by guanidinium/cesium chloride ultracentrifugation (16). Messenger RNA was isolated by two passages through an oligo dT cellulose column (T3-Collaborative Research) (17). The quality and mRNA composition of the resulting RNA population were confirmed by Northern blot analysis by probing with β-actin and HER-2 cDNAs. Both MCF-7/control and MCF-7/HER2 mRNA pools contain equivalent, basal expression of the endogenous HER-2 transcript whereas the transcript representing transfected HER-2 cDNA was present only in the MCF-7/HER2 cells.

3. Construction of the cDNA Library

Five $\mu$g of MCF-7/HER2 poly (A)$^+$ RNA was constructed into ZAP Express™ vector (Stratagene) according to the manufacturer's protocol using materials provided in the cDNA synthesis kit. The recombinant phage were packaged in Gigapack II Gold packaging extract (Stratagene). The packaged library was amplified one round through passage on XL1-Blue MRF' host cells ($6 \times 10^5$ pfu/µl titer). As determined by the X-gal/IPTG color assay, the background (non-recombinant) phage level was less than 0.11%.

4. Differential Hybridization

The MCF-7/HER2 cDNA library was plated on XL1-Blue MRF' host cells at a density of 2,000 pfu per each of eight 150 mm petri dishes. After plating, actin and HER-2 clones purified from the same library were each loaded onto four designated spots within the individual plates to be used as hybridization controls. The nitrocellulose filters (Millipore) were placed on the agar plates 1.5 min. for the first filter, 3 min. for the second, and 7 min. for the third. The phage DNA was denatured for 3 min. in a solution containing 0.5 M NaOH 1.5 M NaCl, neutralized for 3 min. in a solution containing 3 M NaCl 0.5 M Tris-pH 7.5, and rinsed in 2×SSC. The treated filters were air-dried and baked at 80° C. for 1 hour.

The radiolabeled cDNA probes (MCF7/control and MCF-7/HER2) were prepared as follows. Poly (A)$^+$RNA was randomly labeled, by using both random hexamers and oligo dT primers, in 20 µl solution containing 1.0 µg poly (A)$^+$ RNA, 1×MMLV buffer, 1 mM each of dATP, dGTP, dTTP and 0.045 mM dCTP, 100 µCi γ[$^{32}$P]dCTP, 0.5 µg oligo dT$_{(15)}$, 0.2 µg random primer, 20 U RNase inhibitor, and 200 U Moloney murine leukemia virus (MMLV) reverse transcriptase. The reaction was incubated at room temperature first for 10 min to allow primer annealing and further incubated at 37° C. for 1 hour. Upon addition of 4.6 µl of 0.5 M NaOH, the reaction-mix was incubated at 70° C. of 20 min. Incorporated counts were eluted from a spin column (Chromaspin 100/Clontech) in 1×TEN buffer (0.1 M NaCl, 10 mM Tris.pH 8.0, 1 mM EDTA).

Approximately $5.9 \times 10^7$ dpm counts of MCF-7/control probes were added to a first hybridization containing 26 ml hybridization solution and the first set of 8 filters obtained from each plate. Equal counts of MCF-7/HER2 probes were added to the second set of filters. The third set of filters were hybridized with radioactive HER-2 cDNA in order to avoid selecting the HER-2 containing clones. Hybridization solution contained 50% formamide, 25×Denhardts, sonicated salmon sperm DNA, NaPO$_4$.pH 6.8, sodium pyrophosphate, and ribo ATP. Prehybridization was performed at 42° C. for 4 h. and hybridization at 42° C. for 4 days (overnight hybridization for the third set of filters). Filters were washed at room temperature for 5 min. (×3) in 0.2×SSC/0.1%SDS, and at 60° C. for 15 min. (×7) in the same solution. The washed filters were exposed with an intensifying screen to Kodak-XAR5 films at −70° C. for various time periods. Autoradiograms were analyzed to compare differences in focal signal intensity between the replica filters.

For the secondary screenings, the primary screening procedure was repeated except that each clone was separately plated onto a 100 mm petri dish at a low density of 25–50 plaques/plate.

5. Probe Generation for Northern Hybridization

The pBK-CMV phagemid was in vivo excised from the lamdaphage vector according to the manufacturer's instructions (Stratagene). The cDNA inserts were isolated from the plasmid either by restriction enzyme digestions or by PCR amplification using T3 and T7 sequences as primers.

6. Northern Hybridization

Either 2 µg of poly (A)$^+$RNA or 20 µg of total RNA was loaded onto a 1% formaldehyde agarose gel and electrophoresed at 70 V for 4 hours. The RNA was transferred to a nylon membrane in 10×SSC. The purified cDNA inserts were random-labeled in a 50 µl reaction mix which contained 50 ng template, [γ-$^{32}$P] dCTP, 20 µg BSA, 6 U Klenow. Incorporated counts were eluted from a G-50 Sephadex spin column (Pharmacia). Approximately $3 \times 10^6$ dpm counts per 1 ml hybridization solution were used. The hybridization was carried out in 50% formamide, 2×SSC, 0.1% SDS, 10 mg/ml salmon sperm DNA, and 10% dextran sulfate, at 42° C. for 16 hours. Membranes were washed in 2×SSC/0.1%SDS at 25° C. for 10 min. (×3), and in the same solution at 65° C. for 5 min. (×2). The washed membranes were exposed with an intensifying screen to Kodak-XAR film at −70° C.

7. DNA Sequencing and Computer Analysis

Minipreparations of pBK-CMV plasmid vector (Qiawell 8 Ultra, Qiagen) were sequenced with T3/T7 promoter primers and internal primers using an automatic DNA sequencer (Applied Biosystems Model 373A). The sequence similarity search was performed using GenBank and EMBL DNA databases.

8. In Vitro Transcription/Translation

The cDNA inserts were translated into polypeptides in a TNT coupled reticulocyte system (Promega) according to the manufacturer's protocol; Approximately 1 µg of purified plasmid template was transcribed and translated in the 50 µl reaction containing T3 RNA polymerase, rabbit reticulocyte lysate, [$^{35}$S]methionine, etc. 5 µl of the end product was aliquoted to estimate the molecular size of the in vitro translated protein using 10% SDS-PAGE and prestained protein size markers (Bio-Rad).

9. Extraction of Total RNA from Breast Tumor Samples

Breast tumors were obtained from patients at the time of surgery as part of a core tissue procurement resource sponsored by the DOD breast cancer program. All tumor samples were snap frozen in liquid nitrogen and kept at −70° C. before extraction of RNA. Frozen tissues were pulverized in liquid nitrogen prior to homogenization in cold 4 M guanidine thiocyanate buffer (7.5 ml/g of tissue). The homogenates were centrifuged for 10 min. at 4° C. at 8000 g in order to remove cell debris. RNA was sedimented through a cesium chloride gradient (5.7 M/2.4 M CsCl$_2$) via ultracentrifugation (18 h at 36,000 rpm, 20° C.). The separated RNA phases were extracted with phenol-chloroform prior to wash with 100 % ethanol. The RNA pellet was precipitated by adding 2 ml of 0.4 M sodium acetate and 2.5 vol. of 100 % ethanol, and storing over night at −20° C. After centrifugation (20 min at 10,000 g), the pellets were dried and dissolved in DEPC water.

10. Isolation of Differentially Expressed Genes Associated with HER-2/neu Overexpression In our first round of differential screening, 16,000 clones from the MCF-7/HER-2 library were analyzed. Clones showing a stronger signal intensity hybridized with the MCF-7/control cell cDNA probes were labeled "C" clones (C1, C2, C3, etc.), whereas those demonstrating a stronger signal intensity hybridized with HER-2 overexpressing cell cDNA probes were labeled "H" clones (H1, H2, H3, etc.). From this primary screening, a total of 127 differentially expressed clones were isolated including 77 C clones and 50 H clones representing genes whose expression levels are decreased (C clones) or increased (H clones) respectively in association with HER-2 overexpression. Each clone was ranked according to degree of differential hybridization based on signal intensity ranging from more than a five fold to less than a two fold change based on visualization.

Forty-three C clones and 36 H clones which demonstrated the greatest differences in signal intensity in the primary screening were taken through secondary screening to ensure consistent differential expression and to isolate pure colonies. Subsequent to this isolation, the clones were cross-hybridized to determine redundancy. This resulted in a total of 7 non-redundant C clones and 12 non-redundant H clones. Finally, to confirm our screening technique, differential expression patterns of the selected clones were evaluated by Northern blot analysis of RNA from MCF-7/control and HER-2 cells. A total of 5 C clones and 11 H clones showed expression patterns consistent with expectations from the differential hybridization approach while 2 C clones and 1 H clone failed to demonstrate the anticipated pattern.

11. DNA Sequencing and Identification of the Clones

Individual clones whose differential expression was confirmed by Northern blot analysis were subsequently analyzed by DNA sequencing, and these data demonstrate that full-length cDNAs were obtained for most of the clones. The differentially expressed genes were grouped into three different classes based on computer searches against the GenBank and EMBL data bases; (1) known genes with previously characterized function (2) previously identified genes with relatively uncharacterized function (3) novel sequences (summarized in Table 1 below). In addition, each clone was grouped into three different categories based on significance of their relative difference in expression (Table 1). Even genes whose differential expression is small (~2 fold) were included if this difference was consistently reproducible in multiple analyses.

As stated above, the MCF-7/HER-2 cells behave significantly differently than their isogenic control parental counterparts; with increases in DNA synthesis, cell growth in vitro, soft agar cloning efficiency and tumorigenicity. Nine of the differentially expressed genes identified in this study are known to be associated with the malignant phenotype. For example, cytokeratin 8 (C29) (Taniguchi, T., Fujii-Kuriyama, Y. and Muramatsu, M. (1980) *Proc Natl Acad Sci USA*, 77(7), 4003–6), cytokeratin 18 (C49) (Oshima, R. G., Millan, J. L. and Cecena, G. (1986) *Differentiation*, 33(1), 61–8), and gamma actin (C72) (Erba, H. P., Gunning, P. and Kedes, L. (1986) *Nucleic Acids Res*, 14(13), 5275–94) are cytoskeletal proteins essential for maintaining both cell shape and motility of normal cells and their expression differs from levels seen in the aberrant cytoskeleton of cancer cells (Nukhopadhyay, T. and Roth, J. A. (1996) *Anticancer Res*, 16(1), 105–12). Similarly GAPDH (H31) (Tokunaga, K., Nakamura, Y., Sakata, K., Fujimori, K., Ohkubo, M., Sawada, K. and Sakiyama, S. (1987) *Cancer Res*, 47(21), 5616–9) and succinyl CoA transferase (H45) (Kassovska-Bratinova, S., Fukao, T., Song, X. Q., Duncan, A. M., Chen, H. S., Robert, M. F., Perez-Cerda, C., Ugarte, M., Chartrand, C., Vobecky, S., Kondo, N. and Mitchell, G. A. (1996) *Am J Hum Genet*, 59(3), 519–28) are involved in the metabolic pathway of more rapidly growing cells including cancer cells. The increased expression of ribosomal proteins, L8 (H16) (Hanes, J., Klaudiny, J., von der Kammer, H. and Scheit, K. H. (1993) *Biochem Biophys Res Commun*, 197(3), 1223–8) and LLrep3 (H35) (Heller, D. L., Gianola, K. M. and Leinwand, L. A. (1988) *Mol Cell Biol*, 8(7), 2797–803), is consistent with the increased rate of protein translation required for cancer cell growth. Two other genes identified in our study whose cellular functions have been previously characterized are Cathepsin D (C31) (Faust, P. L., Kornfeld, S. and Chirgwin, J. M. (1985) *Proc Natl Acad Sci USA*, 82(15), 4910–4), an acidic lysosomal protease, and the 90 kDa heat shock protein (H118) (Rebbe, N. F., Ware, J., Bertina, R. M., Modrich, P. and Stafford, D. W. (1987) *Gene*, 53(2–3), 235–45) which is a chaperon protein associated with steroid hormone receptor genes. Both of these genes are known to be differentially expressed in malignant cells Johnson, M. D., Torri, J. A., Lippman, M. E. and Dickson, R. B. (1993) *Cancer Res*, 53(4), 873–7; Mileo, A. M., Fanuele, M., Battaglia, F., Scambia, G., Benedetti-Panici, P., Mancuso, S. and Ferrini, U. (1990) *Anticancer Res*, 10(4), 903–6).

Figure 13:
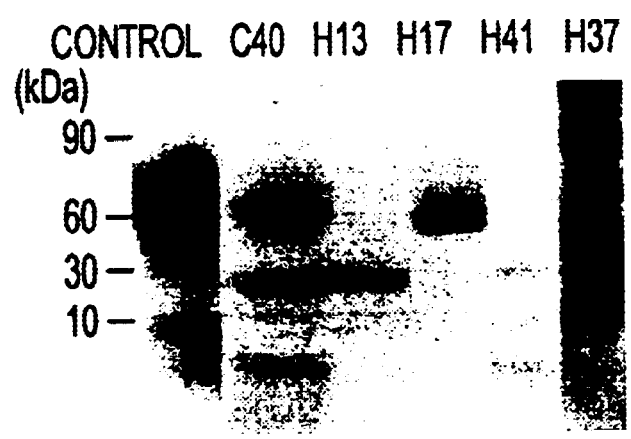
FIG. 13 shows an in vitro transcription/translation of the proteins from the identified differentially expressed transcripts. The transcription-coupled translation reaction was performed using T3 RNA polymerase, rabbit reticulocyte lysate and [$^{35}$S]methionine labeling. The first lane represents the 61 kDa luciferase protein product which was used as a positive control. The C40, H13, H17, and H37 protein products are seen as distinct bands at 55, 30, 50, and 90 kDa, respectively, whereas the H41 cDNA produced two faint bands at 30 kDa and a lower molecular weight. The protein molecular weight marker is shown on the left.

Three genes (H13, H14, H37) found to be overexpressed in the HER-2 overexpressing cells matched cDNA sequences which were previously identified by other investigators but not fully characterized. The H13 clone appears to be an alternate splice variant of DNA fragmentation factor (DFF) (GenBank accession no. U91985) (Liu, X., Zou, H., Slaughter, C. and Wang, X. (1997) *Cell*, 89(2), 175–84); the first 261 amino acid sequences contained in both H13 and the DFF open reading frames are identical, but H13 lacks 70 amino acids at the 3' end and contains 7 different amino acids in their place. The predictive amino acid sequence for H13 is highly similar to the ICAD (Inhibitor of Caspase-Activated Dnase)-S and -L proteins (Sakahira, H., Enari, M. and Nagata, S. (1998) *Nature*, 391(6662), 96–9; Enari, M., Sakahira, H., Yokoyama, H., Okawa, K., Iwamatsu, A. and Nagata, S. (1998) *Nature*, 391(6662), 43–50) (73% and 69% sequence identity, respectively). In order to ensure that the cDNAs cloned, either uncharacterized or novel, can be efficiently translated into protein products of expected sizes, we performed in vitro—translation experiments. As predicted, the H13 cDNA was translated into the polypeptide of approximately 30 kDa (FIG. 13) Clone H14 is identical to DRP-1 Density regulated protein-1/GenBank accession no. AF038554) (Deyo, J. E., Chiao, P. J. and Tainsky, M. A. (1998) *DNA Cell Biol*, 17(5), 437–47) except that it lacks 285 bp at the 5' end and has 23 additional bp at the 3' end plus a poly (A) tail. Both the H14 and DRP-1 cDNAs are likely to be partial, 3' end sequences of a larger transcript since no suitable initiating codon was found in either sequences, and the H14 cDNA hybridized with an additional transcript of approximately 6.5 kb on Northern blot analysis. According to the EST (Expressed Sequence Tags) database analysis, the 5' end of the H14 cDNA sequence can be extended, and the ESTs covering the extended portion of the gene is designated THC202438 (deposited in the Tentative Human Consensus effort) (Kirkness, E. F. and Kerlavage, A. R. (1997) *Methods Mol Biol*, 69, 261–8). The H37 cDNA sequence has been previously deposited into GenBank as RNA binding motif protein 5 (RBM5) (accession no. AF091263, unpublished) found within a region reported to be homozygously deleted in lung cancer and believed to contain (a) major tumor suppressor gene(s) involved in a majority of small cell and non-small cell lung cancers (Wei, M. H., Latif, F., Bader, S., Kashuba, V., Chen, J. Y., Duh, F. M., Sekido, Y., Lee, C. C., Geil, L., Kuzmin, I., Zabarovsky, E., Klein, G., Zbar, B., Minna, J. D. and Lerman, M. I. (1996) *Cancer Res*, 56(7), 1487–92). The H37 cDNA contains an open reading frame of 816 amino acid and is translated in vitro into a predicted protein product of approximately 90 kDa (FIG. 13). Analysis of the putative H37 protein against PROSITE protein profile databases recognized the presence of two RNA binding domains, located at amino acid residues 140–147 and 274–281, which are perfect matches with the consensus eukaryotic sequence for a putative RNA-binding region RNP-1 (Bandziulis, R. J., Swanson, M. S. and Dreyfuss, G. (1989) *Genes Dev*, 3(4), 431–7).

Four clones (C40, H17, H41, H63) represented as-yet unknown genes in the DNA databases, and three of these (C40, H17, H41) were found to contain probable open reading frames. The 1750 bp long C40 clone contains a 510 amino acid open reading frame (FIG. 14A). The coding region of this gene begins with a start codon at nucleotide position 74 and has an in-frame stop codon at position 1604 (FIG. 14A). The C40 clone was in vitro—translated into the predicted major protein product of approximately 55 kDa (FIG. 13). The 385 bp region (nt 568–952) of this gene is 89% identical to a GenBank transcript (accession no. U56429), however, the putative C40 protein does not share any significant homology to any known proteins in the databases. Examination of the C40 protein sequence using the GCG program Motifs revealed the presence of a leucine zipper motif at amino acid positions 104–125, which is a perfect match with the consensus sequence for the leucine zipper pattern (Steeg, P. S., Bevilacqua, G., Kopper, L., Thorgeirsson, U. P., Talmadge, J. E., Liotta, L. A. and Sobel, M. E. (1988) *J Natl Cancer Inst*, 80(3), 200–4) (FIG. 14A).

The 1981 bp long H17 clone contains a consensus initiation codon (Kozak, M. (1991) *J Biol Chem*, 266(30), 19867–70) at nucleotide 66 followed by a 486 amino acid open reading frame and a 458 bp 3' untranslated region including a polyadenylation signal (AATAAA) (FIG. 14B). As is known in the art, the nucleic acid sequence around the 5' proximal AUG codon is typically a Kozak consensus sequence where eukaryotic ribosoimes initiate translation and the general rule the eukaryotic ribosomes initiate translation exclusively at the 5' proximal AUG codon is abrogated only under rare conditions (see e.g. Kozak PNAS 92(7): 2662–2666, (1995) and Kozak NAR 15(20): 8125–8148 (1987)). In vitro translation generated the predicted protein product of approximately 50 kDa (FIG. 13). The putative H17 protein has 39.30% identity with a *C. elegans* cDNA of unknown function (Z77667) over a 422 amino acid region (aa 61–482) and is similar to a metabolic enzyme sarcosine oxidase (AE001086) with 29.2% identity in a 171 amino acid region (aa 66–236) (FIG. 14B).

Figure 14C:
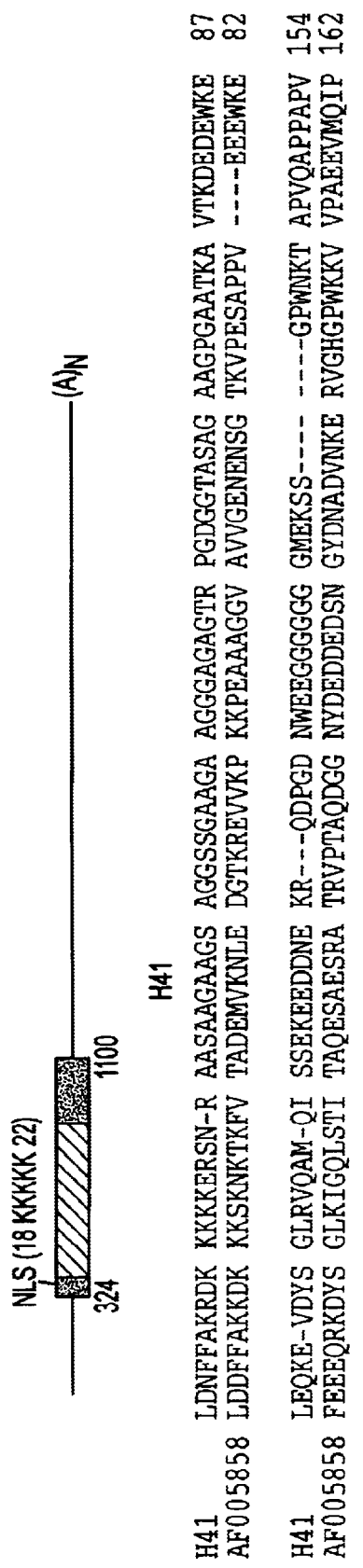
FIG. 14 shows a schematic representation of the three differentially expressed novel genes. The thin line indicates a stretch of nucleotide sequences ending at poly A tail, denoted by $(A)_N$, at the base pair number written next. The filled box illustrates location of the most probable open reading frame, with the numbers below indicating the base pair positions of start and stop codons respectively. A, Map of the C40 cDNA, the leucine zipper motif is denoted by LZ and shown above is the corresponding amino acid positions and sequences. B, Map of the H17 cDNA, the asterisks above poly A tail indicate the presence of polyadenylation signals. The hatched box illustrates the ammio acid region of shared homology and the sequence alignments are shown below the gene. Identical residues are indicated by shading (Z77667 (SEQ ID NO: 12)=a *C. elegans* cDNA of unknown function, AE001086 (SEQ ID NO: 13)=sarcosine oxidase). Numbers at the right represent corresponding amino acid positions. Gaps introduced for maximal alignment are marked with dashes. C, Map of the H41 cDNA, NLS= nuclear localization signal, AF005858 (SEQ ID NO: 14)= one of the "fast evolving" drosophila genes of unknown function.

The 3346 bp H41 clone contains a 323 bp 5' untranslated region followed by an initiation codon with a Kozak consensus (Kozak, M. (1991) *J Biol Chem*, 266(30), 19867–70) and an extensive, 2249 bp 3' untranslated region (FIG. 14C). The 258 amino acid residues encoded by its open reading frame was translated in vitro into the predicted protein product of approximately 30 kDa and an additional protein of lower molecular weight (FIG. 13). The putative H41 protein is related to one of the "fast evolving" drosophila genes of unknown function (AF005858) (Schmid, K. J. and Tautz, D. (1997) *Proc Natl Acad Sci USA*, 94(18), 9746–50) with 28.7% identity in a 167 amino acid region (aa 9–175) (FIG. 14C). According to a pSORT protein database search, the H41 gene product is predicted to be a nuclear protein based on the presence of a nuclear localization signal, 4 basic amino acid (lysine) residues, at its N-terminus (94.1% reliability by Reinhardt's method) (Reinhardt, A. and Hubbard, T. (1998) *Nucleic Acids Res*, 26(9), 2230–6) (FIG. 14C). For the above three novel cDNA sequences (C40, H17, H41), we could not find any ESTs which would extend our sequences further either at the 5' or 3' ends.

Lastly, the novel H63 clone is believed to be a partial, 3' sequence of a longer transcript because this sequence did not contain any probable open reading frames, and the 2068 bp DNA hybridized with a transcript of approximately 4.5 kb on a Northern blot. According to the EST database analysis, the 5' end of the H63 cDNA sequence can be extended and assembled as THC175350.

TABLE 1

Identity of differentially expressed clones

| Clone #[a] | Size[b] (bp) | Clone Identity | mRNA size[c] (kb) | Relative difference in expression[d] | Accession number |
|---|---|---|---|---|---|
| (1) Genes with previously characterized function | | | | | |
| C29 | 1777 | Keratin 8 | 1.8 | ↓↓ | X74929 |
| C31 | 2053 | Cathepsin D | 2.1 | ↓↓ | M11233 |
| C49 | 1423 | Keratin 18 | 1.4 | ↓↓ | M26326 |
| C72 | 1940 | Gamma actin | 1.9 | ↓ | X04098 |
| H16 | 933 | Ribosomal protein L8 | 0.9 | ↑ | Z28407 |
| H18 | 2530 | 90-kDa heat-shock protein | 1.2, 2.5 | ↑↑↑ | M16660 |
| H31 | 1284 | Glyceraldehyde-3-phosphate dehydrogenase | 1.3 | ↑↑ | M33197 |
| H35 | 948 | LLRep3 | 0.9 | ↑↑↑ | X17206 |
| H45 | 2317 | Succinyl CoA: 3-oxoacid CoA transferase | 1.5, 3.3, 5.3 | ↑↑ | U62961 |
| (2) Recently identified genes with relatively uncharacterized function | | | | | |
| H13 | 1027 | DNA fragmentation factor (DFF) | 1.0, 1.4, 3.4, 6.4 | ↑↑ | AF103799[e] |
| H14 | 2214 | Density Regulated Protein-1 (DRP-1) | 0.96, 2.2, 6.5 | ↑↑↑ | AF103800[e] |
| H37 | 3091 | RNA binding motif protein 5 (RBM5) | 1.9, 3.1, 6.5 | ↑↑ | AF103802[e] |
| (3) Novel sequences | | | | | |
| C40 | 1750 | Not previously identified | 1.8, 2.6, 4.9 | ↓ | AF103798[e] |
| H17 | 1981 | Not previously identified | 2.0, 4.4 | ↑↑↑ | AF103801[e] |
| H41 | 3346 | Not previously identified | 1.9, 2.7, 3.3, 4.0 | ↑↑↑ | AF103803[e] |
| H63 | 2068 | Not previously identified | 1.9, 4.5 | ↑ | AF103804[e] |

[a]Prefix "C" and "H" denotes genes whose expression level decrease and increase, respectively, in MCF-7/HER-2 cells compared to the control cells.
[b]The size of cDNAs cloned in the differential screening and used as probes for Northern blot analysis.
[c]The sizes of differentially expressed transcripts on Northern autoradiogram.
[d]Directions of arrows indicate expression level increase (↑) or decrease (↓), respectively, in HER-2 overexpressing cells. The number of arrows indicates relative difference in expression level change by visualization, i.e. ↑ = ~2 fold, ↑↑ = 3–5 fold, ↑↑↑ = >5 fold.
[e]The nucleotide sequences reported in this study have been submitted to the GenBank ™/EMBL database and assigned these accession numbers.

12. Confirmation of Differential Expression in Ovarian Cancer Cell Counterparts

To ensure that differential expression of these genes is a phenomenon consistently associated with HER-2/neu overexpression rather than a unique event restricted to a single cell line, we evaluated the expression of these genes in human ovarian cancer cells (CaOv-3) engineered to overexpress HER-2/neu in a fashion identical to the MCF-7/

Figure 15:
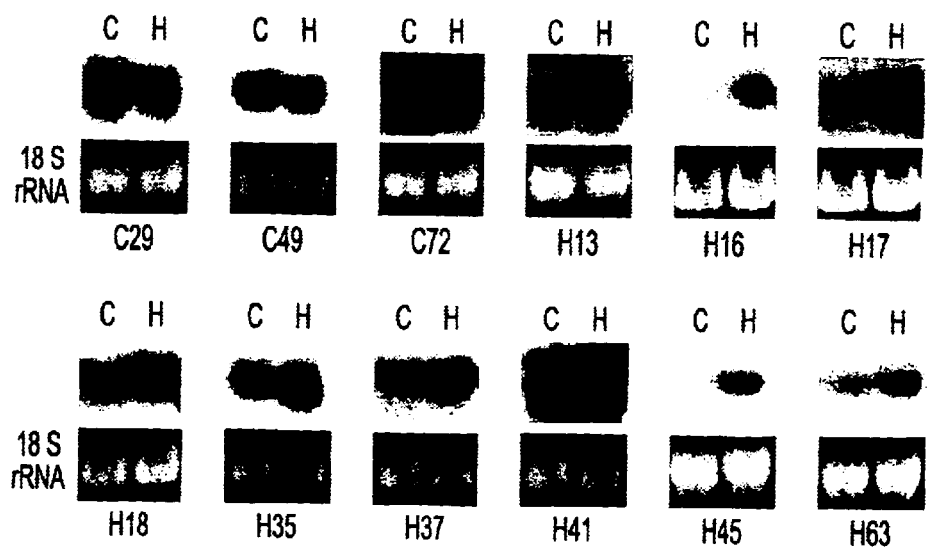
FIG. 15 shows the confirmation of differential expression in CaOv-3 ovarian cancer cells overexpressing HER-2. The differential expression patterns of three C clones and nine H clones identified in MCF-7 breast cancer cells were reproduced in CaOv-3 ovarian cancer cell counterparts on Northern blot (C=Control, H=HER-2 transfectant.) 20 µg of total RNA was loaded in each lane. Ethidium bromide staining of 18 S ribosomal RNA is shown as a loading control below autoradiograms. The transcript sizes are as shown in FIG. 12.

HER-2 cells (Pietras, R. J., Fendly, B. M., Chazin, V. R., Pegram, M. D., Howell, S. B. and Slamon, D. J. (1994) *Oncogene*, 9(7), 1829–38; Pegram, M. D., Finn, R. S., Arzoo, K., Beryt, M., Pietras, R. J. and Slamon, D. J. (1997) *Oncogene*, 15(5), 537–47). The amount of HER-2/neu protein expressed, as determined by quantitative Western blot analysis, was approximately 1.62 pg/cell for MCF-7/HER-2 cells and 1.14 pg/cell for the CaOv-3/HER-2 cells as compared to 0.36 pg/cell and 0.41 pg/cell for the control transfected cells respectively (Press, M. F., Pike, M. C., Chazin, V. R., Hung, G., Udove, J. A., Markowicz, M., Danyluk, J., Godolphin, W., Sliwkowski, M., Akita, R. and et al. (1993) *Cancer Res*, 53(20), 4960–70). In addition, the biologic changes induced by HER-2/neu overexpression in the human ovarian cancer cells were similar to those seen and described above in the human breast cancer cells (Chazin, V. R. (1991). The biologic effects of HER-2/neu proto-oncogene overexpression, Chapter 2. Department of Microbiology and Immunology, University of California, Los Angeles). Based on this consistent pattern of biologic changes induced by HER-2/neu overexpression for both the MCF-7/HER-2 and CaOv-3/HER-2 cell lines, we would anticipate that at least some of the changes in mRNA expression patterns associated with HER-2 overexpression might be similar between these two cell lines if these genes are relevant to the HER-2/neu overexpressing phenotype. Northern blot analysis of ovarian cancer cell line pair demonstrated that 12 of 16 (75%/) clones found to be differentially expressed in MCF-7/HER-2 as compared to isogenic control breast cancer cells were also differentially expressed in the CaOv-3 ovarian cancer cells (FIG. 15). In addition, for most of the clones, the degree of differential expression was consistent between these two distinct epithelial cell lines. This phenomenon is seen with clones H17, H18, H35, H37, and H41 which show marked increases in expression levels in association with HER-2/neu overexpression and clones C49, C72, H16, H45, and H63 which show more subtle differences (FIG. 15). Four of the MCF-7 differentially expressed clones (C31, C40, H14, H31) did not demonstrate any noticeable difference in expression in CaOv-3/HER-2 vs. control cells.

Figure 16A:
FIG. 16 shows that the upregulation of the H37 and H41 transcripts correlates with HER-2/neu overexpression in human breast tumors (p<0.005 and p<0.075 respectively). A, Northern blot analysis was performed to compare expression levels of the HER-2 vs. H37 cDNAs in 15 individual breast tumor samples. Ten µg of total RNA was loaded in each lane, and the same blot was stripped for rehybridization with the second probe. B, The expression levels of the HER-2 vs. H41 cDNAs were analyzed in a separate Northern blot experiment. The same set of breast tumor samples were used as in panel A except that the #16 tumor was substituted for the #14 due to depletion of the sample. Fifteen µg of total RNA was loaded in each lane except for tumor #15 for which only 5 µg were used because of lack of material. The blot was stripped as in A. For both A and B, ethidium bromide staining of 28 S ribosomal RNA is shown below the autoradiograms for RNA loading control.
Figure 16B:
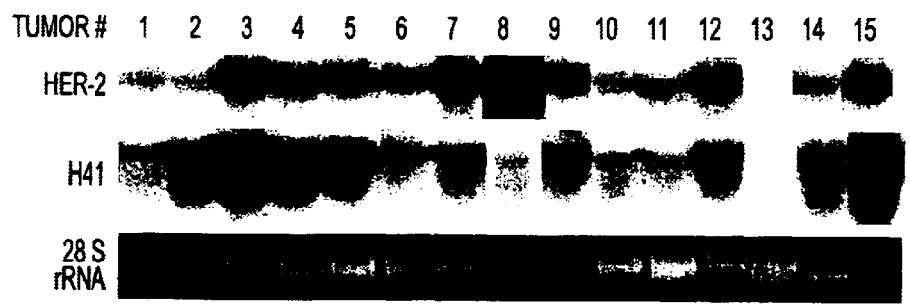

13. Differential Expression of Two of the Identified cDNAs in Primary Human Breast Cancer Samples To further confirm differential expression of the novel (or uncharacterized) cDNAs in actual human malignancies, we examined a panel of primary human breast cancer specimens by Northern blot analyses. Among these, we were able to detect clear signals on the tumor Northern blots for two of the tested clones, H37 and H41. Less success with the other cDNAs (i.e. C40, H13, H14, H17, H63) can be best explained with their relatively rare message level. For the H37 cDNA, 15 individual cancer samples were analyzed, and 8 of these (#3, 4, 5, 7, 8, 12, 14, 15) overexpress HER-2/neu (FIG. 16A). Seven of these eight tumors (88%) demonstrated overexpression of the H37 transcript, while only one of seven (14%) of the non-HER-2 overexpressors overexpresses this cDNA ($\square$=0.732, p<0.005) (FIG. 16A). For the H41 cDNA, 5 of 7 (71%) of the HER-2 overexpressing malignancies overexpress the gene while two of eight (25%) non-HER-2 overexpressors were found to have increased levels of this novel transcript ($\square$=0.464, p<0.075) (FIG. 16B). Tumor #8 did not express high levels of either H37 nor H41 despite its high HER-2 expression level. Overall, these data suggest that the above two novel genes may be contribute in some way to the phenotype associated with HER-2 overexpression. Further studies of this association are currently underway using greater numbers of tumor specimens.

14. Extension of HOMPS-Encoding Polynucleotides

Nucleic acid sequences of or FIG. 1, FIG. 3, FIG. 5, FIG. 7, FIG. 8 or FIG. 10 can be used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program to be 22–30 nucleotides i length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained.

Beginning with 40 pmol of each primer and the recommended concentrations of all other components of the kit, PCR is performed using the Peltier Thermal Cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.80%) agarose mini-gel to determine which reactions were successful in extending the sequence. Bands thought to contain the largest products are selected and removed from the gel. Further purification involves using a commercial gel extraction method such as the QIAQUICK kit (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2, times. Carb. The following day, several colonies are randomly picked from each plate and cultured in 150 μl of liquid LB/2, times. Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3, times.) containing 4 units of rTth DNA polymerase, a vector primer, and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions arc run on agarose gels together with molecular weight markers. The sizes of the PCR products are compared to the original partial cDNAs, and appropriate clones are selected, ligated into plasmid, and sequenced.

15. Labeling and Use of Hybridization Probes

Hybridization probes derived from FIG. 1, FIG. 3, FIG. 5, FIG. 7, FIG. 8 or FIG. 10 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of $^{32}$P adenosine triphosphate (Amersham Pharmacia Biotech) and T4 polynucleotide kinase DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1, times. saline sodium citrate and 0.5% sodium dodecyl sulfate. After XOMAT AR film Eastman Kodak Rochester, N.Y.) is exposed to the blots in a Phosphoimager cassette (Molecular Dynamics, Sunnyvale, Calif.) for several hours, hybridization patterns are compared visually.

16. Antisense or Complementary Sequences

Antisense molecules or nucleic acid sequences complementary to the HOMPS-encoding sequence, or any part thereof, are used to inhibit in vivo or in vitro expression of naturally occurring HOMPS. Although use of antisense oligonucleotides, comprising about 20 base-pairs, is specifically described, essentially the same procedure is used with larger cDNA fragments. An oligonucleotide based on the coding sequences of HOMPS, is used to inhibit expression of naturally occurring HOMPS. The complementary oligonucleotide is designed from the most uruque 5' sequence and used either to inhibit transcription by preventing promoter binding to the upstream nontranslated sequence or translation of an HOMPS-encoding transcript by preventing the ribosome from binding. Using an appropriate portion of the signal and 5' sequence of FIG. 1, FIG. 3, FIG. 5, FIG. 8 or FIG. 10, an effective antisense oligonucleotide includes any 15–20 nucleotides spanning the region which translates into the signal or 5' coding sequence of the polypeptide.

17. Expression of HOMPS

Expression of HOMPS is accomplished by subcloning the cDNAs into appropriate vectors and transforming the vectors into host cells. In this case, the cloning vector, pINCY1, previously used for the generation of the cDNA library is used to express HOMPS in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HOMPS into the bacterial growth media which can be used directly in the following assay for activity.

18. Production of HOMPS Specific Antibodies

HOMPS that is substantially purified using PAGE electrophoresis (Sambrook, supra), or other purification techniques, is used to immunize rabbits and to produce antibodies using standard protocols. The amino acid sequence deduced from FIG. 1, FIG. 3, FIG. 5, FIG. 8 or FIG. 10 is analyzed using LASERGENE software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleinidobenzoyl-N-hydroxysuccide ester (MBS; Ausubel et al., supra).

Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

19. Purification of Naturally Occurring HOMPS Using Specific Atitibodies

Naturally occurring or recombinant HOMPS is substantially purified by immunoaffinity chromatography using antibodies specific for HOMPS. An immunoaffinity column is constructed by covalently coupling HOMPS antibody to an activated chromatographic resin, such as CnBr-activated SEPHAROSE (Amersham Pharmacia Biotech). After the coupling, the resin is blocked and washed according to the manufacturer's instructions.

Media containing HOMPS is passed over the immunoaffinity column, and the column is washed under conditions that allow the preferential absorbance of HOMPS (e.g., high ionic strength buffers in the presence of detergent). The column is eluted under conditions that disrupt antibody/HOMPS binding (e.g., a buffer of pH 2–3 or a high concentration of a chaotrope, such as urea or thiocyanate ion), and HOMPS is collected.

20. Identification of Molecules Which Interact with HOMPS

HOMPS or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HOMPS, washed and any wells with labeled HOMPS complex are assayed. Data obtained using different concentrations of HOMPS are used to calculate values for the number, affinity, and association of HOMPS with the candidate molecules.

All publications and patents mentioned in the specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated polynucleotide that encodes an H41 polypeptide shown in SEQ ID NO: 6, wherein said polynucleotide is a probe for a nucleic acid comprising a sequence that is completely complementary to the sequence set forth in SEQ ID NO: 5.

2. A composition comprising a polynucleotide of claim 1.

3. A vector containing a polynucleotide of claim 1.

4. An isolated host cell containing the vector of claim 3.

5. The isolated polynucleotide of claim 1, wherein the probe is a deoxyribonucleic acid probe.

6. The isolated polynucleotide of claim 1, where the probe is a ribonucleic acid probe.

7. An isolated polynucleotide which is fully complementary to the polynucleotide according to claim 1.

8. An isolated nucleic acid comprising DNA which (a) hybridizes under stringent conditions with DNA encoding an H41 polypeptide comprising amino acids 1 to 258 of SEQ ID NO: 6, and (b) includes a polynucleotide sequence that is fully complementary to a polynucleotide sequence encoding a contiguous Lys-Lys-Lys-Lys (amino acid residues 18–21 of SEQ ID NO: 6) nuclear localization signal, wherein the stringent conditions are 0.015 M sodium chloride/0.0015 M sodium citrate/0.1% sodium dodecyl sulfate at 50° C., and further wherein said isolated nucleic acid is a probe for a polynucleotide comprising the sequence set forth in SEQ ID NO: 5.

9. The nucleic acid of claim 8, wherein the nucleic acid is labeled with a detectable marker.

10. An isolated nucleic acid which is fully complementary to the nucleic acid according to claim 8.

11. An isolated polynucleotide primer, wherein the primer consists of at least 10 consecutive nucleotides of SEQ ID NO: 5 or 10 consecutive nucleotides of the complete complement of SEQ ID NO: 5.

12. An isolated polynucleotide which is fully complementary to the primer according to claim 11.

13. An isolated polynucleotide comprising the sequence set forth in SEQ ID NO: 5.

* * * * *

UNITED STATES PATENT AND TRADEMARK OFFICE
CERTIFICATE OF CORRECTION

PATENT NO. : 6,770,477 B1 Page 1 of 1
DATED : August 3, 2004
INVENTOR(S) : Dennis J. Slamon et al.

It is certified that error appears in the above-identified patent and that said Letters Patent is hereby corrected as shown below:

Title page,
Item [73], Assignee, after "California", "Oailand" should read -- Oakland --.
Item [56], References Cited, OTHER PUBLICATIONS, after "E.F. Kirkness...cDNA", "Databas" should read -- Database --.

Signed and Sealed this

Twelfth Day of October, 2004

JON W. DUDAS
*Director of the United States Patent and Trademark Office*

UNITED STATES PATENT AND TRADEMARK OFFICE
CERTIFICATE OF CORRECTION

PATENT NO.         : 6,770,477 B1
APPLICATION NO. : 09/684405
DATED                : August 3, 2004
INVENTOR(S)      : Dennis J. Slamon et al.

It is certified that error appears in the above-identified patent and that said Letters Patent is hereby corrected as shown below:

Column 1

Line 9, please delete "The invention disclosed herein was made in part with Government support under Grant DAMD 17-94-J-4234 awarded by the Department of Defense and PO1 CA32737 awarded by the National Institutes of Health. The Government may have certain rights to the invention."

and insert

--This invention was made with Government support under Grant No. CA032737 awarded by the National Institutes of Health and Grant No. DAMD17-94-J-4234 awarded by the U.S. Army. The Government has certain rights in this invention.--

Signed and Sealed this

Twenty-seventh Day of October, 2009

David J. Kappos
*Director of the United States Patent and Trademark Office*

SEQUENCE LISTING

```
<160> NUMBER OF SEQ ID NOS:  14

<210> SEQ ID NO 1
<211> LENGTH: 1981
<212> TYPE: DNA
<213> ORGANISM: Homo Sapiens
<220> FEATURE:
<221> NAME/KEY: CDS
<222> LOCATION: (66)...(1526)

<400> SEQUENCE: 1
ggcacgagct gcgataatag cgaggcagca gtgcagcttt cagagggtcc gggctcagag        60 gggct atg att cgg agg gtt ctg ccg cac ggc atg ggc cgg ggc ctc ttg      110
      Met Ile Arg Arg Val Leu Pro His Gly Met Gly Arg Gly Leu Leu
        1               5                  10                  15 acc cgg agg cca ggc acg cgc aga gga ggc ttt tct ctg gac tgg gat        158
Thr Arg Arg Pro Gly Thr Arg Arg Gly Gly Phe Ser Leu Asp Trp Asp
                20                  25                  30 gga aag gtg tct gag att aag aag aag atc aag tcg atc ctg cct gga        206
Gly Lys Val Ser Glu Ile Lys Lys Lys Ile Lys Ser Ile Leu Pro Gly
            35                  40                  45 agg tcc tgt gat cta ctg caa gac acc agc cac ctg cct ccc gag cac        254
Arg Ser Cys Asp Leu Leu Gln Asp Thr Ser His Leu Pro Pro Glu His
        50                  55                  60 tcg gat gtg gtg atc gtg gga ggt ggg gtg ctt ggc ttg tct gtg gcc        302
Ser Asp Val Val Ile Val Gly Gly Gly Val Leu Gly Leu Ser Val Ala
    65                  70                  75 tat tgg ctg aag aag ctg gag agc aga cga ggt gct att cga gtg cta        350
Tyr Trp Leu Lys Lys Leu Glu Ser Arg Arg Gly Ala Ile Arg Val Leu
 80                  85                  90                  95 gtg gtg gaa cgg gac cac acg tat tca cag gcc tcc acc ggg ctc tca        398
Val Val Glu Arg Asp His Thr Tyr Ser Gln Ala Ser Thr Gly Leu Ser
                100                 105                 110 gta ggt ggg att tgt cag cag ttc tca ttg cct gag aac atc cag ctc        446
Val Gly Gly Ile Cys Gln Gln Phe Ser Leu Pro Glu Asn Ile Gln Leu
            115                 120                 125 tcc ctc ttt tca gcc agc ttt cta cgg aac atc aat gag tac ctg gcc        494
Ser Leu Phe Ser Ala Ser Phe Leu Arg Asn Ile Asn Glu Tyr Leu Ala
        130                 135                 140
```

```
gta gtc gat gct cct ccc ctg gac ctc cgg ttc aac ccc tcg ggc tac      542
Val Val Asp Ala Pro Pro Leu Asp Leu Arg Phe Asn Pro Ser Gly Tyr
145                 150                 155 ctc ttg ctg gct tca gaa aag gat gct gca gcc atg gag agc aac gtg      590
Leu Leu Leu Ala Ser Glu Lys Asp Ala Ala Ala Met Glu Ser Asn Val
160                 165                 170                 175 aaa gtg cag agg cag gag gga gcc aaa gtt tct ctg atg tct cct gat      638
Lys Val Gln Arg Gln Glu Gly Ala Lys Val Ser Leu Met Ser Pro Asp
                180                 185                 190 cag ctt cgg aac aag ttt ccc tgg ata aac aca gag gga gtg gct ttg      686
Gln Leu Arg Asn Lys Phe Pro Trp Ile Asn Thr Glu Gly Val Ala Leu
            195                 200                 205 gcg tct tat ggg atg gag gac gaa ggt tgg ttt gac ccc tgg tgt ctg      734
Ala Ser Tyr Gly Met Glu Asp Glu Gly Trp Phe Asp Pro Trp Cys Leu
        210                 215                 220 ctc cag ggg ctt cgg cga aag gtc cag tcc ttg gga gtc ctt ttc tgc      782
Leu Gln Gly Leu Arg Arg Lys Val Gln Ser Leu Gly Val Leu Phe Cys
    225                 230                 235 cag gga gag gtg aca cgt ttt gtc tct tca tct caa cgc atg ttg acc      830
Gln Gly Glu Val Thr Arg Phe Val Ser Ser Ser Gln Arg Met Leu Thr
240                 245                 250                 255 aca gat gac aaa gcg gtg gtc ttg aaa agg atc cat gaa gtc cat gtg      878
Thr Asp Asp Lys Ala Val Val Leu Lys Arg Ile His Glu Val His Val
                260                 265                 270 aag atg gac cgc agc ctg gag tac cag cct gtg gaa tgc gcc att gtg      926
Lys Met Asp Arg Ser Leu Glu Tyr Gln Pro Val Glu Cys Ala Ile Val
                275                 280                 285 atc aac gca gcc gga gcc tgg tct gcg caa atc gca gca ctg gct ggt      974
Ile Asn Ala Ala Gly Ala Trp Ser Ala Gln Ile Ala Ala Leu Ala Gly
            290                 295                 300 gtt gga gag ggg ccg cct ggc acc ctg cag ggc acc aag cta cct gtg     1022
Val Gly Glu Gly Pro Pro Gly Thr Leu Gln Gly Thr Lys Leu Pro Val
        305                 310                 315 gag ccg agg aaa agg tat gtg tat gtg tgg cac tgc ccc cag gga cca     1070
Glu Pro Arg Lys Arg Tyr Val Tyr Val Trp His Cys Pro Gln Gly Pro
320                 325                 330                 335 ggc cta gag act ccg ctt gtt gca gac acc agt gga gcc tat ttt cgc     1118
Gly Leu Glu Thr Pro Leu Val Ala Asp Thr Ser Gly Ala Tyr Phe Arg
                340                 345                 350 cgg gaa gga tta ggt agc aac tac cta ggt ggt cgt agc ccc act gag     1166
Arg Glu Gly Leu Gly Ser Asn Tyr Leu Gly Gly Arg Ser Pro Thr Glu
            355                 360                 365 cag gaa gaa ccg gac ccg gcg aac ctg gaa gtg gac cat gat ttc ttc     1214
Gln Glu Glu Pro Asp Pro Ala Asn Leu Glu Val Asp His Asp Phe Phe
        370                 375                 380 cag gac aag gtg tgg ccc cat ttg gcc ctg agg gtc cca gct ttt gag     1262
Gln Asp Lys Val Trp Pro His Leu Ala Leu Arg Val Pro Ala Phe Glu
385                 390                 395 act ctg aag gtt cag agc gcc tgg gcc ggc tat tac gac tac aac acc     1310
Thr Leu Lys Val Gln Ser Ala Trp Ala Gly Tyr Tyr Asp Tyr Asn Thr
400                 405                 410                 415 ttt gac cag aat ggc gtg gtg ggc ccc cac ccg cta gtt gtc aac atg     1358
Phe Asp Gln Asn Gly Val Val Gly Pro His Pro Leu Val Val Asn Met
                420                 425                 430 tac ttt gct act ggc ttc agt ggt cac ggg ctc cag cag gcc cct ggc     1406
Tyr Phe Ala Thr Gly Phe Ser Gly His Gly Leu Gln Gln Ala Pro Gly
            435                 440                 445 att ggg cga gct gta gca gag atg gta ctg aag ggc agg ttc cag acc     1454
Ile Gly Arg Ala Val Ala Glu Met Val Leu Lys Gly Arg Phe Gln Thr
        450                 455                 460
```

```
atc gac ctg agc ccc ttc ctc ttt acc cgc ttt tac ttg gga gag aag    1502
Ile Asp Leu Ser Pro Phe Leu Phe Thr Arg Phe Tyr Leu Gly Glu Lys
    465                 470                 475 atc cag gag aac aac atc atc tga gcatgtgtgc tctgcactgg ctccactggc   1556
Ile Gln Glu Asn Asn Ile Ile *
480                 485 ttgcatcctg gctgtgttca cagccttgtt tgctgcttcc atcttcccca gtactgtgcc   1616
aggccttctc cccctcccca gtgtcctctc ctctcaggca ggccattgca cccatatggc   1676
tgggcaggca caggcagtga ggccgaggcc aatagcgagt gatgagcggg atcctaggac   1736
tgatctgtag cccatgctga tgtcacccac cagggcaatc catctggagg cctgagcacc   1796
ctggcccagg actggcttca tcctggcact gaccaggaaa gactgcctct gaccctctta   1856
gcagacagag cccaggcatg ggagcactct ggggcagcct ggctcaggtt tattgatttt   1916
cgtctgttta ccctatccat taatcaatac atgtaattaa ctcctaaaaa aaaaaaaaaa   1976
aaaaa                                                              1981
```

<210> SEQ ID NO 2
<211> LENGTH: 486
<212> TYPE: PRT
<213> ORGANISM: Homo Sapiens

<400> SEQUENCE: 2

```
Met Ile Arg Arg Val Leu Pro His Gly Met Gly Arg Gly Leu Leu Thr
1               5                   10                  15

Arg Arg Pro Gly Thr Arg Gly Gly Phe Ser Leu Asp Trp Asp Gly
            20                  25                  30

Lys Val Ser Glu Ile Lys Lys Lys Ile Lys Ser Ile Leu Pro Gly Arg
        35                  40                  45

Ser Cys Asp Leu Leu Gln Asp Thr Ser His Leu Pro Pro Glu His Ser
    50                  55                  60

Asp Val Val Ile Val Gly Gly Val Leu Gly Leu Ser Val Ala Tyr
65                  70                  75                  80

Trp Leu Lys Lys Leu Glu Ser Arg Arg Gly Ala Ile Arg Val Leu Val
                85                  90                  95

Val Glu Arg Asp His Thr Tyr Ser Gln Ala Ser Thr Gly Leu Ser Val
            100                 105                 110

Gly Gly Ile Cys Gln Gln Phe Ser Leu Pro Glu Asn Ile Gln Leu Ser
        115                 120                 125

Leu Phe Ser Ala Ser Phe Leu Arg Asn Ile Asn Glu Tyr Leu Ala Val
    130                 135                 140

Val Asp Ala Pro Leu Asp Leu Arg Phe Asn Pro Ser Gly Tyr Leu
145                 150                 155                 160

Leu Leu Ala Ser Glu Lys Asp Ala Ala Met Glu Ser Asn Val Lys
                165                 170                 175

Val Gln Arg Gln Glu Gly Ala Lys Val Ser Leu Met Ser Pro Asp Gln
            180                 185                 190

Leu Arg Asn Lys Phe Pro Trp Ile Asn Thr Glu Gly Val Ala Leu Ala
        195                 200                 205

Ser Tyr Gly Met Glu Asp Glu Gly Trp Phe Asp Pro Trp Cys Leu Leu
    210                 215                 220

Gln Gly Leu Arg Arg Lys Val Gln Ser Leu Gly Val Leu Phe Cys Gln
225                 230                 235                 240

Gly Glu Val Thr Arg Phe Val Ser Ser Ser Gln Arg Met Leu Thr Thr
```

-continued

```
                        245                 250                 255
Asp Asp Lys Ala Val Val Leu Lys Arg Ile His Glu Val His Val Lys
            260                 265                 270
Met Asp Arg Ser Leu Glu Tyr Gln Pro Val Glu Cys Ala Ile Val Ile
            275                 280                 285
Asn Ala Ala Gly Ala Trp Ser Ala Gln Ile Ala Ala Leu Ala Gly Val
            290                 295                 300
Gly Glu Gly Pro Pro Gly Thr Leu Gln Gly Thr Lys Leu Pro Val Glu
305                 310                 315                 320
Pro Arg Lys Arg Tyr Val Tyr Val Trp His Cys Pro Gln Gly Pro Gly
            325                 330                 335
Leu Glu Thr Pro Leu Val Ala Asp Thr Ser Gly Ala Tyr Phe Arg Arg
            340                 345                 350
Glu Gly Leu Gly Ser Asn Tyr Leu Gly Gly Arg Ser Pro Thr Glu Gln
            355                 360                 365
Glu Glu Pro Asp Pro Ala Asn Leu Glu Val Asp His Asp Phe Phe Gln
            370                 375                 380
Asp Lys Val Trp Pro His Leu Ala Leu Arg Val Pro Ala Phe Glu Thr
385                 390                 395                 400
Leu Lys Val Gln Ser Ala Trp Ala Gly Tyr Tyr Asp Tyr Asn Thr Phe
            405                 410                 415
Asp Gln Asn Gly Val Val Gly Pro His Pro Leu Val Val Asn Met Tyr
            420                 425                 430
Phe Ala Thr Gly Phe Ser Gly His Gly Leu Gln Gln Ala Pro Gly Ile
            435                 440                 445
Gly Arg Ala Val Ala Glu Met Val Leu Lys Gly Arg Phe Gln Thr Ile
            450                 455                 460
Asp Leu Ser Pro Phe Leu Phe Thr Arg Phe Tyr Leu Gly Glu Lys Ile
465                 470                 475                 480
Gln Glu Asn Asn Ile Ile
            485
```

<210> SEQ ID NO 3
<211> LENGTH: 1750
<212> TYPE: DNA
<213> ORGANISM: Homo Sapiens

<400> SEQUENCE: 3

| | | | | | |
|---|---|---|---|---|---|
| ggcacgagcg | gggacggagc | gagccggcgc | cagggcccct | cgggccggga | agaggggaag | 60 |
| gggagcgagg | ttgatgcccg | gcggagggc | gagcgcggcg | tctggccggc | ttctcaccgc | 120 |
| cgcggagcaa | agagggtccc | gggaagcggc | agggtcggcg | tccaggagcg | gcttcggggg | 180 |
| ctccggcggc | ggcagaggcg | gagcaagcgg | ccccgggtcc | gggagcggag | gccctggggg | 240 |
| ccccgcgggc | aggatgagct | tgaccccgaa | ggagctctcg | agcctgctga | gcatcatatc | 300 |
| ggaggaggcg | gcggcggca | gcaccttcga | gggcctgtcc | accgccttcc | accactactt | 360 |
| cagcaaggcc | gaccacttcc | gcctgggctc | ggtgctcgtc | atgctgctcc | agcagcccga | 420 |
| cctgctgcct | agcgcggcgc | agcgcctcac | ggcgctctac | ctgctctggg | agatgtaccg | 480 |
| caccgagccg | ctggccgcca | cccccttcgc | cgccagcttc | gcgcacctgc | tcaaccccgc | 540 |
| gccgcccgcc | cgcggcggcc | aggaacccga | ccgcctccg | ctctcaggat | ttttacctcc | 600 |
| tataactcca | ccagaaaagt | ttttctttc | ccagctgatg | ctggcacccc | cacgggaact | 660 |
| cttcaaaaag | acgcctcgcc | agattgcact | gatggacgtt | ggaaacatgg | gccagtctgt | 720 |

-continued

```
ggacattagt gggcttcagt tagccttggc cgaacgccaa tctgaattgc caacgcaaag    780
caaagcgagc ttccccagta ttctcagtga cccagacccg gattcttcta attctggatt    840
tgacagctca gttgcctctc agatcacaga agctttagtc agcggaccaa agccacctat    900
tgaaagccat tttcgaccag agtttattcg tccaccgcct ccactccaca tttgtgagga    960
tgaacttgct tggctaaacc ccacggagcc tgaccacgcg atccagtggg ataaatcgat   1020
gtgtgttaag aatagcactg gtgtggagat caaacgaata atggccaaag ccttcaaaag   1080
ccccttatcc tctccccaac aaacacagct acttggtgag ttggaaaaag accccaaact   1140
tgtctaccat attggcctca ccccagccaa acttcctgac cttgtggaaa caacccttt    1200 agtcgctata gaaatgttgc tgaaattaat gcagtcaagc cagatcactg agtatttctc   1260
tgtcctggtc aatatggaca tgtctttaca ttcaatggaa gttgtaaatc gactaactac   1320
agctgttgat ctacctcctg aatttattca cctttatata tcaaattgca tctctacttg   1380
tgaacagatt aaggataaat atatgcagaa tcggttggtg cgtcttgtgt gtgtgttct    1440 ccaatccttg atccgtaaca aaattattaa tgtacaggat ttgtttatag aagtgcaggc   1500
attctgtatt gaattcagta ggatacgaga agctgctggt cttttccggt tgttgaagac   1560
attggatact ggggaaacac cttctgagac caaaatgtca aaataatacc tcatcagaac   1620
catcccatcc attcactgtt cagctgtact gtgatttagt ttttacaccg ttaaaaccct   1680
gagtggattg cttggtttaa tgcatataaa cagtacttta tctacttaaa gcaaaaaaaa   1740
aaaaaaaaaa                                                         1750
```

<210> SEQ ID NO 4
<211> LENGTH: 510
<212> TYPE: PRT
<213> ORGANISM: Homo Sapiens

<400> SEQUENCE: 4

```
Met Pro Gly Gly Gly Ala Ser Ala Ala Ser Gly Arg Leu Leu Thr Ala
  1               5                  10                  15

Ala Glu Gln Arg Gly Ser Arg Glu Ala Ala Gly Ser Ala Ser Arg Ser
             20                  25                  30

Gly Phe Gly Gly Ser Gly Gly Arg Gly Gly Ala Ser Gly Pro Gly
         35                  40                  45

Ser Gly Ser Gly Gly Pro Gly Gly Pro Ala Gly Arg Met Ser Leu Thr
     50                  55                  60

Pro Lys Glu Leu Ser Ser Leu Ser Ile Ile Ser Glu Glu Ala Gly
 65                  70                  75                  80

Gly Gly Ser Thr Phe Glu Gly Leu Ser Thr Ala Phe His His Tyr Phe
                 85                  90                  95

Ser Lys Ala Asp His Phe Arg Leu Gly Ser Val Leu Val Met Leu Leu
            100                 105                 110

Gln Gln Pro Asp Leu Leu Pro Ser Ala Ala Gln Arg Leu Thr Ala Leu
        115                 120                 125

Tyr Leu Leu Trp Glu Met Tyr Arg Thr Glu Pro Leu Ala Ala Asn Pro
    130                 135                 140

Phe Ala Ala Ser Phe Ala His Leu Leu Asn Pro Ala Pro Ala Arg
145                 150                 155                 160

Gly Gly Gln Glu Pro Asp Arg Pro Leu Ser Gly Phe Leu Pro Pro
                165                 170                 175

Ile Thr Pro Pro Glu Lys Phe Phe Leu Ser Gln Leu Met Leu Ala Pro
            180                 185                 190
```

```
Pro Arg Glu Leu Phe Lys Lys Thr Pro Arg Gln Ile Ala Leu Met Asp
        195                 200                 205

Val Gly Asn Met Gly Gln Ser Val Asp Ile Ser Gly Leu Gln Leu Ala
    210                 215                 220

Leu Ala Glu Arg Gln Ser Glu Leu Pro Thr Gln Ser Lys Ala Ser Phe
225                 230                 235                 240

Pro Ser Ile Leu Ser Asp Pro Asp Ser Ser Asn Ser Gly Phe
                245                 250                 255

Asp Ser Ser Val Ala Ser Gln Ile Thr Glu Ala Leu Val Ser Gly Pro
                260                 265                 270

Lys Pro Pro Ile Glu Ser His Phe Arg Pro Glu Phe Ile Arg Pro Pro
            275                 280                 285

Pro Pro Leu His Ile Cys Glu Asp Leu Ala Trp Leu Asn Pro Thr
        290                 295                 300

Glu Pro Asp His Ala Ile Gln Trp Asp Lys Ser Met Cys Val Lys Asn
305                 310                 315                 320

Ser Thr Gly Val Glu Ile Lys Arg Ile Met Ala Lys Ala Phe Lys Ser
                325                 330                 335

Pro Leu Ser Ser Pro Gln Gln Thr Gln Leu Leu Gly Glu Leu Glu Lys
            340                 345                 350

Asp Pro Lys Leu Val Tyr His Ile Gly Leu Thr Pro Ala Lys Leu Pro
            355                 360                 365

Asp Leu Val Glu Asn Asn Pro Leu Val Ala Ile Glu Met Leu Leu Lys
        370                 375                 380

Leu Met Gln Ser Ser Gln Ile Thr Glu Tyr Phe Ser Val Leu Val Asn
385                 390                 395                 400

Met Asp Met Ser Leu His Ser Met Glu Val Val Asn Arg Leu Thr Thr
                405                 410                 415

Ala Val Asp Leu Pro Pro Glu Phe Ile His Leu Tyr Ile Ser Asn Cys
            420                 425                 430

Ile Ser Thr Cys Glu Gln Ile Lys Asp Lys Tyr Met Gln Asn Arg Leu
        435                 440                 445

Val Arg Leu Val Cys Val Phe Leu Gln Ser Leu Ile Arg Asn Lys Ile
450                 455                 460

Ile Asn Val Gln Asp Leu Phe Ile Glu Val Gln Ala Phe Cys Ile Glu
465                 470                 475                 480

Phe Ser Arg Ile Arg Glu Ala Ala Gly Leu Phe Arg Leu Leu Lys Thr
                485                 490                 495

Leu Asp Thr Gly Glu Thr Pro Ser Glu Thr Lys Met Ser Lys
            500                 505                 510

<210> SEQ ID NO 5
<211> LENGTH: 3346
<212> TYPE: DNA
<213> ORGANISM: Homo Sapiens

<400> SEQUENCE: 5
ggcacgagct ggctcgcgcg tgccttttcc cctcaggttg tggggagagc ggaatcctgc      60
tccgccgtcg cagcagcagc ggcagccccg gcagcctcgg gcgacagcgg cggcgcgcga     120
gcccccgggc ggaccgtacc accgctcgcc agcacgcagg gggagccgcc cgtctcgccg     180
cgcacgcctc ggcgaccccg cggggctgag gcgtcgccgc gcccggcagc gtgagcgcag     240
agccggcctc gaccccgagc tcggagcccc gcgggccgcg cccgccgccg gccccaccca     300
```

-continued

```
tccgggtcga ggaggccgag gccatggctg agacggagga gcggagcctg gacaacttct    360
ttgccaagag ggacaagaag aagaagaagg agcggagcaa ccgggcggcg agtgccgcgg    420
gcgcagcggg cagcgccggc ggaagcagtg gagccgcggg tgcggcgggc ggcgggggcgg   480 gcgcggggac ccggccgggt gacggcggga ccgccagcgc gggggctgcg ggcccagggg    540
ccgccaccaa ggctgtgacg aaggacgaag atgaatggaa agaattggag caaaaagagg    600
ttgattacag cggcctcagg gttcaggcaa tgcaaataag cagtgaaaag gaagaagacg    660
ataatgaaaa gagacaagat ccaggtgata actgggaaga aggtggaggt ggtggtggag    720
gtatggaaaa atcttcaggt ccctggaata aaacagctcc agtacaagca cctcctgctc    780
cagtaattgt tacagaaacc ccagaaccag cgatgactag tggtgtgtat aggcctcctg    840
gggccaggtt aaccacaaca aggaaaacac cacaaggacc accagaaatc tacagtgata    900
cacagttccc atccctgcag tcaactgcca agcatgtaga aagccggaag gataaagaaa    960
tggagaagag ctttgaagta gtaagacaca aaaatagagg tagggatgag gtttcaaaaa   1020
accaggccct taaacttcag ctagacaacc aatatgctgt gcttgaaaat cagaaaagca   1080
gccactcaca atacaattaa ggaatgggct ttgctaaccc ttctgaggta actagactgc   1140
agctaaccac caccaacagc cattcatcat ctgatctctg ctggatctac agacaccgat   1200
gcagaccact cgatttcatg accggcccta ttgcactatg aagttaaag tgtcacgact    1260 gctctatgca tattggattt aggggaattt tcattgttac ataaatgtgt gaactagttt   1320
caacagtgtt ctttcatatt tactctgcaa atacaaaaaa ccaaaacctg cagccagtgg   1380
tcatttcaaa atcttttat gttcagatac tgagccttca taagggttga ctacctcaga   1440
tttgctgcac tcattgtgga cttcatgtgg atcacaactt ctggataaga agattacaac   1500
tattaagtgt cgatgtgaac cttgcaacca gctctactgg attcttatca gaaatcctgc   1560
ataaaaagtc agccatctgg gttctgatct gctgtaaaag atgaagattt aagtgacctt   1620
aattaacctg tcctgtgccc tacccttaag gaatactctc tgtagtaggc tgttgttata   1680
ttagacttcc tggaacacac cgctgaaaag aactgatgtg ttcagatcat ctgtgtaggg   1740
ctgtgatttg taatttaaac taattgtatt ctgaggtaac cacaaaataa attcaaccaa   1800 actgggtcc accaagtggg ggaagggaa gggagagaat aatcttgggg gttttttttt     1860
ttggtaattt ttttatttgg atagtgcttt tttgttttgt ttttgttctg cattaaggcc   1920
ttttttgctt tgacttgaaa taagttcttt gacagagcat attgcttggt taattaagta   1980
acctaaagta tgcattagga ttgtgaaatg tctcgtgagt atgccaatcc tgagggtgga   2040
accaaatagc ctttgatgaa aagggcagtg gattctggag gctctacttc aggtgctgct   2100
ataatgcctc atcaatcag gactaaattg tgtaggaaac tgcagtggga agaatatgct    2160
ttctgctcag gctaagaggg tcactgatct gtccttagaa attcagagta acatgagcaa   2220
aacctcagct aaaacccatt taagtggcat ggattgtgca tgatctttga taagaattcc   2280
tcatgtactt gtgcctagtt tttcaaggta ttggctgttc tatagatgca gtgattgtcc   2340
cagctagctc tgttaccagc cttttggtgt gtctttatgt tcatttggag agtcagggcg   2400
aaagacaggt gatgtagcac ttctgttttt aataattatt gcttaaaata cctattaata   2460
gttttgggtc atttaaaggg acttgaggaa gctacccagg attacagaag agtgtccacc   2520
taacaagatg gtctggcagt ttcctagttt tgtatctggt tcaatagaaa tatgtgaaag   2580
tggtaatgtc atcatttgat gcagagtccg ggtttctcta taataaatcc ctttgccaaa   2640
tgcatgagtt gcagacttgc tactggcaag agtgaagcaa gtgggtgagt aaaactattt   2700
```

-continued

```
tgacgtggga gcgttttcag ataggagttt agtcttgacg aaagtgtccg tgcaggaatt      2760
ggactccgag gagggttaca gtatctcctg acgggacctg ccactcgcat ctgggcaatg      2820
ttgacatttg aggtggcagg caggatgcct gccttctaat atatttgggt gagtaactga      2880
gccagccaag ggaaggttga atgattaaat cagaaatggg attcttggta aactgaagac      2940
ttttatttgg gaatgaaaaa ccttaaaaaa atctcttcat cgttgaactg tgcattttcc      3000
ctgcattttt tcccaacaaa attttgttgg gggttatgtt actgaagaat aacagatga       3060 gtaagtggag gtgttatgta aaggcatatt gtactcgaaa tctgaagacc tgcagcagat      3120
ttaaattaca actcttgtta taacttttta aaagattgtg aaaatatcaa aatataaatg      3180
aatcaagttt taatatactg tatgatgggt ggatgaggct gtccattgta ccatttgttt      3240
gaattctcag gcatggtttg gcagtgcaag aattctgtaa cattaacaaa ttcaataaaa      3300
agtaaatata tggaaaaaaa aaaaaaaaaa aaaaaaaaa aaaaaa                      3346
```

```
<210> SEQ ID NO 6
<211> LENGTH: 258
<212> TYPE: PRT
<213> ORGANISM: Homo Sapiens

<400> SEQUENCE: 6

Met Ala Glu Thr Glu Glu Arg Ser Leu Asp Asn Phe Phe Ala Lys Arg
 1               5                  10                  15

Asp Lys Lys Lys Lys Glu Arg Ser Asn Arg Ala Ala Ser Ala Ala
            20                  25                  30

Gly Ala Ala Gly Ser Ala Gly Gly Ser Ser Gly Ala Ala Gly Ala Ala
        35                  40                  45

Gly Gly Gly Ala Gly Ala Gly Thr Arg Pro Gly Asp Gly Gly Thr Ala
    50                  55                  60

Ser Ala Gly Ala Ala Gly Pro Gly Ala Ala Thr Lys Ala Val Thr Lys
65                  70                  75                  80

Asp Glu Asp Glu Trp Lys Glu Leu Glu Gln Lys Glu Val Asp Tyr Ser
                85                  90                  95

Gly Leu Arg Val Gln Ala Met Gln Ile Ser Ser Glu Lys Glu Glu Asp
            100                 105                 110

Asp Asn Glu Lys Arg Gln Asp Pro Gly Asp Asn Trp Glu Glu Gly Gly
        115                 120                 125

Gly Gly Gly Gly Gly Met Glu Lys Ser Ser Gly Pro Trp Asn Lys Thr
    130                 135                 140

Ala Pro Val Gln Ala Pro Pro Ala Pro Val Ile Val Thr Glu Thr Pro
145                 150                 155                 160

Glu Pro Ala Met Thr Ser Gly Val Tyr Arg Pro Pro Gly Ala Arg Leu
                165                 170                 175

Thr Thr Thr Arg Lys Thr Pro Gln Gly Pro Pro Glu Ile Tyr Ser Asp
            180                 185                 190

Thr Gln Phe Pro Ser Leu Gln Ser Thr Ala Lys His Val Glu Ser Arg
        195                 200                 205

Lys Asp Lys Glu Met Glu Lys Ser Phe Glu Val Val Arg His Lys Asn
    210                 215                 220

Arg Gly Arg Asp Glu Val Ser Lys Asn Gln Ala Leu Lys Leu Gln Leu
225                 230                 235                 240

Asp Asn Gln Tyr Ala Val Leu Glu Asn Gln Lys Ser Ser His Ser Gln
                245                 250                 255
```

Tyr Asn

<210> SEQ ID NO 7
<211> LENGTH: 2068
<212> TYPE: DNA
<213> ORGANISM: Homo Sapiens

<400> SEQUENCE: 7

| | | | | | |
|---|---|---|---|---|---|
| ggcacgaggt | ggcatagcat | aaccacagta | agaacagaac | agatattcag | cagaaaactt | 60 |
| tttatactct | aattcttttt | tttttttttt | ttgagacaga | gttttagtct | tgtttcccag | 120 |
| gctggagtgc | aatggcacaa | tcttggctca | ctgcaacctc | cgcctcctgg | gttcaggcaa | 180 |
| ttttcctgcc | tcagcctccc | aagtagctgg | gattacaggc | acccaccacc | atgcccagct | 240 |
| aattttttgta | ttttttaatag | agagctaata | attgtatatt | taataaagac | gggtttcacc | 300 |
| atgttggcca | ggctggtctt | gaactcctga | cctcaggtga | tcctcctgca | ttggcctccc | 360 |
| aaagtgctgg | aattccaggc | atgagccact | gcgcccagtc | tacacactaa | ttcttgttag | 420 |
| cccaacagct | gttctgttct | atctacccct | catttcacgc | tcaaggagtc | atacctagaa | 480 |
| tagttacaca | caagagggaa | actggaagcc | aaacactgta | cagtattgtg | tagaaagtca | 540 |
| cctccctact | cctttttattt | tacatgagtg | ctgatgtgtt | ttggcagatg | agctttcagc | 600 |
| tgaggcctga | tggaaattga | gataacctgc | aaagacataa | cagtatttat | gagttatatc | 660 |
| ttagttcttg | aaattgtgga | atgcatgatt | gacaatatat | ttttaatttt | tattttttca | 720 |
| agtaatacca | gtactgttta | actatagcca | gaactggcta | aaatttttat | attttcagag | 780 |
| ttgaagttgg | tgaagacatt | catgatttaa | acaccagatc | ctgaaagggg | ttaaatctac | 840 |
| tttgaaatga | atctgcaatc | agtatttcaa | agcttttctg | gtaattttag | tgatcttatt | 900 |
| tgattagact | ttttcagaag | tactaaataa | ggaattttaa | caggtttttta | ttaatgcaca | 960 |
| gataaataga | agtacagtga | ggtctatagc | cattttatta | aaatagctta | aaagtttgta | 1020 |
| aaaaaatgaa | tctttgtaat | tacttaatat | gttagttaag | aacccgtcaa | gcttatattt | 1080 |
| gctagactta | caaattattt | taaatgcatt | tatcttttt | gacactattc | agtggaatgt | 1140 |
| gtaagctagc | taattcttgt | tttctgattt | aaagcacttt | taaatcttat | cctgcccccct | 1200 |
| aaaaacaaaa | ggttttgatc | acaagggaa | atttaagatt | gttaaccctg | tttttcagaa | 1260 |
| gggctactgt | taattgcaca | taaacatgaa | atgtgttttc | ccctgtgtac | taacacattc | 1320 |
| taggcaaaat | tcaaacttat | agtggtaaag | aaacaggttg | ttcacttgct | gaggtgcaaa | 1380 |
| aattcttaag | acttctgttt | gaaattgctc | aatgactagg | aaaagatgta | gtagtttact | 1440 |
| aaaattgttt | ttctaccata | tcaaattaaa | caattcatgc | ctttttaggg | tcaggcctac | 1500 |
| aatgaatagg | tatggtggtt | tcacagaatt | ttaaaataga | gttaaaggga | agtgatgtac | 1560 |
| atttcggggg | cattagggta | gggagatgaa | tcaaaaaata | cccctagtaa | tgctttatat | 1620 |
| tttaatactg | caaaagcttt | acaaatggaa | accatgcaat | tacctgcctt | agttcttttg | 1680 |
| tcataaaaac | aatcacttgg | ttggttgtat | tgtagctatt | acttatacag | caacatttct | 1740 |
| tcaattagca | gtctagacat | tttataaaca | gaaatcttgg | accaattgat | aatatttctg | 1800 |
| actgtattaa | tattttagtg | ctataaaata | ctatgtgaat | ctcttaaaaa | tctgacattt | 1860 |
| tacagtctgt | attagacata | ctgttttttat | aatgttttac | ttctgcctta | agatttaggt | 1920 |
| tttttaaatg | tattttttgcc | ctgaattaag | tgttaatttg | atggaaactc | tgcttttaaa | 1980 |
| atcatcattt | actgggttct | aataaattaa | aaattaaact | tgtaaaaaaa | aaaaaaaaa | 2040 |
| aaaaaaaaaa | aaaaaaaaa | aaaaaaa | | | | 2068 |

-continued

<210> SEQ ID NO 8
<211> LENGTH: 1027
<212> TYPE: DNA
<213> ORGANISM: Homo Sapiens

<400> SEQUENCE: 8

| | | | | | |
|---|---|---|---|---|---|
| ggcacgaggt | cccaccttgt | ggaggatgga | ggtgaccggg | gacgccgggg | taccagaatc | 60 |
| tggcgagatc | cggactctaa | agccgtgtct | gctgcgccgc | aactacagcc | gcgaacagca | 120 |
| cggcgtggcc | gcctcctgcc | tcgaagacct | gaggagcaag | gcctgtgaca | ttctggccat | 180 |
| tgataagtcc | ctgacaccag | tcaccctggt | cctggcagag | gatggcacca | tagtggatga | 240 |
| tgacgattac | tttctgtgtc | taccttccaa | tactaagttt | gtggcattgg | ctagtaatga | 300 |
| gaaatgggca | tacaacaatt | cagatggagg | tacagcttgg | atttcccaag | agtcctttga | 360 |
| tgtagatgaa | acagacagcg | gggcagggtt | gaagtggaag | aatgtggcca | ggcagctgaa | 420 |
| agaagatctg | tccagcatca | tcctcctatc | agaggaggac | tccagatgc | ttgttgacgc | 480 |
| tccctgctca | gacctggctc | aggaactacg | tcagagttgt | gccaccgtcc | agcggctgca | 540 |
| gcacacactc | caacaggtgc | ttgaccaaag | agaggaagtg | cgtcagtcca | agcagctcct | 600 |
| gcagctgtac | ctccaggctt | tggagaaaga | gggcagcctc | ttgtcaaagc | aggaagagtc | 660 |
| caaagctgcc | tttggtgagg | aggtggatgc | agtagacacg | gtatcagca | gagagacctc | 720 |
| ctcggacgtt | gcgctggcga | gccacatcct | tactgcactg | agggagaagc | aggctccaga | 780 |
| gctgagctta | tctagtcagg | atttggaggt | gggcggaaac | cagggtcact | gagctacaga | 840 |
| ggaggacatg | ccctgggatg | tagtagtatc | atgcagaggt | gtgtgggccc | ttttgttcac | 900 |
| ctctgcagac | tgtgaatcct | agctgccagt | ttgcctatta | tatgccaagg | catttgcaaa | 960 |
| aatctcatta | atctaaatca | aaatagcttt | aagaaaaat | gcaaaaaaaa | aaaaaaaaa | 1020 |
| aaaaaaa | | | | | | 1027 |

<210> SEQ ID NO 9
<211> LENGTH: 268
<212> TYPE: PRT
<213> ORGANISM: Homo Sapiens

<400> SEQUENCE: 9

Met Glu Val Thr Gly Asp Ala Gly Val Pro Glu Ser Gly Glu Ile Arg
 1               5                  10                  15

Thr Leu Lys Pro Cys Leu Leu Arg Arg Asn Tyr Ser Arg Glu Gln His
            20                  25                  30

Gly Val Ala Ala Ser Cys Leu Glu Asp Leu Arg Ser Lys Ala Cys Asp
        35                  40                  45

Ile Leu Ala Ile Asp Lys Ser Leu Thr Pro Val Thr Leu Val Leu Ala
    50                  55                  60

Glu Asp Gly Thr Ile Val Asp Asp Asp Tyr Phe Leu Cys Leu Pro
65                  70                  75                  80

Ser Asn Thr Lys Phe Val Ala Leu Ala Ser Asn Glu Lys Trp Ala Tyr
                85                  90                  95

Asn Asn Ser Asp Gly Gly Thr Ala Trp Ile Ser Gln Glu Ser Phe Asp
            100                 105                 110

Val Asp Glu Thr Asp Ser Gly Ala Gly Leu Lys Trp Lys Asn Val Ala
        115                 120                 125

Arg Gln Leu Lys Glu Asp Leu Ser Ser Ile Ile Leu Leu Ser Glu Glu
    130                 135                 140

```
Asp Leu Gln Met Leu Val Asp Ala Pro Cys Ser Asp Leu Ala Gln Glu
145                 150                 155                 160

Leu Arg Gln Ser Cys Ala Thr Val Gln Arg Leu Gln His Thr Leu Gln
            165                 170                 175

Gln Val Leu Asp Gln Arg Glu Glu Val Arg Gln Ser Lys Gln Leu Leu
        180                 185                 190

Gln Leu Tyr Leu Gln Ala Leu Glu Lys Glu Gly Ser Leu Leu Ser Lys
    195                 200                 205

Gln Glu Glu Ser Lys Ala Ala Phe Gly Glu Glu Val Asp Ala Val Asp
210                 215                 220

Thr Gly Ile Ser Arg Glu Thr Ser Ser Asp Val Ala Leu Ala Ser His
225                 230                 235                 240

Ile Leu Thr Ala Leu Arg Glu Lys Gln Ala Pro Glu Leu Ser Leu Ser
            245                 250                 255

Ser Gln Asp Leu Glu Val Gly Gly Asn Gln Gly His
        260                 265
```

<210> SEQ ID NO 10
<211> LENGTH: 2214
<212> TYPE: DNA
<213> ORGANISM: Homo Sapiens

<400> SEQUENCE: 10

```
ggcacgaggc taaatgtaga caatggttag agaagaattt tccaaatgaa tttgcaaaac    60
ttactgtaga aaattcaccc aaacaagaag ctggaattag tgagggtcaa ggaacagcag   120
gggaagaaga ggagaagaaa aacagaagag gaggtggaag gggtcaaata aaacaaaaaa   180
agaagaccgt accacaaaag gttactatag ccaaaattcc cagagcaaag aagaaatatg   240
tgacaagagt atgtggcctt gcaacttttg aaattgatct taaagaagca caaagatttt   300
ttgctcaaaa attctcctgt ggtgcctcag taacagggga ggatgaaatt atcattcagg   360
gagattttac agatgacata attgatgtca ttcaggaaaa atggccagag gtagatgatg   420
acagcatcga gatcttgga gaagtaaaga agtgaatttg aaaatttgtc tgtatttaat    480
ggcctgaact gagagttgat atggccaaag ggagagaggc ctttttaaaat atatatatat   540
atacacatat atatgtatat atacacatat atgtatgtat acacatatac acatgtatat   600
atacatgtgt gtatgtatgc atgtatatac atatatacat acacatatat gtatacatat   660
atacacatat atgtatacat atatacacat atatgtatac atatatatat attctacagt   720
aaaactgtag actgtcctcg tccttggcat tttcactgtt ctgtacaagg ctgcttgttt   780
ttttattgcc aaagtcaaat aaacgggaga ctgtcatgct catgcatgaa tagaatttag   840
tcaaataaaa aattttggtc atttggtact gactttctct ctctctctct ctctcttttt   900
ttttttgac agagtctcgc actgttgcct gggctggaat gcagtggtgc gatctcggct   960
cactgcaacc tccgcctccc gggttcaagt gattctcctg cctcagcctc ccaagtaggt  1020
gggattacag gcgcccgcca ccacgcccag ctaattttg tatttttagt agagatgggg  1080
tttcactatg ttggccaggc tggtctcgaa ctcctgacct cgtgattggc ccacctcagc  1140
ctcccaaagt gctggtatta cagatgtgag ccaccgcacc cagcctgagt ttctcttttct  1200
ctctttttaa ctttattttt tgaaaaaccc ggtagacttt gtggggagca tttttgttga  1260
taattttact gatctaaagc tgagtgatt tttaaaagaa tttgaatttg gcttcctcac  1320
cagtaatatg tctccttgct tctttgatgt gatagttttg agatgggtga gaatctaata  1380
```

```
gatctgtggt tgaatttgct gtgttgttat gaagtccacc ctgtgggcac aataacataa     1440
ctgttggtag gagttgtttg agctattctg gagattattt ggtaaagtat actaaaagcc     1500
ttaaaaccat gtatgtgcgc tgttttgaacc agtaagccac ttctttgaca ttagaagaca     1560
ttagaagaaa taatcagcct tgcataaaac ttatggatga agtattcat cacaatatta     1620 tttataataa aaaattgcaa atgttataaa tgaacaattg ggaaatggtt aaagaagtga     1680
tggtgcattg tgtggtagaa tattatgcat atgtttaaag aatcatattt tctaagatta     1740
tttggaagca tgtttggtaa tgtcaagtgg agtaccccag atacatttta gacatttatc     1800
gtcatcatct gctctgagtg gaaggccgtt cagagaggct agaggttctt attctggcta     1860
taaattatgt gagtaaaatt gtgctaacca gttaaaagta ctgtacaccc atgctcaata     1920
tatagtcctg gaaatagcaa ttgaaacatg tcttctcaca agagaaatg acagttttaa     1980 tgatgtattt gatgaattta aactttaagt caggtgctgc aaattggaaa gaagacttgt     2040
ggtgttttaa gttgctgtgg acactttaa gaaacttaga acccatggaa cccttgttta     2100
tcgccatgca aattacaatc ttgaatgagt gtttttttaa aaataaagta ttagaaaaat     2160
gtgtagtaaa gatgtaaaat taaaaaaaaa aaaaaaaaa aaaaaaaaaa aaaa            2214
```

<210> SEQ ID NO 11
<211> LENGTH: 150
<212> TYPE: PRT
<213> ORGANISM: Homo Sapiens

<400> SEQUENCE: 11

```
His Glu Ala Lys Cys Arg Gln Trp Leu Glu Lys Asn Phe Pro Asn Glu
 1               5                  10                  15

Phe Ala Lys Leu Thr Val Glu Asn Ser Pro Lys Gln Glu Ala Gly Ile
                20                  25                  30

Ser Glu Gly Gln Gly Thr Ala Gly Glu Glu Glu Lys Lys Lys Gln
            35                  40                  45

Lys Arg Gly Gly Arg Gly Gln Ile Lys Gln Lys Lys Thr Val Pro
        50                  55                  60

Gln Lys Val Thr Ile Ala Lys Ile Pro Arg Ala Lys Lys Tyr Val
    65                  70                  75                  80

Thr Arg Val Cys Gly Leu Ala Thr Phe Glu Ile Asp Leu Lys Glu Ala
                85                  90                  95

Gln Arg Phe Phe Ala Gln Lys Phe Ser Cys Gly Ala Ser Val Thr Gly
                100                 105                 110

Glu Asp Glu Ile Ile Ile Gln Gly Asp Phe Thr Asp Asp Ile Ile Asp
                115                 120                 125

Val Ile Gln Glu Lys Trp Pro Glu Val Asp Asp Ser Ile Glu Asp
        130                 135                 140

Leu Gly Glu Val Lys Lys
145                 150
```

<210> SEQ ID NO 12
<211> LENGTH: 433
<212> TYPE: PRT
<213> ORGANISM: Caenorhabditis Elegans

<400> SEQUENCE: 12

```
Pro Tyr Arg Ala Glu Ile Val Ile Ile Gly Gly Gly Leu Ser Gly Ser
 1               5                  10                  15

Ser Thr Ala Phe Trp Leu Lys Glu Arg Phe Arg Asp Glu Asp Phe Lys
                20                  25                  30
```

```
Val Val Val Val Glu Asn Asn Asp Val Phe Thr Lys Ser Ser Thr Met
            35                  40                  45

Leu Ser Thr Gly Gly Ile Thr Gln Gln Phe Ser Ile Pro Glu Phe Val
        50                  55                  60

Asp Met Ser Leu Phe Thr Thr Glu Phe Leu Arg His Ala Gly Glu His
65                  70                  75                  80

Leu Arg Ile Leu Asp Ser Glu Gln Pro Asp Ile Asn Phe Phe Pro Thr
                    85                  90                  95

Gly Tyr Leu Arg Leu Ala Lys Thr Asp Glu Glu Val Glu Met Met Arg
                100                 105                 110

Ser Ala Trp Lys Val Gln Ile Glu Arg Gly Ala Lys Val Gln Leu Leu
            115                 120                 125

Ser Lys Asp Glu Leu Thr Lys Arg Tyr Pro Tyr Met Asn Val Asp Asp
        130                 135                 140

Val Leu Leu Ala Ser Leu Gly Val Glu Asn Glu Gly Thr Ile Asp Thr
145                 150                 155                 160

Trp Gln Leu Leu Ser Ala Ile Arg Glu Lys Asn Ile Thr Leu Gly Val
                    165                 170                 175

Gln Tyr Val Lys Gly Glu Val Glu Gly Phe Gln Phe Glu Arg His Arg
                180                 185                 190

Ala Ser Ser Glu Val His Ala Phe Gly Asp Asp Ala Thr Ala Asp Glu
            195                 200                 205

Asn Lys Leu Arg Ala Gln Arg Ile Ser Gly Val Leu Val Arg Pro Gln
        210                 215                 220

Met Asn Asp Ala Ser Ala Arg Pro Ile Arg Ala His Leu Ile Val Asn
225                 230                 235                 240

Ala Ala Gly Pro Trp Ala Gly Gln Val Ala Lys Met Ala Gly Ile Gly
                    245                 250                 255

Lys Gly Thr Gly Leu Leu Ala Val Pro Val Pro Ile Gln Pro Arg Lys
                260                 265                 270

Arg Asp Val Phe Val Ile Phe Ala Pro Asp Val Pro Ser Asp Leu Pro
            275                 280                 285

Phe Ile Ile Asp Pro Ser Thr Gly Val Phe Cys Arg Gln Thr Asp Ser
        290                 295                 300

Gly Gln Thr Phe Leu Val Gly Arg Thr Pro Ser Lys Glu Glu Asp Ala
305                 310                 315                 320

Lys Arg Asp His Ser Asn Leu Asp Val Asp Tyr Asp Asp Phe Tyr Gln
                    325                 330                 335

Lys Ile Trp Pro Val Leu Val Asp Arg Val Pro Gly Phe Gln Thr Ala
                340                 345                 350

Lys Val Lys Ser Ala Trp Ser Gly Tyr Gln Asp Ile Asn Thr Phe Asp
            355                 360                 365

Asp Ala Pro Val Ile Gly Glu His Pro Leu Tyr Thr Asn Leu His Met
        370                 375                 380

Met Cys Gly Phe Gly Glu Arg Gly Val Met His Ser Met Ala Ala Ala
385                 390                 395                 400

Arg Ala Tyr Ala Glu Arg Ile Phe Asp Gly Ala Tyr Ile Asn Val Asn
                    405                 410                 415

Leu Arg Lys Phe Asp Met Arg Arg Ile Val Lys Met Asp Pro Ile Thr
                420                 425                 430

Glu
```

<210> SEQ ID NO 13
<211> LENGTH: 223
<212> TYPE: PRT
<213> ORGANISM: Homo Sapiens

<400> SEQUENCE: 13

```
Met Lys Val Ala Val Ile Gly Gly Val Ala Gly Leu Ser Ala Ala
 1               5                  10                  15

Tyr Phe Leu Ala Lys Ala Gly Ala Asp Val Lys Val Phe Glu Gln Lys
                20                  25                  30

Tyr Leu Leu Tyr Gly Ala Ser Gly Arg Asn Ser Gly Gly Leu Thr Ala
            35                  40                  45

Gln Phe Thr Asn Glu Ala Met Ile Lys Leu Ala Lys Arg Thr Leu Glu
    50                  55                  60

Leu Tyr Asp Glu Leu Gln Ser Glu Val Gly Phe Asn Phe Leu Leu Arg
65                  70                  75                  80

Arg Asp Gly Tyr Val Lys Ile Ala Gly Lys Gly Glu Glu Ala Lys Leu
                85                  90                  95

Arg Glu Glu Val Glu Phe Gln Arg Lys Ala Gly Val Lys Val Lys Met
                100                 105                 110

Val Glu Pro Glu Phe Val Lys Glu Leu Phe Pro Asp Ile Asn Thr Ser
            115                 120                 125

Ala Phe Thr Ala Ala Ser Tyr Phe Ala Asp Gly Gly Val Val Phe Pro
    130                 135                 140

Trp Pro Val Val Trp Gly Leu Ala Lys Gly Cys Arg Glu Leu Gly Val
145                 150                 155                 160

Glu Ile Tyr Asp Tyr Thr Pro Ala Ser Val Glu Val Lys Gly Asn Asp
                165                 170                 175

Leu Thr Val Lys Ala Ser Gly Glu Ser Tyr Lys Val Asp Tyr Ile Ile
            180                 185                 190

Asn Ala Ala Gly Ala Trp Ser Asn Glu Ile Ser Gln Gln Ala Gly Val
        195                 200                 205

Glu Leu Asn Asn Lys Val Phe Arg Glu Glu Ile Cys Val Thr Glu
    210                 215                 220
```

<210> SEQ ID NO 14
<211> LENGTH: 175
<212> TYPE: PRT
<213> ORGANISM: Drosophila Melanogaster

<400> SEQUENCE: 14

```
Leu Asp Asp Phe Phe Ala Lys Lys Asp Lys Lys Ser Lys Asn Lys
 1               5                  10                  15

Thr Lys Phe Val Thr Ala Asp Glu Met Val Lys Asn Leu Glu Asp Gly
                20                  25                  30

Thr Lys Arg Glu Val Val Lys Pro Lys Pro Glu Ala Ala Ala Gly
            35                  40                  45

Gly Val Ala Val Val Gly Glu Asn Glu Asn Ser Gly Thr Lys Val Pro
    50                  55                  60

Glu Ser Ala Pro Pro Val Glu Glu Trp Lys Glu Phe Glu Glu Glu
65                  70                  75                  80

Gln Arg Lys Asp Tyr Ser Gly Leu Lys Ile Gly Gln Leu Ser Thr Ile
                85                  90                  95

Thr Ala Gln Glu Ser Ala Glu Ser Arg Ala Thr Arg Val Pro Thr Ala
            100                 105                 110

Gln Asp Gly Gly Asn Tyr Asp Glu Asp Asp Glu Asp Ser Asn Gly Tyr
```

```
                        115                 120                 125
Asp Asn Ala Asp Val Asn Lys Glu Arg Val Gly His Gly Pro Trp Lys
        130                 135                 140

Lys Val Val Pro Ala Glu Glu Val Met Gln Ile Pro Val Pro Val Glu
145                 150                 155                 160

Val Glu Lys Pro Ser Ser Lys Thr Tyr Val Ser Pro Ala Leu Arg
                165                 170                 175
```